US011400119B2

(12) United States Patent
Phan et al.

(10) Patent No.: US 11,400,119 B2
(45) Date of Patent: Aug. 2, 2022

(54) METHOD OF TRANSPORTING MESENCHYMAL STEM CELLS BY MEANS OF A TRANSPORTING SOLUTION AND A METHOD OF ADMINISTERING STEM CELLS TO WOUNDS

(71) Applicants: Cellresearch Corporation Pte. Ltd., Singapore (SG); The Regents of the University of Colorado, Denver, CO (US)

(72) Inventors: Toan Thang Phan, Singapore (SG); Brian M. Freed, Aurora, CO (US)

(73) Assignee: Cellresearch Corporation Pte. Ltd., Singapore (SG)

( * ) Notice: Subject to any disclaimer, the term of this patent is extended or adjusted under 35 U.S.C. 154(b) by 232 days.

(21) Appl. No.: 16/378,914

(22) Filed: Apr. 9, 2019

(65) Prior Publication Data
US 2019/0307805 A1    Oct. 10, 2019

Related U.S. Application Data

(60) Provisional application No. 62/655,198, filed on Apr. 9, 2018.

(51) Int. Cl.
*A61K 35/50* (2015.01)
*A61K 35/28* (2015.01)
(Continued)

(52) U.S. Cl.
CPC ............ *A61K 35/28* (2013.01); *A61K 9/0014* (2013.01); *A61P 17/02* (2018.01); *C12N 5/0663* (2013.01)

(58) Field of Classification Search
CPC .................................................. A61K 35/50
See application file for complete search history.

(56) References Cited

U.S. PATENT DOCUMENTS 8,287,854 B2    10/2012  Phan
9,085,755 B2     7/2015  Phan et al.
(Continued)

FOREIGN PATENT DOCUMENTS

EP      2218778 A1     8/2010
WO   2006019357 A1     2/2006
(Continued)

OTHER PUBLICATIONS

Bao et al., The Role of Vascular Endothelial Growth Factor in Wound Healing. J Surg Res. May 15, 2009;153(2):347-358.
(Continued)

*Primary Examiner* — Rosanne Kosson
(74) *Attorney, Agent, or Firm* — Acuity Law Group, PC; Michael A. Whittaker

(57) ABSTRACT

The present invention relates to a method of transporting a stem cell population, the method comprising transporting the stem cell population contacted with a liquid carrier. In addition, the present invention concerns a method of treating a subject having a disease, the method comprising topically administering a defined mesenchymal stem cell population to the subject, wherein the mesenchymal stem cell population is administered within about 96 hours from the time point the mesenchymal stem cell population has been harvested. Also concerned is a unit dosage comprising about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells of a defined mesenchymal stem cell population.

7 Claims, 47 Drawing Sheets
Specification includes a Sequence Listing.

(51) Int. Cl.
  *C12N 5/0775* (2010.01)
  *A61P 17/02* (2006.01)
  *A61K 9/00* (2006.01)

(56) References Cited

U.S. PATENT DOCUMENTS

| | | |
|---|---|---|
| 9,737,568 B2 | 8/2017 | Phan et al. |
| 9,844,571 B2 | 12/2017 | Phan et al. |
| 2006/0078993 A1 | 4/2006 | Phan et al. |
| 2008/0248005 A1 | 10/2008 | Phan |
| 2018/0127721 A1 | 5/2018 | Phan |

FOREIGN PATENT DOCUMENTS

| | | | |
|---|---|---|---|
| WO | 2007046775 A1 | 4/2007 | |
| WO | WO-2007046775 A1 * | 4/2007 | ......... A61L 27/3839 |
| WO | 2008100498 A2 | 8/2008 | |
| WO | 2009115295 A1 | 9/2009 | |
| WO | 2009144008 A1 | 12/2009 | |
| WO | 2009155334 A1 | 12/2009 | |
| WO | 2010064054 A1 | 6/2010 | |
| WO | 2015175457 A1 | 11/2015 | |
| WO | 2017096607 A1 | 6/2017 | |
| WO | 2018067071 A1 | 4/2018 | |

OTHER PUBLICATIONS

Conway et al, Hepatocyte growth factor regulation: An integral part of why wounds become chronic. Wound Repair Regen. Sep.-Oct. 2007;15(5):683-692.

Dominici et al, Minimal criteria for defining multipotent mesenchymal stromal cells. The International Society for Cellular Therapy position statement. Cytotherapy. 2006;8(4):315-317.

Froget et al., Wound healing mediator production by human dermal fibroblasts grown within a collagen-GAG matrix for skin repair in humans. Eur Cytokine Netw. Jan.-Mar. 2003;14(1):60-64.

Hanley et al, Efficient Manufacturing of Therapeutic Mesenchymal Stromal Cells Using the Quantum Cell Expansion System, Cytotherapy. Aug. 2014;16(8):1048-1058.

Jeschke et al., Umbilical Cord Lining Membrane and Wharton's Jelly-Derived Mesenchymal Stem Cells: the Similarities and Differences; The Open Tissue Engineering and Regenerative Medicine Journal, 2011;4:21-27.

Klimanskaya, Embryonic Stem Cells from Blastomeres Maintaining Embryo Viability. Semin Reprod Med. Jan. 2013;31(1):49-55.

Kundrotas, Surface markers distinguishing mesenchymal stem cells from fibroblasts. Acta Medica Lituanica. 2012;19( 2):75-79.

Li et al., Mesenchymal stem cells modified with angiopoietin-1 gene promote wound healing. Stem Cell Res Ther. Sep. 16, 2013;4(5):113.

Li et al., HGF Accelerates Wound Healing by Promoting the Dedifferentiation of Epidermal Cells through $\beta$ 1-Integrin/ILK Pathway. Biomed Res Int. 2013;2013:470418.

Pakyari et al., Critical Role of Transforming Growth Factor Beta in Different Phases of Wound Healing, Adv Wound Care (New Rochelle). Jun. 2013;2(5):215-224.

Ramirez et al., The Role of TGF$\beta$ Signaling in Wound Epithelialization. Adv Wound Care (New Rochelle). Jul. 1, 2014;3(7):482-491.

Sensebe et al., Production of mesenchymal stromal/stem cells according to good manufacturing practices: a review. Stem Cell Res Ther. Jun. 7, 2013;4(3):66.

Stubbendorf et al., Immunological Properties of Extraembryonic Human Mesenchymal Stromal Cells Derived from Gestational Tissue. Stem Cells Dev. Oct. 1, 2013;22(19):2619-2629.

Takahashi et al., Induction of Pluripotent Stem Cells from Adult Human Fibroblasts by Defined Factors. Cell. Nov. 30, 2007;131(5):861-872.

Takahashi and Yamanaka, Induction of Pluripotent Stem Cells from Mouse Embryonic and Adult Fibroblast Cultures by Defined Factors. Cell. Aug. 25, 2006;126(4):663-676.

Tanabe et al., Induction of pluripotency by defined factors. Proc Jpn Acad Ser B Phys Biol Sci. 2014;90(3):83-96.

Vonk et al., Autologous, Allogeneic, Induced Pluripotent Stem Cell or a Combination Stem Cell Therapy? Where Are We Headed in Cartilage Repair and Why: A Concise Review. Stem Cell Res Ther. May 15, 2015;6(1):94.

Yoshida et al., Neutralization of Hepatocyte Growth Factor Leads to Retarded Cutaneous Wound Healing Associated with Decreased Neovascularization and Granulation Tissue Formation. J Invest Dermatol. Feb. 2003;120(2):335-343.

Written Opinion issued in PCT/SG2019/050197 dated Apr. 3, 2020 (9 pages).

Brem and Tonic-Canic, Cellular and molecular basis of wound healing in diabetes. J Clin Invest. May 2007;117(5):1219-22.

Duscher et al., Stem Cells in Wound Healing: The Future of Regenerative Medicine? A MiniReview. Gerontology. 2016;62(2):216-225.

Lam et al., Topical application of mesenchymal stem cells for the treatment of chronic wounds—a pilot study. Cytotherapy, May 2017;19,(5) Supplement:S227 (Poster Abstiact 314).

"Why does a diabetic wound take longer to heal?", accessed online at https://advancedtissue.com/2019/01/why-does-a-diabetic-wound-take-longer-to-heal/ on Jan. 31, 2020 (5 pages).

Baust, Chapter 5: Advances in Media for Cryopreservation and Hypothermic Storage. BioProcess International, Jun. 1, 2005 Jun. 1;3(4):46-56.

The International Search Report and Written Opinion issued in PCT/SG2019/050197 dated Jun. 12, 2019.

Ginis et al., Evaluation of Bone Marrow-Derived Mesenchymal Stem Cells After Cryopreservation and Hypothermic Storage in Clinically Safe Medium. Tissue Eng Part C Methods. Jun. 2012;18(6):453-463.

Harrison et al., Development and validation of broad-spectrum magnetic particle labelling processes for cell therapy manufacturing. Stem Cell Res Ther. 2018;9(248):1-13.

Williams et al., Response to Intravenous Allogeneic Equine Cord Blood-Derived Mesenchymal Stromal Cells Administered from Chilled or Frozen State in Serum and Protein-Free Media. Front Vet Sci. 2016; 3:56 (13 pages).

Extended European Search Report issued in EP 19786015 dated Dec. 3, 2021 (9 pages).

\* cited by examiner

Fig. 1

Lonza www.lonza.com
U.S. Scientific Support: 800-521-0390
scientific.support@lonza.com
EU/ROW Scientific Support: +49-221-99199-400
scientific.support.eu@lonza.com
Document # TS-12-604-3 08/11
© 2011 Lonza Walkersville, Inc.

Dulbecco's modified eagle medium (DMEM)

Product use

Dulbecco's modified eagle medium was developed in 1969 and is a modification of basal medium eagle (BME) that differs from BME and MEM by the following characteristics:
- Vitamins 4X greater than MEM. Vitamins and amino acids greater than BME
- Types and quantities of amino acids greater than MEM and BME
- Iron (ferric nitrate)

Description

- 12-604 With 4.5 g/L glucose, with L-glutamine
- 12-614 With 4.5 g/L glucose, without L-glutamine
- 12-707 With 1.0 g/L glucose, without L-glutamine
- 12-708 With 1.0 g/L glucose, and 25 mM HEPES buffer, without L-glutamine
- 12-709 With 4.5 g/L glucose, and 25 mM HEPES buffer, without L-glutamine
- 12-733 With 4.5 g/L glucose, without L-glutamine, without sodium pyruvate
- 12-741 With 4.5 g/L glucose, with L-glutamine, without sodium pyruvate
- 12-914 With 4.5 g/L glucose, without L-glutamine, screened to support hybridoma growth
- 12-917 With 4.5 g/L glucose, without L-glutamine or phenol red
- 15-604 With 4.5 g/L glucose, with L-glutamine, without sodium pyruvate, powder
- 15-614 With 4.5 g/L glucose, without L-glutamine or sodium pyruvate, powder
  (Powder formulations require the addition of 49.3 ml/L of NaHCO$_3$ 7.5% solution or 3.70 g/L of NaHCO$_3$ powder)

Quick reference chart

| | Glucose | L-glutamine | Phenol red | HEPES buffer | Sodium pyruvate |
|---|---|---|---|---|---|
| 12-604 | 4.5 g/L | + | + | − | + |
| 12-614 | 4.5 g/L | − | + | − | + |
| 12-707 | 1.0 g/L | − | + | − | + |
| 12-708 | 1.0 g/L | − | + | + | + |
| 12-709 | 4.5 g/L | − | + | + | + |
| 12-733 | 4.5 g/L | − | + | − | − |
| 12-741 | 4.5 g/L | + | + | − | − |
| 12-914 | 4.5 g/L | − | + | − | + |
| 12-917 | 4.5 g/L | − | − | − | + |

All trademarks herein are marks of Lonza Group or its subsidiaries.

Fig. 1 continued

Lonza

Specifications

| | Sterility | pH | Osmolality (mOsm) | Cell growth promotion (% of control) | Endotoxin (EU/ml) |
|---|---|---|---|---|---|
| 12-604 | Neg. | 7.0-7.4 | 324-352 | ≥75% | FIO |
| 12-614 | Neg. | 7.0-7.4 | 324-352 | ≥75% | FIO |
| 12-707 | Neg. | 7.0-7.4 | 306-346 | ≥75% | FIO |
| 12-708 | Neg. | 7.03-7.27 | 300-326 | ≥75% | FIO |
| 12-709 | Neg. | 7.0-7.4 | 321-351 | ≥75% | FIO |
| 12-733 | Neg. | 7.0-7.4 | 318-360 | ≥75% | FIO |
| 12-741 | Neg. | 7.0-7.4 | 318-360 | ≥75% | FIO |
| 12-914 | Neg. | 7.0-7.4 | 324-352 | ≥85% ** | FIO |
| 12-917 | Neg. | 7.0-7.4 | 329-343 | ≥75% | FIO |
| 15-604 *** | - | 5.5-7.0 | 235-265 | ≥75% | ≤1.0 |
| 15-614 *** | - | 5.5-7.0 | 235-265 | ≥75% | ≤1.0 |

\* FIO – for information only
\*\* Result of functional test
\*\*\* Moisture content #1.0

Storage
2°C to 8°C

Product use statement
THESE PRODUCTS ARE FOR RESEARCH USE ONLY. Not approved for human or veterinary use, for application to humans or animals, or for use in clinical or *in vitro* procedures.

Ordering information

| Catalog number | Description | Size |
|---|---|---|
| 12-604F | DMEM with 4.5 g/L glucose, with L-glutamine | 500 ml |
| 12-604Q | DMEM with 4.5 g/L glucose, with L-glutamine | 1 L |
| 12-614F | DMEM with 4.5 g/L glucose, without L-glutamine | 500 ml |
| 12-614Q | DMEM with 4.5 g/L glucose, without L-glutamine | 1 L |
| 12-707F | DMEM with 1.0 g/L glucose, without L-glutamine | 500 ml |
| 12-708F | DMEM with 1.0 g/L glucose, and 25 mM HEPES buffer, without L-glutamine | 500 ml |
| 12-709F | DMEM with 4.5 g/L glucose, and 25 mM HEPES buffer, without L-glutamine | 500 ml |
| 12-733F | DMEM with 4.5 g/L glucose, without L-glutamine, without sodium pyruvate | 500 ml |
| 12-733Q | DMEM with 4.5 g/L glucose, without L-glutamine, without sodium pyruvate | 1 L |
| 12-741F | DMEM with 4.5 g/L glucose, with L-glutamine, without sodium pyruvate | 500 ml |
| 12-914F | DMEM with 4.5 g/L glucose, without L-glutamine, screened to support hybridoma growth. | 500 ml |
| 12-917F | DMEM with 4.5 g/L glucose, without L-glutamine or phenol red. | 500 ml |
| 15-604D | DMEM with 4.5 g/L glucose, with L-glutamine, without sodium pyruvate, powder | 1 x 10L |
| 15-604F | DMEM with 4.5 g/L glucose, without L-glutamine or sodium pyruvate, powder | 1 X 50L |
| 15-614D | DMEM with 4.5 g/L glucose, without L-glutamine or sodium pyruvate, powder | 1 x 10L |

All trademarks herein are marks of Lonza Group or its subsidiaries.

Fig. 2

Lonza

Lonza Walkersville, Inc.
www.lonza.com
biotechserv@lonza.com
Tech Service: 800-521-0390
Document # TS 12-615-2 11/08
Walkersville, MD 21793-0127 USA
© 2008 Lonza Walkersville, Inc.

Ham's F12 Medium

Product Use
Ham's F12 Medium is a nutrient mixture designed to cultivate a wide variety of mammalian and hybridoma cells when used with serum in combination with hormones and transferrin.

Specifications

| Sterility | pH | Osmolality (mOsm) |
|---|---|---|
| Negative | 7.07-7.40 | 286-305 |

| Cell Growth Generation | Endotoxin (EU/ml) |
|---|---|
| ≥75% of control | FIO |

Storage
2°C to 8°C

Product Use Statement
THESE PRODUCTS ARE FOR RESEARCH USE ONLY. Not approved for human or veterinary use, for application to humans or animals, or for use in clinical or *in vitro* procedures.

Ordering Information

| Catalog Number | Description | Size |
|---|---|---|
| 12-615F | Ham's F12 Medium with L-glutamine | 500 ml |

All trademarks herein are marks of Lonza Group or its subsidiaries.

Fig. 3

Lonza www.lonza.com
U.S. Scientific Support: 800-521-0390
scientific.support@lonza.com
EU/ROW Scientific Support: +49-221-99199-400
scientific.support.eu@lonza.com
Document # TS-12-719-3 08/11
© 2011 Lonza Walkersville, Inc.

DMEM: F12 (1:1) medium

Product use
DMEM combined with Hams F12 has been extensively used to demonstrate the effect of various hormones and growth factors on target tissues.

Description
| | |
|---|---|
| 12-719 | with L-glutamine, 15 mM HEPES, and 3.151 g/L glucose |
| 15-719 | powder – with L-glutamine, 15 mM HEPES, and 3.151 g/L glucose. Powdered medium requires the addition of 16.0 ml/L of $NaHCO_3$, 7.5% solution or 1.2 g/L $NaHCO_3$ powder |
| 04-687 | with 3.151 g/L glucose, with L-glutamine, without HEPES |

Specifications

| | Sterility | pH | Osmolality (mOsm) |
|---|---|---|---|
| 12-719 | Negative | 7.0-7.4 | 286-356 |
| 15-719* | Negative | 4.5-6.5 | 260-290 |
| 04-687 | Negative | FIO | FIO |

| | Cell growth promotion | Endotoxin (EU/ml) | Moisture |
|---|---|---|---|
| 12-719 | ≥ 75% of control | FIO | -- |
| 15-719* | ≥ 75% of control | ≤ 1 EU/ml | ≤ 2% |
| 04-687 | -- | FIO | -- |

* pH, osmolality, endotoxin, and moisture are done without $NaHCO_3$; $NaHCO_3$ is added for cell growth test.

Storage
2°C to 8°C

Product use statement
THESE PRODUCTS ARE FOR RESEARCH USE ONLY. Not approved for human or veterinary use, for application to humans or animals, or for use in clinical or *in vitro* procedures.

Ordering information

| Catalog number | Description | Size |
|---|---|---|
| 12-719F | DMEM: F12 with L-glutamine, 15 mM HEPES, and 3.151 g/L glucose | 500 ml |
| 12-719Q | DMEM: F12 with L-glutamine, 15 mM HEPES, and 3.151 g/L glucose | 1 L |
| 15-719D | DMEM: F12 powder – with L-glutamine, 15 mM HEPES, and 3.151 g/L glucose. Powdered medium requires the addition of 16.0 ml/L of $NaHCO_3$, 7.5% solution or 1.2 g/L $NaHCO_3$ powder | 1 x 10L |
| 04-687Q | DMEM: F12 with 3.151 g/L glucose, with L-glutamine, without HEPES | 1 L |

Cascade Biologics™
invitrogen cell culture

invitrogen cell culture

FIG. 4
Medium 171, Medium 171PRF, and MEGS

Medium 171
M-171-500
500 ml

Medium 171PRF
(Phenol Red-Free)
M-171PRF-500
500 ml

Product Description
Medium 171 and Medium 171PRF are sterile, liquid tissue culture media intended for use as one component in a complete culture environment for the growth of normal human mammary epithelial cells. Medium 171 is a basal medium containing essential and non-essential amino acids, vitamins, other organic compounds, trace minerals, and inorganic salts. Medium 171PRF is a phenol red-free version of Medium 171. These media do not contain antibiotics, antimycotics, hormones, growth factors, or proteins. These media are HEPES and bicarbonate buffered and are designed for use in an incubator with an atmosphere of 5% $CO_2$/95% air. To support plating and long-term proliferation of normal human mammary epithelial cells, these media must be supplemented with Mammary Epithelial Growth Supplement (MEGS, cat. no S-015-5).

Intended Use
Medium 171 is intended for use in the routine culture of normal human mammary epithelial cells. Medium 171PRF is intended for use by investigators who wish to culture normal human mammary epithelial cells in the absence of phenol red. When supplemented with MEGS, these media will support the plating and proliferation of normal human mammary epithelial cells at densities between $2.5 \times 10^3$ cells/cm$^2$ and $8 \times 10^4$ cells/cm$^2$. *This product is for research use only. Not for use in animals, humans, or diagnostic procedures.*

*Caution: If handled improperly, some components of this product may present a health hazard. Take appropriate precautions when handling this product, including the wearing of protective clothing and eyewear. Dispose of properly.*

Storage and Stability
Medium 171 and Medium 171PRF are stored at 4° C in our facility and are shipped at ambient temperature. Upon receipt, these media should be stored at 4° C and should not be frozen. Protect from light. Several components of these tissue culture media are light-labile, and we recommend that the media not be exposed to light for lengthy periods of time. If the media are warmed prior to use, do not exceed 37° C. When stored in the dark at 4° C, the product is stable until the expiration date on the label.

Preparation of Supplemented Medium 171
1. Thaw one bottle of MEGS. Take one bottle of Medium from cold storage. Make sure that the caps of the vessels are tight.
2. Gently swirl the bottle of supplement. Avoid splashing the supplement into the cap of the bottle or causing the supplement to foam.
3. Wipe the outside of the containers with a disinfecting solution such as 70% ethanol or isopropanol.
4. Using sterile technique in a laminar flow culture hood, transfer the entire contents of the bottle of supplement to the bottle of Medium.
5. Tightly cap the bottle of supplemented medium and swirl the contents to ensure a homogeneous solution. Avoid causing the medium to foam.

Storage and Stability of Supplemented Medium 171
Once Medium 171 or Medium 171PRF has been supplemented with MEGS, the supplemented medium should be stored in the dark at 4° C and should not be frozen. When stored in the dark at 4° C, the supplemented medium is stable for 1 month.

Selected References
The Medium 171 formulation is based on medium MCDB 170, with modifications.

Hammond SL, Ham RG, Stampfer MR; PNAS 81:5435-5439, 1984

 

Fig. 4 continued

MEGS
Mammary Epithelial Growth Supplement
Cat. no. S-015-5
5 ml

Product Description
Mammary Epithelial Growth Supplement (MEGS) is a sterile, concentrated (100X) solution intended for use as one component in a complete culture environment for the growth of normal human mammary epithelial cells. Each 5 ml bottle of MEGS contains all of the growth factors, hormones, and tissue extracts necessary for the culture of normal human mammary epithelial cells and is the correct amount of supplement for a 500 ml bottle of Medium 171 or Medium 171PRF. MEGS is an ionically-balanced supplement containing bovine pituitary extract (BPE), bovine insulin, hydrocortisone and recombinant human epidermal growth factor. When a 500 ml bottle of Medium 171 or Medium 171PRF is supplemented with MEGS, the final concentrations of the components in the supplemented medium are: BPE, 0.4% v/v; bovine insulin, 5 µg/ml; hydrocortisone, 0.5 µg/ml; and recombinant human epidermal growth factor, 3 ng/ml.

Intended Use
MEGS is intended for use in conjunction with Medium 171 or Medium 171PRF for the routine serum-free culture of normal human mammary epithelial cells. *This product is for research use only. Not for use in animals, humans, or diagnostic procedures.*

*Caution: If handled improperly, some components of this product may present a health hazard. Take appropriate precautions when handling this product, including the wearing of protective clothing and eyewear. Dispose of properly.*

Storage and Stability
MEGS is stored at –20° C at our facility and is shipped on dry ice. Upon receipt, the product should be stored at –20° C in a freezer that is not self-defrosting. When stored at –20° C, the product is stable until the expiration date shown on the label.

After long-term storage at –20° C, MEGS may contain a small amount of precipitate. This precipitate is formed from cold-insoluble material in the BPE component of the MEGS and will not affect the performance of the product.

Thawing
To thaw, place the product in a 37° C water bath or overnight at 4° C. If thawed in a water bath, do not leave the product at 37° C after the product has thawed. For instructions on adding MEGS to Medium 171, please refer to the instructions that accompany the basal medium.

Selected References
The MEGS formulation is based on published supplementation of medium MCDB 170, with modifications.

Hammond SL, Ham RG, Stampfer MR; PNAS 81:5435-5439, 1984.

Limited Use Label License No. 5: Invitrogen Technology

The purchase of this product conveys to the buyer the non-transferable right to use the purchased amount of the product and components of the product in research conducted by the buyer (whether the buyer is an academic or for-profit entity). The buyer cannot sell or otherwise transfer (a) this product (b) its components or (c) materials made using this product or its components to a third party or otherwise use this product or its components or materials made using this product or its components for Commercial Purposes. The buyer may transfer information or materials made through the use of this product to a scientific collaborator, provided that such transfer is not for any Commercial Purpose, and that such collaborator agrees in writing (a) not to transfer such materials to any third party, and (b) to use such transferred materials and/or information solely for research and not for Commercial Purposes. Commercial Purposes means any activity by a party for consideration and may include, but is not limited to: (1) use of the product or its components in manufacturing; (2) use of the product or its components to provide a service, information, or data; (3) use of the product or its components for therapeutic, diagnostic or prophylactic purposes; or (4) resale of the product or its components, whether or not such product or its components are resold for use in research. For products that are subject to multiple limited use label licenses, the terms of the most restrictive limited use label license shall control. Life Technologies Corporation will not assert a claim against the buyer of infringement of patents owned or controlled by Life Technologies Corporation which cover this product based upon the manufacture, use or sale of a therapeutic, clinical diagnostic, vaccine or prophylactic product developed in research by the buyer in which this product or its components was employed, provided that neither this product nor any of its components was used in the manufacture of such product. If the purchaser is not willing to accept the limitations of this limited use statement, Life Technologies is willing to accept return of the product with a full refund. For information on purchasing a license to this product for purposes other than research, contact Licensing Department, Life Technologies Corporation, 5791 Van Allen Way, Carlsbad, California 92008. Phone (760) 603-7200. Fax (760) 602-6500. Email: outlicensing@invitrogen.com.

©2009 Life Technologies Corporation. All rights reserved.
For research use only. Not intended for any animal or human therapeutic or diagnostic use.

*For research use only.*
Life Technologies Corporation • 5791 Van Allen Way • Carlsbad • CA 92008 • Tel: 800.955.6288 • www.invitrogen.com • E-mail: tech_support@invitrogen.com MAN0001585                                                                                          Revised: 30 May 2009

Fig. 5

PTT6 Medium ingredients list

| Medium composition List | Company Name | Catalogue Number |
|---|---|---|

Basic media

| Medium composition List | Company Name | Catalogue Number |
|---|---|---|
| DMEM (also referred to herein as PTT6-basal medium) | Lonza | 12-604F |
| DMEM/F12 | Lonza | 12-719F |
| M171 | Life technologies | M171500 |

Serum

| | | |
|---|---|---|
| Fetal Bovine Serum | GE Healthcare | A15-151 |

Antibiotic

| | | |
|---|---|---|
| Penicillin-Streptomycin-Amphotericin B | Lonza | 17-745E |

Supplements

| | | |
|---|---|---|
| Adenine (optional) | Sigma | A8626-25G |
| Hydrocortisone (optional) | Sigma | H-0888 |
| Epidermal Growth Factor | Millipore | GF-144 |
| T3 (3,3′,5-Triiodo-L-thyronine sodium salt) (optional) | Sigma | 200-223-5 |
| Recombinant Human Insulin AOF | Life Technologies | A11382IJ |

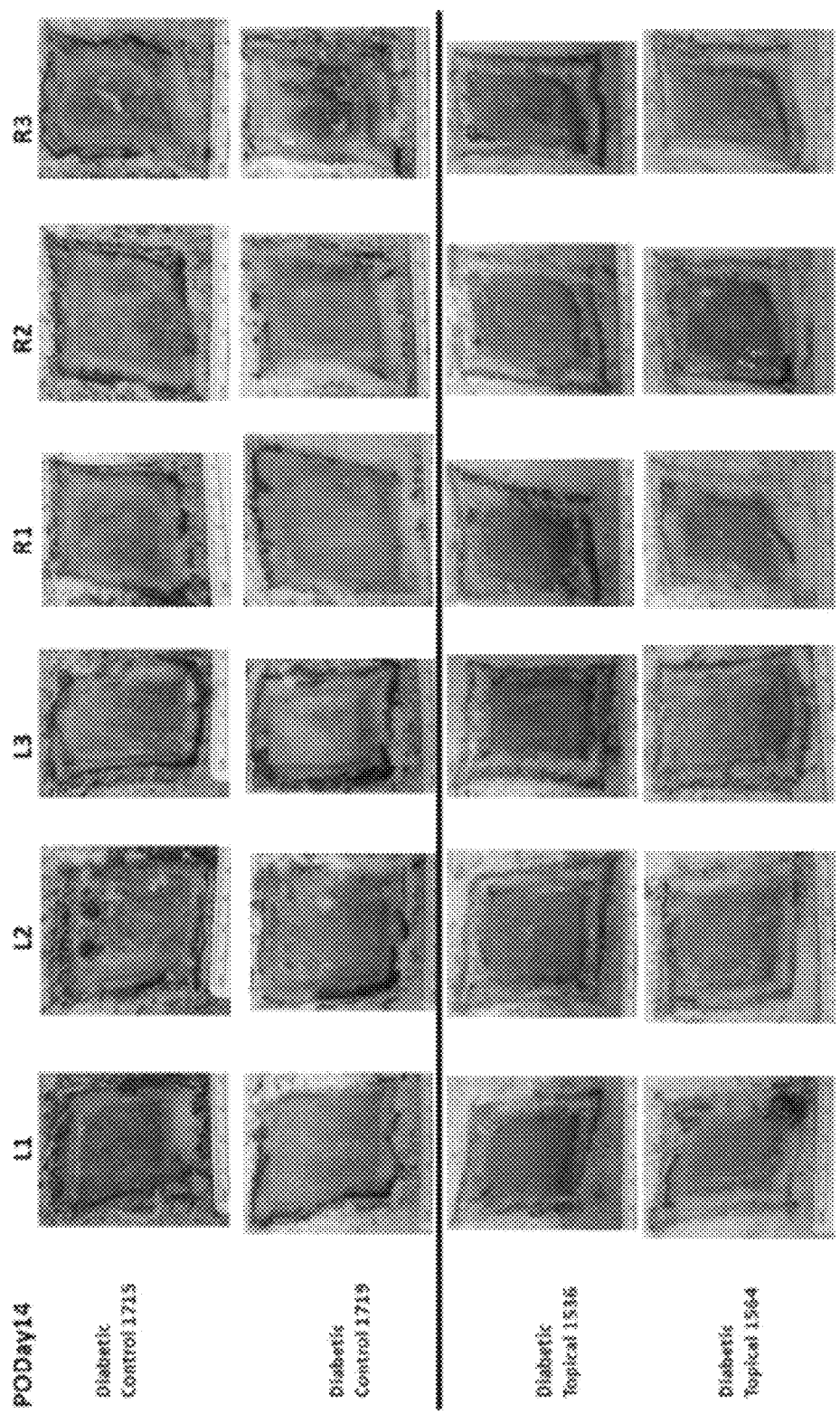

Figure 19

Certificate of Analysis

Print Date: Sep 16th 2016 www.tocris.com

Product Name: Trolox     Catalog No.: 6002     Batch No.: 1
CAS Number: 53188-07-1
IUPAC Name: 3,4-Dihydro-6-hydroxy-2,5,7,8-tetramethyl-2H-1-benzopyran-2-carboxylic acid

1. PHYSICAL AND CHEMICAL PROPERTIES

Batch Molecular Formula: $C_{14}H_{18}O_4 \cdot \tfrac{1}{2}H_2O$

Batch Molecular Weight: 259.3

Physical Appearance: Beige solid

Solubility: DMSO to 100 mM
ethanol to 100 mM

Storage: Store at +4°C

Batch Molecular Structure:

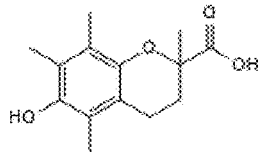

2. ANALYTICAL DATA

HPLC: Shows 99.7% purity

$^1$H NMR: Consistent with structure

Mass Spectrum: Consistent with structure

Microanalysis:

|  | Carbon | Hydrogen | Nitrogen |
|---|---|---|---|
| Theoretical | 64.85 | 7.39 | |
| Found | 64.72 | 7.58 | |

Caution - Not Fully Tested • Research Use Only • Not For Human or Veterinary Use

| bio-techne.com | North America | China | Europe Middle East Africa | Rest of World |
|---|---|---|---|---|
| info@bio-techne.com | Tel: (800) 343 7475 | info.cn@bio-techne.com | Tel: +44 (0)1235 529449 | www.tocris.com/distributors |
| techsupport@bio-techne.com | | Tel: +86 (21) 52380373 | | Tel: +1 612 379 2956 |

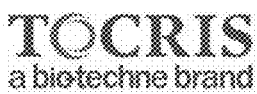

Figure 19 continued

Product Information

Print Date: Sep 16th 2016 www.tocris.com

Product Name: Trolox    Catalog No.: 6002    Batch No.: 1
CAS Number: 53188-07-1
IUPAC Name: 3,4-Dihydro-6-hydroxy-2,5,7,8-tetramethyl-2H-1-benzopyran-2-carboxylic acid

Description:
Antioxidant vitamin E derivative; suppresses osteoclast formation and inhibits IL-1-induced osteoclast bone loss. Cell-permeable and water soluble.

Physical and Chemical Properties:
Batch Molecular Formula: $C_{14}H_{18}O_4 \cdot \tfrac{1}{2}H_2O$
Batch Molecular Weight: 259.3
Physical Appearance: Beige solid

Minimum Purity: >98%

Batch Molecular Structure:

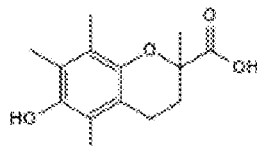

Storage: Store at +4°C

Solubility & Usage Info:
DMSO to 100 mM
ethanol to 100 mM

Stability and Solubility Advice:
Some solutions can be difficult to obtain and can be encouraged by rapid stirring, sonication or gentle warming (in a 45-60°C water bath).
Information concerning product stability, particularly in solution, has rarely been reported and in most cases we can only offer a general guide. Our standard recommendations are:
SOLIDS: Provided storage is as stated on the product label and the vial is kept tightly sealed, the product can be stored for up to 6 months from date of receipt.
SOLUTIONS: We recommend that stock solutions, once prepared, are stored aliquoted in tightly sealed vials at -20°C or below and used within 1 month. Wherever possible solutions should be made up and used on the same day.

References:
Lee et al (2009) Trolox prevents osteoclastogenesis by suppressing RANKL expression and signaling. J.Biol.Chem. 284 13725. PMID: 19299513.
Giulivi et al (1993) Inhibition of protein radical reactions of ferrylmyoglobin by the water-soluble analog of vitamin E, Trolox C. Arch.Biochem.Biophys. 303 152. PMID: 8489259.

Caution - Not Fully Tested • Research Use Only • Not For Human or Veterinary Use

| bio-techne.com | North America | China | Europe Middle East Africa | Rest of World |
|---|---|---|---|---|
| info@bio-techne.com | Tel: (800) 343 7475 | info.cn@bio-techne.com | Tel: +44 (0)1235 529449 | www.tocris.com/distributors |
| techsupport@bio-techne.com | | Tel: +86 (21) 52380373 | | Tel:+1 612 379 2956 |

Figure 20

SIGMA-ALDRICH

3050 Spruce Street, Saint Louis, MO 63103, USA
Website: www.sigmaaldrich.com
Email USA: techserv@sial.com
Outside USA: eurtechserv@sial.com

Product Specification

Product Name:
Sodium chloride - PharmaGrade, USP, Manufactured under appropriate GMP controls for pharma or biopharmaceutical production.

Product Number: RES0926S-A7
CAS Number: 7647-14-5

Formula: NaCl
Formula Weight: 58.44 g/mol

| TEST | Specification |
|---|---|
| Appearance (Color) | White |
| Appearance (Form) | Powder |
| Appearance of Solution (Turbid 20% aqueous | Clear |
| Appearance of Solution (Color) 20% aqueous | Colorless |
| Heavy Metals (per USP) | $\leq$ 5 ppm |
| Identification | Pass |
| Iodides | Pass |
| Iron (Fe) | $\leq$ 2.0 µG/g |
| Limit of Bromides | $\leq$ 0.010 % |
| Limit of Phosphate | $\leq$ 0.0025 % |
| Limit of Potassium | $\leq$ 0.05 % |
| Loss on Drying (USP) | $\leq$ 0.5 % |
| Acidity or Alkalinity | Pass |
| Aluminum (Al) | $\leq$ 0.2 µG/g |
| Arsenic (As) | $\leq$ 1.0 µG/g |
| Assay Dried basis | 99.0 - 100.5 % |
| Barium (USP) | Pass |
| Chloride | Pass |
| Ferrocyanides | Pass |
| Magnesium/Alkaline Earth Metal | Pass |
| Nitrites | Pass |
| Sulfate (SO4) | $\leq$ 0.020 % |

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

Figure 20 continued

SIGMA-ALDRICH

3050 Spruce Street, Saint Louis, MO 63103, USA
Website: www.sigmaaldrich.com
Email USA: techserv@sial.com
Outside USA: eurtechserv@sial.com

Product Specification

Product Name:
Sodium chloride - PharmaGrade, USP, Manufactured under appropriate GMP controls for pharma or biopharmaceutical production.

Product Number: RES0926S-A7
CAS Number: 7647-14-5

Formula: NaCl
Formula Weight: 58.44 g/mol

| TEST | Specification |
|---|---|

Specification: PRD.0.ZQ5.10000051146

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

SIGMA-ALDRICH® Figure 21

3050 Spruce Street, Saint Louis, MO 63103, USA
Website: www.sigmaaldrich.com
Email USA: techserv@sial.com
Outside USA: eurtechserv@sial.com

Product Specification

Product Name:
Potassium phosphate monobasic - 99.99% trace metals basis

Product Number: 229806
CAS Number: 7778-77-0
MDL: MFCD00011401
Formula: H2KO4P
Formula Weight: 136.09 g/mol $KH_2PO_4$

| TEST | Specification |
|---|---|
| Appearance (Color) | Conforms to Requirements |
|     White or Colorless | |
| Appearance (Form) | Powder or Crystals |
| Purity (Titration by NAOH) | 22.3 - 23.2 % |
|     % P | |
| ICP Major Analysis | Confirmed |
|     Confirms Potassium and Phosphorus Components | |
| Trace Metal Analysis | ≤ 150.0 ppm |
| Purity | Meets Requirements |
|     99.99% Based On Trace Metals Analysis | |

Specification: PRD.2.ZQ5.10000038396

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

Figure 22

SIGMA-ALDRICH sigma-aldrich.com

3050 Spruce Street, Saint Louis, MO 63103, USA
Website: www.sigmaaldrich.com
Email USA: techserv@sial.com
Outside USA: eurtechserv@sial.com

Product Specification

Product Name:
HEPES - PharmaGrade, Manufactured under appropriate controls for use as a raw material in pharma or biopharmaceutical production, suitable for cell culture Product Number: RES6003H-B7
CAS Number: 7365-45-9

Formula: C8H18N2O4S
Formula Weight: 238.3 g/mol

| TEST | Specification |
|---|---|
| Appearance (Color) | White |
| Appearance (Form) | Free Flowing Powder |
| Infrared Spectrum | Conforms to Reference |
| Solubility (Turbidity) 1.0M aqueous | Clear |
| Solubility (Color) 1.0M aqueous | Colorless |
| Solubility (Form) 1.0M aqueous | Solution |
| Water (by Karl Fischer) | $\leq$ 0.5 % |
| Titration by NaOH | $\geq$ 99.5 % |
| Cytotoxicity | Pass |
| DNase - Nickase | Pass |
| DNase-Endo/Exonuclease | Pass |
| RNAse Detection | Pass |
| pH 1.0% aqueous | 4.7 - 5.3 |
| Endotoxin | $\leq$ 50 EU/g |
| Yeast and Mold | $\leq$ 100 CFU/g |
| Bioburden | $\leq$ 100 CFU/g |
| Protease Detection | Pass |
| Residue on Ignition | $\leq$ 0.1 % |
| Arsenic (As) | $\leq$ 3.0 ppm |
| Iron (Fe) | $\leq$ 5.0 ppm |
| Zinc (Zn) | $\leq$ 5.0 ppm |

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

Figure 22 continued

SIGMA-ALDRICH sigma-aldrich.com

3050 Spruce Street, Saint Louis, MO 63103, USA
Website: www.sigmaaldrich.com
Email USA: techserv@sial.com
Outside USA: eurtechserv@sial.com

Product Specification

Product Name:
HEPES – PharmaGrade, Manufactured under appropriate controls for use as a raw material in pharma or biopharmaceutical production, suitable for cell culture Product Number: RES6003H-B7
CAS Number: 7365-45-9

Formula: C8H18N2O4S
Formula Weight: 238.3 g/mol

| TEST | Specification |
|---|---|
| Nickel (Ni) | ≤ 5.0 ppm |
| Magnesium (Mg) | ≤ 5.0 ppm |
| Calcium (Ca) | ≤ 30.0 ppm |
| Lead (Pb) | ≤ 5.0 ppm |
| Bismuth (Bi) | ≤ 5.0 ppm |
| Lithium (Li) | ≤ 5.0 ppm |
| Molybdenum (Mo) | ≤ 5.0 ppm |
| Aluminum (Al) | ≤ 5.0 ppm |
| Antimony (Sb) | ≤ 5.0 ppm |
| Barium (Ba) | ≤ 5.0 ppm |
| Cobalt (Co) | ≤ 5.0 ppm |
| Chromium (Cr) | ≤ 5.0 ppm |
| Cadmium (Cd) | ≤ 5.0 ppm |
| Copper (Cu) | ≤ 5.0 ppm |
| Manganese (Mn) | ≤ 5.0 ppm |
| UV Absorbance 260nm 1.0M aqueous | ≤ 0.05 Abs UN |
| UV Absorbance 280nm 1.0M aqueous | ≤ 0.04 Abs UN |

Specification: PRD.0.ZQ5.10000050458

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

12/26/2017 COMBI-BLOCKS QW-1395 p.1

Figure 23

Safety Data Sheet

1. Identification of the substance

*Product Name:* Sodium lactobionate
*Synonyms:*
*Catalog number:* QW-1395
*Supplier:* Combi-Blocks, Inc., 7949 Silverton Ave # 915, San Diego, CA 92126, USA. Tel: 858-635-8950

2. Hazards identification

No known hazard.

3. Composition/information on ingredients.

*Ingredient name:* Sodium lactobionate
*CAS number:* 27297-39-8

4. First aid measures

*Skin contact:* Immediately wash skin with copious amounts of water for at least 15 minutes while removing contaminated clothing and shoes. If irritation persists, seek medical attention.

*Eye contact:* Immediately wash skin with copious amounts of water for at least 15 minutes. Assure adequate flushing of the eyes by separating the eyelids with fingers. If irritation persists, seek medical attention.

*Inhalation:* Remove to fresh air. In severe cases or if symptoms persist, seek medical attention.

*Ingestion:* Wash out mouth with copious amounts of water for at least 15 minutes. Seek medical attention.

5. Fire fighting measures

In the event of a fire involving this material, alone or in combination with other materials, use dry powder or carbon dioxide extinguishers. Protective clothing and self-contained breathing apparatus should be worn.

6. Accidental release measures

*Personal precautions:* Wear suitable personal protective equipment which performs satisfactorily and meets local/state/national standards.

| | |
|---|---|
| Respiratory precaution: | Wear approved mask/respirator |
| Hand precaution: | Wear suitable gloves/gauntlets |
| Skin protection: | Wear suitable protective clothing |
| Eye protection: | Wear suitable eye protection |

*Methods for cleaning up:* Mix with sand or similar inert absorbent material, sweep up and keep in a tightly closed container for disposal. See section 12.

*Environmental precautions:* Do not allow material to enter drains or water courses.

7. Handling and storage

*Handling:* This product should be handled only by, or under the close supervision of, those properly qualified in the handling and use of potentially hazardous chemicals, who should take into account the fire, health and chemical hazard data given on this sheet.

*Storage:* Store in closed vessels.

8. Exposure Controls / Personal protection

*Engineering Controls:* Use only in a chemical fume hood.
*Personal protective equipment:* Wear laboratory clothing, chemical-resistant gloves and safety goggles.
*General hydiene measures:* Wash thoroughly after handling. Wash contaminated clothing before reuse.

12/26/2017 COMBI-BLOCKS QW-1395 p.2

Figure 23 continued

9. Physical and chemical properties

| | |
|---|---|
| *Appearance:* | Not specified |
| *Boiling point:* | No data |
| *Melting point:* | No data |
| *Flash point:* | No data |
| *Density:* | No data |
| *Molecular formula:* | $C_{12}H_{21}O_{12}.Na$ |
| *Molecular weight:* | 380.3 |

10. Stability and reactivity

*Conditions to avoid:* Heat, flames and sparks.
*Materials to avoid:* Oxidizing agents.
*Possible hazardous combustion products:* Carbon monoxide, nitrogen oxides.

11. Toxicological information

*Acute toxicity:* No data available.
*Skin irritation/corrosion:* No data available.
*Eye damage/irritation:* No data available.
*Respiratory or skin sensitization:* No data available.
*Germ cell mutagenicity:* No data available.
*Carcinogenicity:* No classification data on carcinogenic properties of this material is available from EPA, IARC, NTP, OSHA or ACGIH.
*Reproductive toxicity:* No effects known.
*Specific target organ system toxicity - repeated exposure:* No effects known.
*Specific target organ system toxicity - single exposure:* No data available.
*Aspiration hazard:* No data available.
*Additional information:* To the best of our knowledge, the chemical, physical and toxicological properties of this substance have not been thoroughly investigated.

12. Ecological information

*Toxicity:* No data available.
*Persistence and degradability:* No data available.
*Bioaccumulative potential:* No data available.
*Mobility in soil:* No data available.
*Result of PBT and vPvB assessment:* PBT: Not applicabel. vPvB: Not applicable.
*Other adverse effects:* No further relevant information available.

13. Disposal consideration

Arrange disposal as special waste, by licensed disposal company, in consultation with local waste disposal authority, in accordance with national and regional regulations.

14. Transportation information

No known hazard for air and ground transportation.

15. Regulatory information

No chemicals in this material are subject to the reporting requirements of SARA Title III, Section 302, or have known CAS numbers that exceed the threshold reporting levels established by SARA Title III, Section 313.

12/26/2017 COMBI-BLOCKS QW-1395 p.3

16. Other information

This MSDS is correct to the best of our knowledge at the date of publication but does not purport to be all inclusive and shall be used only as a guide. Combi-Blocks shall not be held liable for any injury or damage resulting from handling or from contact with the above product.

VWR is now an Avantor® brand — LEARN MORE

Search FAQ   Contact   Find a Distributor   Manage Subscriptions   Sign in ▾   United States / English ▾

Mannitol, Powder, USP - GenAR®

Formula: $C_6H_{14}O_6$
Formula Weight: 182.17
Suitable for Use in Biotechnology

| Select Size | Product Number | Units per Case | Package Size | Container Type | Price per Unit | Case Price per Unit | Min Order in Units | Quantity (Units) |
|---|---|---|---|---|---|---|---|---|
| ☐ | 7781-88 | 1 | 12KG | 6.5GL polyethylene pail screw top | $1467.49 | -- | 1 | ☐ |

You must be logged in to add the products to the cart.
* Products noted with an asterisk (*) in the "Units Per Case" column are available for sale in case units of measure only.

The following product(s) have been removed from catalog:

| Removed Products | Package Size | Equivalent Products | Equivalent Pkg Size | Comments/Notes |
|---|---|---|---|---|
| 7781-04 | 500G | Not Available | -- | Please contact Customer Services. |

Product Specifications

| TEST | SPECIFICATION |
|---|---|
| GMP Manufactured Product | |
| Meets B.P. Chemical Specifications | |
| Meets E.P. Chemical Specifications | |
| Meets U.S.P Requirements | |
| CAUTION: For Manufacturing, processing or repackaging | |
| Bulk Pharmaceutical Chemical | |
| USP - Assay (dried basis) | 97.0 - 102.0 % |
| USP - Identification | Passes Test |
| USP - Related Substances: Sorbitol | <= 2.0 % |
| USP - Related Substances: Sum of isomalt & maltitol | <= 2.0 % |
| USP - Related Substances: Unspecified impurities | <= 0.10 % |
| USP - Related Substances: Total Impurities | <= 2.0 % |
| USP - Loss on Drying at 105°C | <= 0.5 % |
| USP - Melting Point | 165 - 170 °C |
| USP - Reducing Sugars | <= 0.1 % |
| USP - Nickel (Ni) | <= 1 ppm |
| USP - Appearance of Solution | Passes Test |
| USP - Conductivity (uS cm-1) | <= 20 µS/cm |
| USP -- Total Anerobic Microbial Count | <= 100 cfu/g |

| | |
|---|---|
| USP - Total Yeast and Mold Count | <= 100 cfu/g |
| USP - Escherichia coli | Passes Test |
| EP/BP - Assay (as $C_6H_{14}O_6$) (calculated on anhydrous basis) | 97.0 - 102.0 % |
| EP/BP - Conductivity, uS cm-1 | <= 20 |
| EP/BP - Identification C | Passes Test |
| EP/BP - Melting Point | 165 - 170 °C |
| EP/BP - Heavy Metals (as Pb) | <= 5 ppm |
| EP/BP - Nickel (Ni) | <= 1 ppm |
| EP/BP - Loss on Drying | <= 0.5 % |
| EP/BP - Reducing Sugars | <= 0.1 % |
| EP/BP - Related Substances: Impurity A | <= 2.0 % |
| EP/BP - Related Substances: Sum of Impurities B & C | <= 2.0 % |
| EP/BP - Related Substances: Unspecified Impurities, each | <= 0.10 % |
| EP/BP - Related Substances: Total Impurities | <= 2.0 % |
| EP/BP - Appearance of Solution | Passes Test |
| Total Aerobic Microbial Count (cfu/g) | <= 1000 |
| Total Mold and Yeast Count (cfu/g) | <= 100 |
| EP/BP - Escherichia coli (absent) | Passes Test |
| Salmonella (absent) | Passes Test |
| Endotoxin Concentration (EU/g) | <= 10 |
| Appearance (fine, white crystalline powder) | |
| Not intended for Parenteral Use | |
| Only Class 2 solvents (Ethylene Glycol) are likely to be present. All are below Option 1 limits. | |
| Metallic Residues: No metal catalysts or metal reagents, as defined by EMA Guideline EMEA/CHMP/SWP/4446/2000, are used in the production of this material. | |

Product Information

| | |
|---|---|
| CAS Number | 69-65-8 |
| HTS Number | 2905430000 |
| Density | 1 L = 1.52 Kg |
| Management of Change | R |

Figure 26

D-(+)-Glucose

Product Number G 8270
Store at Room Temperature

Product Description
Molecular Formula: $C_6H_{12}O_6$
CAS Number: 50-99-7
Molecular Weight: 180.2
Melting Point : 146 °C for α-D-glucose and 150 °C for β-D-glucose[1]
pH: 5.9 (0.5 M aqueous)[2]

Densities of aqueous solutions (w/v) at 17.5 °C with respect to water:[2]

| Concentration (%) | 5 | 10 | 20 | 30 | 40 |
|---|---|---|---|---|---|
| Density (g/ml) | 1.019 | 1.038 | 1.076 | 1.113 | 1.149 |

Glucose is a main source of energy for living organisms. Glucose occurs naturally in the free state in fruits and other parts of plants. Glucose is combined into glucosides, disaccharides, oligosaccharides, the polysaccharides (cellulose and starch), and glycogen.

Glucose is a mixture of α- and β-anomers, primarily the α-anomer. The optical rotation of the α-anomer is +112.2° (c = 10% in water, 20 °C ) and the β-anomer is +18.7° (c = 10% in water, 20 °C). When D-glucose is dissolved in water, the optical rotation gradually changes (mutarotates) with time and approaches a final equilibrium value of +52.7° (c = 10%, 20 °C) due to the formation of an equilibrium mixture consisting of approximately one-third α- and two-thirds β-D-glucose.[2]

Normal human blood contains 0.08-0.1% glucose.[2] Small amounts of glucose (also hydrogen peroxide or glucose oxidase) can be measured using luminol as a substrate with horseradish peroxidase.[3]

Precautions and Disclaimer
For Laboratory Use Only. Not for drug, household or other uses.

Preparation Instructions
One gram of glucose dissolves in 1.1 ml of water at 25 °C and in 0.18 ml of water at 90 °C.[2]

Storage/Stability
Solutions are sterilized by autoclaving.[4]

References
1. Biochemistry, 2nd ed., Lehninger, A. L., ed., Worth Publishers, Inc. (New York, NY: 1975), p. 253.
2. The Merck Index, 13th Ed., Entry# 4472.
3. Puget, K.. and Michelson, A.M., Microestimation of glucose and glucose oxidase. Biochimie, 58, 757-758 (1976).
4. Martindale The Extra Pharmacopoeia, 29th ed., Reynolds, J. E. F., ed., The Pharmaceutical Press (London, England: 1989), p. 1265.

MES/AJH 11/02

Product Information

Adenosine

Product Number A9251
Storage Temperature 2-8 °C

Product Description
Molecular Formula: $C_{10}H_{13}N_5O_4$
Molecular Weight: 267.2
CAS Number: 58-61-7
Specific Rotation: $-61.7°$ ( 7 mg/100 ml water)[1]
$pK_a$: 3.5 and 12.5.[2]
Extinction Coefficient: $E^{mM}$ = 15.4 (259 nm in 0.01 M $PO_4$, pH 7)[3]

Adenosine is a nucleoside, a purine riboside widely distributed in nature. Adenosine is the product of the degradation of AMP.

Precautions and Disclaimer
For Laboratory Use Only. Not for drug, household or other uses.

Preparation Instructions
Soluble in water (7 mg/ml ).[1]

Storage/Stability
Adenosine readily hydrolyzes in dilute mineral acids to adenine and D-ribose. Nitrous acid causes deamination.[2]

References
1. The Merck Index, 11th ed., Entry# 143
2. Dawson, R.M. C., et al., Data for Biochemical Research, 3rd ed., p. 77., Oxford University Press, New York, (1986).
3. Specifications and Criteria for Biochemical Compounds, 3rd ed., p. 157.

MES/ 8/08

Sigma brand products are sold through Sigma-Aldrich, Inc.
Sigma-Aldrich, Inc. warrants that its products conform to the information contained in this and other Sigma-Aldrich publications. Purchaser must determine the suitability of the product(s) for their particular use. Additional terms and conditions may apply. Please see reverse side of the invoice or packing slip.

Figure 29

SIGMA-ALDRICH

3050 Spruce Street, Saint Louis, MO 63103, USA
Website: www.sigmaaldrich.com
Email USA: techserv@sial.com
Outside USA: eurtechserv@sial.com

Product Specification

Product Name:
L-Glutathione oxidized – PharmaGrade, Manufactured under appropriate controls for use as a raw material in pharma or biopharmaceutical production.

| | |
|---|---|
| Product Number: | G2299 |
| CAS Number: | 27025-41-8 |
| Formula: | $C_{20}H_{32}N_6O_{12}S_2$ |
| Formula Weight: | 612.63 g/mol |
| Storage Temperature: | 2 - 8 °C |

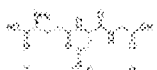

| TEST | Specification |
|---|---|
| Appearance (Color) | White |
| Appearance (Form) | Powder |
| Solubility (Color) | Colorless |
| Solubility (Turbidity) 10 mg/ml, H2O | Clear |
| Infrared spectrum | Conforms to Structure |
| Water (by Karl Fischer) | $\leq 6\ \%$ |
| Nitrogen (anhydrous) | 13.4 - 14.0 % |
| Purity (HPLC) | $\geq 98\ \%$ |
| Impurity Glutathione reduced by HPLC | $\leq 2\ \%$ |
| Recommended Retest Period 3 Years | ------------ |

Specification: PRD.0.ZQ5.10000041806

Sigma-Aldrich warrants, that at the time of the quality release or subsequent retest date this product conformed to the information contained in this publication. The current Specification sheet may be available at Sigma-Aldrich.com. For further inquiries, please contact Technical Service. Purchaser must determine the suitability of the product for its particular use. See reverse side of invoice or packing slip for additional terms and conditions of sale.

HypoThermosol® FRS

Figure 30

Animal Component-Free, Defined Hypothermic (2 - 8°C) Preservation Medium

| Catalog # | 07935 | 100 mL |
| --- | --- | --- |
| | 07934 | 16 x 10 mL |
| | 07936 | 500 mL Bottle |
| | 07945 | 500 mL Bag |

Product Description

HypoThermosol® FRS is an optimized hypothermic (2 - 8°C) preservation media that enables improved and extended preservation of cells, tissues and organs. HypoThermosol® FRS is uniquely formulated to address the molecular-biological response of cells during the hypothermic preservation process. HypoThermosol® FRS includes key ions at concentrations that balance the intracellular state at hypothermic temperatures. Additional components include pH buffers, energy substrates, free radical scavengers, and osmotic/oncotic stabilizers.

- Ready-to-use
- Serum-free, protein-free
- Animal component-free
- cGMP manufactured with USP grade / highest quality components
- FDA master file
- Sterility, endotoxin, and cell-based release testing

Properties

Storage: Store at 2 - 8°C.
Shelf Life: Stable until expiry date (EXP) on label. Product should be protected from prolonged exposure to light.

Please refer to the Safety Data Sheet (SDS) for hazard information.

Product may be shipped at room temperature (15 - 25°C) and should be refrigerated upon receipt.

Handling / Directions For Use

HypoThermosol® FRS is ready to use and contains protective agents.

1. Wipe down outside of HypoThermosol® FRS container with 70% ethanol or isopropanol before opening.
2. Completely replace culture medium with cold (2 - 8°C) HypoThermosol® FRS. Do not warm HypoThermosol® FRS to 37°C.
3. Maintain sample at 2 - 8°C for duration of cold storage. HypoThermosol® FRS is not a culture medium, do not use above 15°C.

At the end of cold storage, simply centrifuge the cells to pellet them and remove HypoThermosol® FRS medium. Replace HypoThermosol® FRS with warmed culture medium of choice and flick the tube gently to resuspend the cells.

THIS PRODUCT IS MANUFACTURED UNDER A cGMP QUALITY MANAGEMENT SYSTEM COMPLIANT TO 21 CFR 820.

Copyright © 2018 by STEMCELL Technologies Inc. All rights reserved including graphics and images. STEMCELL Technologies & Design, STEMCELL Shield Design and Scientists Helping Scientists are trademarks of STEMCELL Technologies Inc. All other trademarks are the property of their respective holders. While STEMCELL has made all reasonable efforts to ensure that the information provided by STEMCELL and its suppliers is correct, it makes no warranties or representations as to the accuracy or completeness of such information.

METHOD OF TRANSPORTING MESENCHYMAL STEM CELLS BY MEANS OF A TRANSPORTING SOLUTION AND A METHOD OF ADMINISTERING STEM CELLS TO WOUNDS

CROSS-REFERENCE TO RELATED APPLICATIONS

The present application claims the benefit of priority of U.S. Provisional Application No. 62/655,198, filed Apr. 9, 2018, the content of which is hereby incorporated by reference it its entirety for all purposes.

FIELD OF THE INVENTION

The present invention relates to a method of transporting a stem cell population, the method comprising transporting the stem cell population contacted with a liquid carrier. In addition, the present invention concerns a method of treating a subject having a disease, the method comprising topically administering a defined mesenchymal stem cell population to the subject, wherein the mesenchymal stem cell population is administered within about 96 hours from the time point the mesenchymal stem cell population has been harvested. Also concerned is a unit dosage comprising about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells of a defined mesenchymal stem cell population.

BACKGROUND OF THE INVENTION

Mesenchymal stem cells isolated from the amniotic membrane of the umbilical cord and their wound healing properties have been first reported in US patent application 2006/0078993 (leading to granted U.S. Pat. Nos. 9,085,755, 9,737,568 and 9,844,571) and the corresponding International patent application WO2006/019357. Since then, the umbilical cord tissue has gained attention as a source of multipotent cells; due to its widespread availability, the umbilical cord and in particular stem cells isolated from the amniotic membrane of the umbilical cord (also referred to as "cord lining stem cells") have been considered as an excellent alternative source of cells for regenerative medicine. See, Jeschke et al. Umbilical Cord Lining Membrane and Wharton's Jelly-Derived Mesenchymal Stem Cells: the Similarities and Differences; The Open Tissue Engineering and Regenerative Medicine Journal, 2011, 4, 21-27.

A subsequent study compared the phenotype, proliferation rate, migration, immunogenicity, and immunomodulatory capabilities of human mesenchymal stem cells (MSCs) derived from the amniotic membrane of the umbilical cord (umbilical cord lining (CL-MSCs), umbilical cord blood (CB-MSCs), placenta (P-MSCs), and Wharton's jelly (WJ-MSCs) (Stubbendorf et al, Immunological Properties of Extraembryonic Human Mesenchymal Stromal Cells Derived from Gestational Tissue, STEM CELLS AND DEVELOPMENT Volume 22, Number 19, 2013, 2619-2629. Stubbendorf et al concluded that extraembryonic gestational tissue-derived MSC populations show a varied potential to evade immune responses as well as exert immunomodulatory effects. The authors also found that CL-MSCs showed the most promising potential for a cell-based therapy, as the cells showed low immunogenicity, but they also showed enhanced proliferative and migratory potential so that future research should concentrate on the best disease models in which CL-MSCs could be administered.

While mesenchymal stem cells of the amniotic membrane can easily be obtained using the protocol as described in US patent application 2006/0078993 and International patent application WO2006/019357, it would be of advantage for clinical trials with these cord lining MSC to have at hand a method that allows to isolate a population of these cord lining MSC's that is highly homogenous and can thus be used for clinical trials.

Such a highly homogenous population of mesenchymal stem cells derived from the amniotic membrane of the umbilical cord has been reported for the first time in co-pending U.S. application Ser. No. 15/725,913, filed 5 Oct. 2018 claiming priority to U.S. provisional application Ser. No. 62/404,582 filed 5 Oct. 2017, the content of both of which is incorporated by reference herein in its entirety) and as well as in co-pending PCT application PCT/SG2017/050500 also filed 5 Oct. 2018 claiming priority to U.S. provisional application No. 62/404,582 filed 5 Oct. 2017 and meets the criteria for mesenchymal stem cells to be used for cellular therapy (also cf. the Experimental Section of U.S. application Ser. No. 15/725,913, Dominici et al, "Minimal criteria for defining multipotent mesenchymal stromal cells. The International Society for Cellular Therapy position statement", Cytotherapy (2006) Vol. 8, No. 4, 315-317, or Sensebe et al, "Production of mesenchymal stromal/stem cells according to good manufacturing practices: a, review", Stem Cell Research & Therapy 2013, 4:66.

Stem cells such as the mesenchymal stem cells as described above are however typically not applied/administered to patients at the site where they are produced. Often a substantial amount of time passes in between the harvesting of cells and their further utilization. There is thus a need for the provision of certain carriers which keep cells viable and healthy for a period of time typically used for transport or storage of cells.

Accordingly, it is an object of the invention to provide a method of transporting/storing stem cells, especially of a population of mesenchymal stem cells from the amniotic membrane of umbilical cord that meets this need.

SUMMARY OF THE INVENTION

This object is accomplished by the methods and the unit dosage having the features of the independent claims.

In a first aspect, the invention provides a method of transporting a stem cell population, the method comprising transporting said stem cell population contacted with a liquid carrier, said liquid carrier comprising
  i) Trolox;
  ii) $Na^+$;
  iii) $K^+$;
  iv) $Cl^-$;
  v) $H_2PO_4^-$;
  vi) HEPES;
  vii) Lactobionate;
  viii) Sucrose;
  ix) Mannitol;
  x) Glucose;
  xi) Dextran-40;
  xii) Adenosine, and
  xiii) Glutathione.

In a second aspect, the invention provides a method of treating a subject having a disease, the method comprising topically administering a mesenchymal stem cell population as described herein to the subject, wherein the mesenchymal stem cell population is administered within about 96 hours from the time point the mesenchymal stem cell population has been harvested.

In a third aspect, the invention provides a unit dosage comprising about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells of a mesenchymal stem cell population as described herein.

In a fourth aspect, the invention provides the use of a liquid carrier for transporting a stem cell population, wherein the liquid carrier comprises
  i) Trolox;
  ii) Na+;
  iii) K+;
  iv) Cl−;
  v) H2PO4−;
  vi) HEPES;
  vii) Lactobionate;
  viii) Sucrose;
  ix) Mannitol;
  x) Glucose;
  xi) Dextran-40;
  xii) Adenosine, and
  xiii) Glutathione.

BRIEF DESCRIPTION OF THE DRAWINGS

The invention will be better understood with reference to the detailed description when considered in conjunction with the non-limiting examples and the drawings, in which:

FIG. 1 shows the technical information sheet of Lonza for Dulbecco's modified eagle medium, including the catalogue number of the DMEM used for the making of the illustrative example of a medium of the invention (PTT-6) in the Experimental Section;

FIG. 2 shows the technical information sheet of Lonza for Ham's F12 medium;

FIG. 3 shows the technical information sheet of Lonza for DMEM:F12 (1:1) medium, including the catalogue number of the DMEM:F12 (1:1) medium used for the making of the illustrative example of a medium of the invention (PTT-6) in the Experimental Section;

FIG. 4 shows the technical information sheet of Life Technologies Corporation for M171 medium, including the catalogue number of the M171 medium used for the making of the illustrative example of a medium of the invention (PTT-6) in the Experimental Section;

FIG. 5 shows the list of ingredients, including their commercial supplier and the catalogue number that have been used in the Experimental Section for the making of the medium PTT-6.

FIG. 6A shows the percentage of isolated mesenchymal cord lining stem cells expressing stem cell markers CD73, CD90 and CD105 after isolation from umbilical cord tissue and cultivation in DMEM/10% FBS, FIG. 6B shows the percentage of isolated mesenchymal cord lining stem cells expressing stem cell markers CD73, CD90 and CD105 after isolation from umbilical cord tissue and cultivation in PTT-4;

FIG. 6C shows the percentage of isolated mesenchymal cord lining stem cells expressing stem cell markers CD73, CD90 and CD105 after isolation from umbilical cord tissue and cultivation in PTT-6.

FIG. 7A shows the percentage of isolated mesenchymal cord lining stem cells that express the stem cell markers CD73, CD90 and CD105 and lack expression of CD34, CD45 and HLA-DR after isolation from umbilical cord tissue and cultivation in PTT-6 medium;

FIG. 7B shows the percentage of isolated bone marrow mesenchymal stem cells that express CD73, CD90 and CD105 and lack expression of CD34, CD45 and HLA-DR.

FIG. 19 datasheet of Trolox available from Tocris.

FIG. 20 shows the datasheet of NaCl available from Sigma Aldrich.

FIG. 21 shows the datasheet of $KH_2PO_4$ available from Sigma Aldrich.

FIG. 22 shows the datasheet for HEPES from Sigma Aldrich.

FIG. 23 shows the product sheet for sodium lactobionate from COMBI-BLOCKS.

FIG. 25 shows the product sheet for mannitol from avantor.

FIG. 26 shows the product sheet for glucose from Sigma Aldrich.

FIG. 28 shows the product sheet for adenosine from Sigma Aldrich.

FIG. 29 shows the product sheet for glutathione from Sigma Aldrich.

FIG. 30 shows the product sheet for HypoThermosol™-FRS (HTS-FRS) from STEMCELL Technologies.

DETAILED DESCRIPTION OF THE INVENTION

Figure 6A:
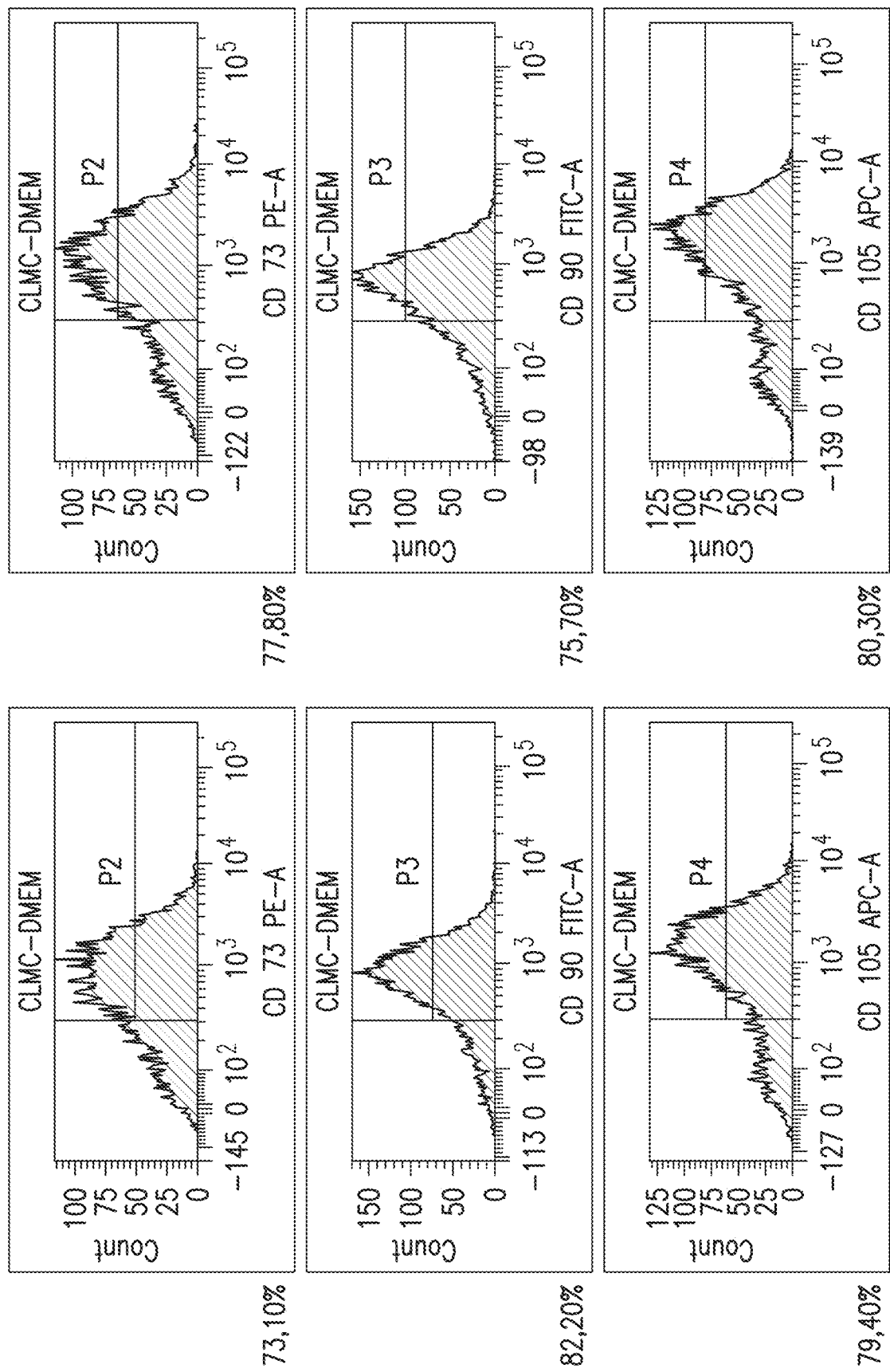
FIGS. 6A-6C show the results of flow cytometry experiments in which mesenchymal stem cells isolated from the umbilical cord have been analysed for the expression of the mesenchymal stem cell markers CD73, CD90 and CD105. For these experiments, mesenchymal stem cells were isolated from umbilical cord tissue by cultivation of the umbilical cord tissue in three different cultivation media, followed by subculturing of the mesenchymal stem cells in the respective medium. The three following culture media were used in these experiments: a) 90% (v/v/DMEM supplemented with 10% FBS (v/v), b) the culture medium PTT-4 described in US patent application 2006/0078993 and the corresponding International patent application WO2006/019357 that consist of 90% (v/v) CMRL1066, and 10% (v/v) FBS (see paragraph [0183] of WO2006/019357 and c) the culture medium of the present invention PTT-6 the composition of which is described herein. In this flow cytometry analysis, two different samples of the cord lining mesenchymal stem cell (CLMC) population were analysed for each of the three used culture media. The results are shown in FIG. 6A to FIG. 6C.

As explained above, in a first aspect the invention is directed to a method of transporting/storing a stem cell population, the method comprising transporting/storing said stem cell population contacted with a liquid carrier, said liquid carrier comprising
i) Trolox;
ii) $Na^+$;
iii) $K^+$;
iv) $Cl^-$;
v) $H_2PO_4^-$;
vi) HEPES;
vii) Lactobionate;
viii) Sucrose;
ix) Mannitol;
x) Glucose;
xi) Dextran-40;
xii) Adenosine, and
xiii) Glutathione.

It has been surprisingly found in the present application that using a liquid carrier as described herein and in particular a liquid carrier such as HypoThermosol™ leads to a superior survival of stem cells compared to other pharmaceutically approved carriers such as e.g. PlasmaLyte®. For example, after 7 days of storage of a mesenchymal stem cell population as described herein in HypoThermosol™ about 70% of the cells were still viable. On the contrary, after 7 days of storage in PlasmaLyte® only about 40% of the cells were still viable (see Examples, when measured with a hemocytometer). Thus, using a liquid carrier as described herein allows the transport/storage of stem cells over a period of time without substantial loss of the viability of cells. In particular, storage in HypoThermosol™ for shorter time period of 3 days or less seems to be especially beneficial, since the stem cells in general secreted more factors than after storage in PlasmaLyte-A as described in the Experimental Section in detail.

When used herein the term 'transport' or 'transporting' any transport is meant. Such transport may be performed with any vehicle, such as car, train, and airplane or by a person carrying/transporting a container comprising the stem cells contacted with the liquid carrier from one place to another place. In one embodiment, transporting is carried out from the place of production of the stem cell population of interest to the place of stem cell administration (for example, the GMP facility in which a stem cell population of interest is produced to the site of administration of the stem cell population, for example, a clinic or a doctor's office). It is however also envisioned that the term 'transporting relates to a storage of cells at the same place for a period of time. For example, stem cells may be stored after harvest until their application to a subject at one place. The container in which the stem cells can be stored or transported can be any container suitable for the method of the present invention.

The transporting/storing can be performed for any period of time. For example, the transporting/storing can be performed for about 7 days or less. It is also envisioned that the transporting/storing can be performed for about 6, 5, 4, 3, 2, 1, day(s) or less. It can thus be that the transporting/storing is performed for about 48 hours or about 24 hours or less.

It is also contemplated that the transporting/storing is performed at any temperature suitable for the method of the present invention. For example, the transporting/storing can be performed at a temperature of about −5° C. to about 15° C. It is therefore also envisioned that the transporting/storing can be performed at a temperature of about 2° C. to about 8° C. The transporting can also be carried out at a temperature of more than about −5° C., more than about −10° C., more than about −15° C., or more than about −20° C. Further it is envisioned that transporting/storing can be performed at a temperature of below 20° C., below 18° C., below 15° C., below 12° C. or below 10° C.

The method of the present invention also envisions that the stem cell population is stored or transported in any suitable concentration. The stem cell population may, for example, be transported/stored in a concentration of about 70 million cells per 1 ml carrier, of about 60 million cells million cells per 1 ml carrier, of about 50 million cells per 1 ml carrier, of about 40 million cells per 1 ml carrier, of about 30 million cells per 1 ml carrier, of about 20 million cells per 1 ml carrier, of about 10 million cells per 1 ml carrier, of about 5 million cells per 1 ml carrier, of about 4 million cells per 1 ml carrier, of about 3 million cells per 1 ml carrier, of about 2 million cells per 1 ml carrier, of about 1 million cells per 1 ml carrier, of about 0.5 million cells per 1 ml carrier, of about 0.1 million cells per 1 ml carrier or of less than 0.1 million cells per 1 ml carrier. Therefore, the stem cell population can be transported/stored in a concentration of about 10 million cells per ml carrier to about 1 million cells per 1 ml carrier.

The method of the present invention concerns the transporting/storing of stem cells. In principle, any stem cell can be used in the method of the present invention. One characterizing feature of stem cells is their ability to self-renew. 'Self-renewal' is the ability to go through numerous cell cycles of cell division while maintaining the undifferentiated state. Methods for testing if a cell has the capacity to self-renew are known to the skilled artisan. For example, self-renewal may be tested by passaging the cells over more than 10, 11, 12, 13, 14, 15, 16, 17, 18, 19, 20, 21, 22, 23, 24, 25, 26, 27, 28, 29, 30 or more passages. Passaging includes splitting of the cells before re-plating them as a single cell suspension. A further characteristic of stem cells is their multipotency or pluripotency as will also be described elsewhere herein. In principle, multipotency or pluripotency can be tested by differentiating said stem cells into different lineages.

In particular, the stem cell population used in the method of the present invention can be an embryonic stem cell population, an adult stem cell population, a mesenchymal stem cell population or an induced pluripotent stem cell population.

As used herein an "embryonic stem cell population" is a "pluripotent stem cell population". A pluripotent cell when referred to herein relates to a cell type having the capacity for self-renewal, and the potential of differentiation into different cell types. Pluripotent stem cells can differentiate into nearly all cells, i.e. cells derived from any of the three primary germ layers: ectoderm, endoderm, and mesoderm. The term pluripotent stem cell also encompasses stem cells derived from the inner cell mass of an early stage embryo known as a blastocyst. Notably, recent advances in embryonic stem cell research have led to the possibility of creating new embryonic stem cell lines without destroying embryos, for example by using a blastomere biopsy-based technique, which does not interfere with the embryo's developmental potential (Klimanskaya (2006) "Embryonic stem cells from blastomeres maintaining embryo viability." Semin Reprod Med. 2013 January; 31(1):49-55). Furthermore, a large number of established embryonic stem cell lines are available in the art. Thus, it is possible to work with embryonic stem cells without the necessity to destroy an embryo. The pluripotent stem cells can be embryonic stem cells, which have not been obtained via the destruction of a human embryo. Thus, the pluripotent stem cells are embryonic stem cells obtained from an embryo, without the destruction of the embryo.

As used herein an "adult stem cell population" is a multipotent stem cell population. A multipotent stem cell population can give rise a restricted number of cell types, therefore they are somatic fate restricted. For example, a neural stem cell can give rise to both neuronal and glial cells. Adult stem cells have the capability to self-renew and may be obtained from any suitable source. For example, adult stem cells may be obtained from bone marrow, peripheral blood, brain, spinal cord, dental pulp, blood vessels, skeletal muscle, epithelia of the skin and digestive system, cornea, retina, liver, or pancreas.

The stem cell population used in the method of the present invention may also be a mesenchymal stem cell population. In this context, it is noted that the culture medium described herein (e.g. PTT-6) allows the isolation of a mesenchymal stem cell population (also referred herein as "mesenchymal stem cells") from the amniotic membrane under conditions that allow cell proliferation of the mesenchymal stem/progenitor cells without differentiation of the mesenchymal stem/progenitor cells. Thus, after isolation of the mesenchymal stem cells from the amniotic membrane as described herein the isolated mesenchymal stem/progenitor cell population has the capacity to differentiate into multiple cell types as described in US patent application 2006/0078993, U.S. Pat. No. 9,085,755, International patent application WO2006/019357, U.S. Pat. No. 8,287,854 or WO2007/046775, for instance. As described in US patent application 2006/0078993, for example, the mesenchymal stem cells of the amniotic membrane of the umbilical cord have a spindle shape, express the following genes: POU5f1, Bmi-1, leukemia inhibitory factor (LIF), and secrete Activin A and Follistatin. The mesenchymal stem cells isolated in the present invention can, for example, be differentiated into any type of mesenchymal cell such as, but not limited to, adipocytes, skin fibroblasts, chondrocytes, osteoblasts, tenocytes, ligament fibroblasts, cardiomyocytes, smooth muscle cells, skeletal muscle cells, mucin producing cells, cells derived from endocrine glands such as insulin producing cells (for example, β-islet cells) or neurectodermal cells. The stem cells isolated in accordance with the method described herein can be differentiated in vitro in order to subsequently use the differentiated cell for medical purposes. An illustrative example of such an approach is the differentiation of the mesenchymal stem ells into insulin producing β-islet cells which can then be administered, for example by implantation, to a patient that suffers from an insulin deficiency such as diabetes mellitus (cf. also WO2007/046775 in this respect). Alternatively, the mesenchymal stem cells described herein can be used in their undifferentiated state for cell-based therapy, for example, for wound healing purposes such as treatment of burns or chronic diabetic wounds. In these therapeutic applications the mesenchymal stem cells of the invention can either serve to promote wound healing by interacting with the surrounding diseased tissue or can also differentiate into a respective skin cell (cf., again WO2007/046775, for example).

In this context, it is noted that the mesenchymal stem cell population described herein can be isolated and cultivated (i.e. are derived) from any umbilical cord tissue as long as the umbilical cord tissue contains the amniotic membrane (which is also referred to as "cord lining"). Accordingly, the mesenchymal stem cell population can be isolated from (pieces of) the entire umbilical cord as described in the Experimental section of the present application. This umbilical cord tissue may thus contain, in addition to the amniotic membrane, any other tissue/component of the umbilical cord. As shown, for example, in FIG. 16 of US patent application 2006/0078993 or International patent application WO2006/019357, the amniotic membrane of the umbilical cord is the outermost part of the umbilical cord, covering the cord. In addition, the umbilical cord contains one vein (which carries oxygenated, nutrient-rich blood to the fetus) and two arteries (which carry deoxygenated, nutrient-depleted blood away from the fetus). For protection and mechanical support these three blood vessels are embedded in Wharton's jelly, a gelatinous substance largely of mucopolysaccharides. Accordingly, the umbilical cord tissue used herein can also comprise this one vein, the two arteries and the Wharton's jelly. The use of such an entire (intact) section of the umbilical cord has the advantage that the amniotic membrane does not need to be separated from the other components of the umbilical cord. This reduces the isolation steps and thus makes the method described herein, simpler, faster, less error prone and more economical—which are all important aspects for the GMP production that is necessary for therapeutic application of the mesenchymal stem cells. The isolation of the mesenchymal stem cells can thus start by tissue explant, which may be followed by subsequent subculturing (cultivation) of the isolated mesenchymal stem cells if greater amounts of the mesenchymal stem cells are desired, for example, for use in clinical trials. Alternatively, it is also possible to first separate the amniotic membrane from the other components of the umbilical cord and isolate the mesenchymal cord lining stem cells from the amniotic membrane by cultivation of the amniotic membrane in a culture medium e.g. PTT-6. This cultivation can also be carried out by tissue explant, optionally followed by subculturing of the isolated mesenchymal stem cells. In this context, the term "tissue explant" or "tissue explant method" is used in its regular meaning in the art to refer a method in which a tissue, once being harvested, or a piece of the tissue is being placed in a cell culture dish containing culture (growth) medium and by which over time, the stem cells migrate out of the tissue onto the surface of the dish. These primary stem cells can then be further expanded and transferred into fresh dishes through micropropagation (subculturing) as also described here. In this context, it is noted that in terms of production of the cells for therapeutic purposes, in the first step of isolating the amniotic membrane mesenchymal stem cells from the umbilical cord, a master cell bank of the isolated mesenchymal stem cells is obtained, while with the subsequent subculturing, a working cell bank can be obtained. In particular embodiments, the stem cell population thus is a mesenchymal stem cell population.

The mesenchymal stem cell population may be isolated from the amniotic membrane of the umbilical cord by a method comprising cultivating umbilical cord tissue in a culture medium comprising DMEM (Dulbecco's modified eagle medium), F12 (Ham's F12 Medium), M171 (Medium 171) and FBS (Fetal Bovine Serum). Using such a medium provides for the isolation of a mesenchymal stem cell population from the amniotic membrane of the umbilical cord of which more than 90%, or even 99% or more of the cells are positive for the three mesenchymal stem cell markers CD73, CD90 and CD105 while at the same these stem cells lack expression of CD34, CD45 and HLA-DR (see the Experimental Section), meaning 99% or even more cells of this population express the stem cell markers CD73, CD90 and CD105 while not expressing the markers CD34, CD45 and HLA-DR. Such an extremely homogenous and well defined cell population has been reported for the first time in co-pending U.S. application Ser. No. 15/725,913, filed 5 Oct. 2018 claiming priority to U.S. provisional application Ser. No. 62/404,582 filed 5 Oct. 2017, the content of both of which is incorporated by reference herein in its entirety) and as well as in co-pending PCT application PCT/SG2017/050500 also filed 5 Oct. 2018 claiming priority to U.S. provisional application No. 62/404,582 filed 5 Oct. 2017 and is the ideal candidate for clinical trials and cell based therapies since, this stem cell population for example, fully meets the criteria generally accepted for human mesenchymal stem cells to be used for cellular therapy as defined, for example, by Dominici et al, "Minimal criteria for defining multipotent mesenchymal stromal cells. The International Society for Cellular Therapy position statement", Cytotherapy (2006) Vol. 8, No. 4, 315-317, Sensebe et al, "Production of mesenchymal stromal/stem cells according to good manufacturing practices: a, review", Stem Cell Research & Therapy 2013, 4:66), Vonk et al., Stem Cell Research & Therapy (2015) 6:94, or Kundrotas Acta Medica Lituanica. 2012. Vol. 19. No. 2. P. 75-79. Also, using a bioreactor such as a Quantum Cell Expansion System, it is possible to obtain high numbers of mesenchymal stem cells such as 300 to 700 million mesenchymal stem cells per run (see also the Experimental Section). Thus, the present invention allows transporting/storing amounts of stem cells that are needed for therapeutic applications, such as their use in wound healing, in a cost efficient manner. In addition, all components used for making the culture medium of the present invention are commercially available in GMP quality. Accordingly, the present invention opens the route to transport/store a GMP produced and highly homogenous mesenchymal stem cell population from the amniotic membrane of the umbilical cord.

Thus, in some embodiments the mesenchymal stem cell population is an isolated mesenchymal stem population of the amniotic membrane of the umbilical cord. It is further envisioned that at least about 90% or more cells of the isolated mesenchymal stem cell population express each of the following markers: CD73, CD90 and CD105. For example, at least about 91% or more, about 92% or more, about 93% or more, about 94% or more, about 95% or more, about 96% or more, about 97% or more, about 98% or more about 99% or more cells of the isolated mesenchymal stem cell population express each of CD73, CD90 and CD105. Additionally or alternatively, at least about 90% or more, about 91% or more, about 92% or more, about 93% or more, about 94% or more, about 95% or more, about 96% or more, about 97% or more, about 98% or more about 99% or more of the isolated mesenchymal stem cells lack expression of the following markers: CD34, CD45 and HLA-DR (Human Leukocyte Antigen—antigen D Related).

The marker CD73 is known to the skilled person. In this regard CD73 refers to cluster of differentiation 73 also known as 5'-nucleotidase (5'-NT) or ecto-5'-nucleotidase. The sequence of the human CD73 protein may have the sequence of SEQ ID NO. 1. The marker CD90 is known to the skilled person. In this regard CD90 refers to Cluster of Differentiation 90 also known as Thymocyte differentiation antigen 1 (Thy-1). The sequence of the human CD90 protein may have the sequence of SEQ ID NO: 2. The marker CD105 is known to the skilled person. CD105 is also known as Endoglin (ENG). The sequence of the human CD105 protein may have the sequence of SEQ ID NO: 3.

If a mesenchymal stem cell population of the invention (in particular a population of the mesenchymal stem cells of which at least about 98% or 99% or express each of the markers CD73, CD90 and CD105 and lack expression of each of the markers: CD34, CD45 and HLA-DR) is used for clinical trials or as an approved therapeutic, a cell population of the working cell bank will typically be used for this purpose. As explained, the mesenchymal stem cell population may lack expression of the following markers: CD34, CD45 and HLA-DR. In this context it is noted that the marker CD34, CD45 and HLA-DR are known to the skilled person. The human CD34 protein may have the sequence of SEQ ID NO. 4. The human CD45 protein may have the sequence of SEQ ID NO: 5. The human HLA-DR protein may have the sequence of SEQ ID NO: 6.

Both the stem cell population of the isolation step (which may make up the master cell bank) and the stem cell population of the subculturing step (which may make up the working cell bank) can, for example, be stored in cryopreserved form.

As mentioned above, the present method of isolating mesenchymal stem cells from the amniotic membrane of umbilical cord has the advantage that all components used in the culture medium of the invention are available in GMP quality and thus provide the possibility to isolate the mesenchymal stem cells under GMP conditions for subsequent therapeutic administration.

Thus, the stem cell population can also be an induced pluripotent stem cell population. "Induced pluripotent stem cells", as used herein, refer to adult somatic cells that have been genetically reprogrammed to an embryonic stem cell-like state by being forced to express genes and factors important for maintaining the defining properties of embryonic stem cells. Thus, induced pluripotent stem cells can be derived/generated from a non-pluripotent cell.

Induced pluripotent stem cells are an important advancement in stem cell research, as they allow obtaining pluripotent stem cells without the use of embryos. Mouse iPSCs were first reported in 2006 (Takahashi, K; Yamanaka, S (2006). "Induction of pluripotent stem cells from mouse embryonic and adult fibroblast cultures by defined factors". Cell 126 (4): 663-76), and human iPSCs (hiPSCs) were first reported in 2007 (Takahashi et al. (2007) "Induction of pluripotent stem cells from adult human fibroblasts by defined factors." Cell; 131(5):861-72). Mouse iPSCs demonstrate important characteristics of pluripotent stem cells, including expression of stem cell markers, forming tumors containing cells from all three germ layers, and being able to contribute to many different tissues when injected into mouse embryos at a very early stage in development. Human iPSCs also express stem cell markers and are capable of generating cells characteristic of all three germ layers. Such stem cell markers can include Oct3/4, Sox2, Nanog, alkaline phosphatase (ALP) as well as stem cell-specific antigen 3 and 4 (SSEA3/4). Also, the chromatin methylation patterns of iPSC are similar to that of embryonic stem cells (Tanabe, Takahashi, Yamanaka (2014) "Induction of pluripotency by defined factors." Proc. Jpn. Acad., 2014, Ser. B 90).

In addition, iPSCs are able to self-renew in vitro and differentiate into all three germ layers. The pluripotency or the potential to differentiate into different cell types of iPSC can tested, e.g., by in vitro differentiation into neural or glia cells or the production of germline chimeric animals through blastocyst injection.

Methods for the generation of human induced pluripotent stem cells are well known to the skilled person and for example described in WO2009115295, WO2009144008 or EP2218778. Thus, the skilled artisan can obtain an iPSC by any method. In principle, induced pluripotent stem cells may be obtained from any adult somatic cell (of a subject). Exemplary somatic cells include peripheral blood Mononuclear Cells (PBMCs) from blood or fibroblasts obtained from skin tissue biopsies.

The method of the present invention includes that the stem cell population as described herein is contacted with a liquid carrier. It is envisioned that in the method of the present invention the stem cell population as described herein is contacted with the carrier before transporting/storing. Additionally or alternatively, the stem cell population is contacted with the carrier after its harvest. How harvesting can be performed is described in detail elsewhere herein as well as in the Experimental Section. For example, the stem cell population can be contacted with the carrier about 0 minutes, about 1 minute, about 5 minutes, about 10 minutes, about 30 minutes, about 45 minutes, about 60 minutes or a longer time after its harvest.

Harvesting can comprise separating the stem cell population from culture medium e.g. from PTT-6. Suitable techniques for such separation are known to the skilled person. For example, separating can be performed by centrifuging the stem cells within a culture medium and decanting the culture medium.

The stem cell population is contacted with a liquid carrier, wherein the liquid carrier comprises
  i) Trolox;
  ii) $Na^+$;
  iii) $K^+$;
  iv) $Cl^-$;
  v) $H_2PO_4^-$;
  vi) HEPES;
  vii) Lactobionate;
  viii) Sucrose;
  ix) Mannitol;
  x) Glucose;
  xi) Dextran-40;
  xii) Adenosine, and
  xiii) Glutathione.

By "Trolox" is meant 6-hydroxy-2,5,7,8-tetramethylchroman-2-carboxylic acid of CAS Number 53188-07-1. It is a water-soluble analog of vitamin E and is suggested to reduce oxidative stress or damage. FIG. 19 shows the datasheet of Trolox available from Tocris. It also commercially available from Sigma Aldrich (product number: 238813).

Both of $Na^+$ and $Cl^-$ are well known ions. The skilled person knows how to obtain these. For example, these ions may be added to the carrier as a NaCl salt. NaCl in GMP quality can be obtained from Sigma Aldrich. FIG. 20 shows the datasheet of NaCl available from Sigma Aldrich.

$K^+$ and $H_2PO_4^-$ (dihydrogen phosphate) are also well known to the skilled person. It may be used e.g. as a $KH_2PO_4$ obtainable from SigmaAldrich. FIG. 21 shows the datasheet of $KH_2PO_4$ available from Sigma Aldrich.

HEPES also named 4-(2-Hydroxyethyl)piperazine-1-ethanesulfonic acid (CAS Number 7365-45-9) is commonly used as a zwitterionic organic chemical buffering agent. The person skilled in the art also knows where to obtain HEPES, which is commercially available. For example, she/he may obtain it from Sigma Aldrich; the corresponding data sheet shown in FIG. 22.

Lactobionate is the carboxylate anion of lactobionic acid. Lactobionic acid (4-O-β-galactopyranosyl-D-gluconic acid) is a sugar acid. Lactobionate can be used in different ways. When used as potassium lactobionate it can e.g. provide osmotic support and prevent cell swelling and when combined with sodium it may have a preservative function. Alternatively, mineral salts of lactobionic acid can be used for mineral supplementation. For pharmaceutic applications, often the antibiotic erythromycin can inter alia be used as the salt erythromycin lactobionate. The skilled person also knows where to obtain lactobionate e.g. sodium lactobionate (Cas Number: 27297-39-8), namely from e.g. COMBI-BLOCKS, see product sheet in FIG. 23.

Figure 24:
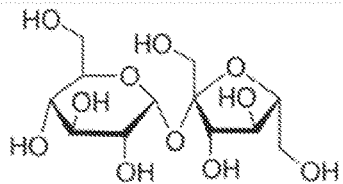
FIG. 24 shows the product sheet for sucrose from Sigma Aldrich.
Figure 24:

Sucrose, also known as D-Glc-(1→2)-β-D-Fru, α-D-glucopyranosyl β-D-fructofuranoside, β-D-fructofuranosyl-α-D-glucopyranoside, D(+)-saccharose or sugar (CAS Number 57-50-1) can as the other substances be commercially obtained and the skilled person knows where to buy it as well. The corresponding product sheet for sucrose from Sigma Aldrich is shown in FIG. 24.

Mannitol is a type of sugar alcohol (CAS Registry Number: 69-65-8). The person skilled in the art knows how to obtain mannitol. For example, it may be obtained from Avantor. The respective product sheet is shown in FIG. 25.

Glucose (CAS Number: 50-99-7) is also well known to the skilled person and commercially available. A respective product sheet from Sigma Aldrich is shown in FIG. 26.

Figure 27:
FIG. 27 shows the product sheet for Dextran-40 from Sigma Aldrich.
Figure 27:
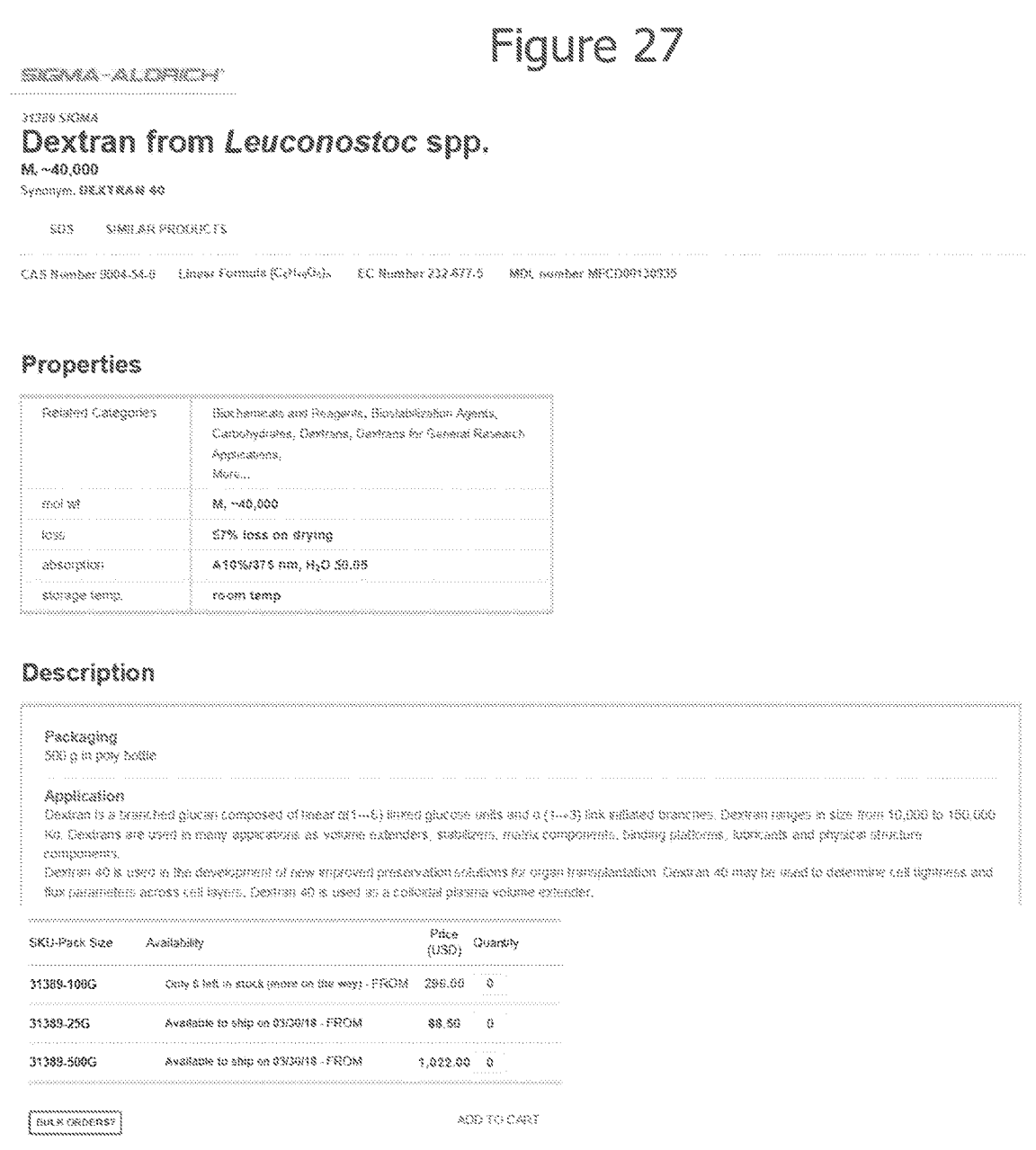

Dextran is a branched glucan composed of linear α (1→6) linked glucose units and α (1→3) link initiated branches. Dextran ranges in size from 10,000 to 150,000 Kd. Dextrans are used in many applications as volume extenders, stabilizers, matrix components, binding platforms, lubricants and physical structure components. Dextran 40 (CAS Number: 9004-54-0) as used in the carrier described herein is typically used in the development of new improved preservation solutions for organ transplantation. Dextran 40 may be used to determine cell tightness and flux parameters across cell layers. Dextran 40 can also be used as a colloidal plasma volume extender. Dextran-40 is commercially available and can inter alia be obtained from Sigma. Aldrich (product sheet shown in FIG. 27).

Adenosine (CAS Number 58-61-7) is a purine nucleoside composed of a molecule of adenine attached to a ribose sugar molecule (ribofuranose) moiety via a β-$N_9$-glycosidic bond. Adenosine is commercially available inter alia from Sigma-Aldrich (the corresponding product sheet is shown in FIG. 28).

Glutathione is also known as (2S)-2-Amino-4-{[(1R)-1-[(carboxymethyl)carbamoyl]-2-sulfanylethyl]carbamoyl}butanoic acid. This component is commercially available and can inter alia be obtained from Sigma Aldrich (corresponding product sheet shown in FIG. 29).

In principle any liquid carrier comprising the substances as listed in above can be used in the method of the present invention. The carrier is a liquid carrier. Thus, it is possible that the substances as listed in i)-xiii) are dissolved in a liquid to form a solution/suspension. The liquid may be any suitable liquid. For example, the liquid can be a culture medium, water, buffer, or the like.

The carrier may additionally comprise further pH buffers, energy substrates, free radical scavengers, and osmotic/oncotic stabilizers—all known to the skilled person. Furthermore, the liquid carrier may be serum-free and/or protein-free. The liquid carrier may not comprise a dipolar aprotic solvent such as for example DMSO. In particular, the liquid carrier may be a carrier as described in WO 2010/064054. The carrier may be HypoThermosol™ or Hypo-Thermosol™-FRS (HTS-FRS). HypoThermosol™-FRS (HTS-FRS) can be purchased from STEMCELL Technologies (according to the respective product sheet shown in FIG. 30).

It is further envisioned that the carrier is a transport/storage medium or an excipient. A transport/storage medium, may be a natural medium, which consists solely of naturally occurring biological fluids, which additionally comprise substances as listed in i)-xiii) as described herein. The medium can also be one comprising substances as listed in i)-xiii) as described herein and addition of (further) nutrients (both organic and inorganic), vitamins, salts, $O_2$ and $CO_2$ gas phases, serum proteins, carbohydrates, and/or cofactors. In particular embodiments the medium is serum and/or protein free.

The carrier may also be an excipient. An "excipient" is a substance formulated alongside the active ingredient of a medication. In the present method the active ingredient is the stem cell population.

The carrier may further comprise biocompatible scaffolds or microcarriers. The scaffolds or microcarriers can, for example, be biodegradable polymeric substances, most preferably poly(D,L lactic-co-glycolic acid) (PLGA)). Alternatively, the scaffolds or micro-carriers may be smooth, macroprorous or microporous structures comprising substances including poly-L-lactide (PLLA), collagen, fibronectin, glycosaminoglycans (GAGs), fibrin, starch, cellulose arabinogalactan (larch gum), alginic acid, agar, carrageenan, chitin, hyaluronic acid, dextran, gellan gum, pullulan, hydroxyapatite, polyhydroxyalkanoates (PHAs), hydrogels or other self-assembling materials such as peptide based nanostructured fibrous scaffolds;

In principle any amount of stem cells can be contacted with any amount of liquid carrier. In this regard the contacting can be performed by suspending the stem cell population in a density of about 70 million/ml, of about 60 million/ml, of about 50 million/ml, of about 40 million/ml, of about 30 million/ml, of about 20 million/ml, of about 10 million/ml, of about 5 million/ml, of about 4 million/ml, of about 3 million/ml, of about 2 million/ml, of about 1 million/ml, of about 0.5 million/ml, of about 0.1 million/ml or of less than 0.1 million cells in 1 ml of the carrier. In some embodiments, the contacting is performed by suspending the stem cell population in a density of about 10 million/1 ml carrier.

After contacting the stem cell population with the carrier, the stem cells contacted with the carrier can be aliquoted into vials in a volume of about 50 ml, of about 20 ml, of about 10 ml, of about 5 ml, of about 4 ml, of about 3 ml, of about 2 ml, of about 1 ml, of about 0.5 ml, of about 0.25 ml or of less than 0.25 ml carrier. For example, the stem cells that have been contacted with the carrier can be aliquoted into vials in a volume of about 1 ml.

It is further envisioned that the method of the present invention does not comprise a thawing or freezing step. This may include that after their harvest the stem cell population is transported/stored without the need to freeze and thaw the stem cell population.

The carrier used in the method of transporting/storing the stem cell population as described herein is particularly suited for this purpose. One advantage of this carrier is that substantially all stem cells transported/stored therein remain viable. A "viable cell" is a cell able to live. The person skilled in the art knows how to detect viable cells. One such method is staining cells with the dye Trypan blue. Viable cells do not stain positive with Trypan blue.

In this regard, in the method of the present invention at most about 50%, about 40%, about 30%, about 20%, about 10% or less than about 10% of the stem cells of the population may die during transporting/storing compared to the number/amount of viable stem cells before transporting/storing.

The method of the present invention also contemplates that the stem cell population has any cell diameter after transporting/storage. The person skilled in the art knows how to measure the diameter of a cell. For example, cell size/diameter may be determined by capturing a microscope image and using secondary software to measure the diameter of the cell. Most of the stem cells in the stem cell population can therefore have a cell diameter between about 9 µm and about 20 µm after transporting/storage. It is also envisioned that most of the stem cells in the stem cell population have a cell diameter between about 12 µm and about 16 µm after transporting.

The stem cells transported/stored in the carrier as described herein secrete the same proteins/factors as viable stem cells. For example, the method of the present invention contemplates that after transport/storage the (mesenchymal) stem cell population may secrete about as much TGFbeta 1 as before transporting/storage. TGFbeta 1 (Transforming growth factor beta, TGF-β1) is known to the skilled person and may comprise the sequence as shown in SEQ ID NO. 7. Additionally or alternatively, after transporting/storing the (mesenchymal) stem cell population may secrete about as much VEGF (Vascular endothelial growth factor), PDGF-AA (Platelet-derived growth factor subunit AA), Ang-1 (Angiogenin-1), and/or HGF (Hepatocyte growth factor) as before transporting/storing. All of VEGF, PDGF-AA, Ang-1, and/or HGF are known to the skilled person for their involvent in wound healing. In particular, VEGF may comprise a sequence as shown in SEQ ID NO. 8, PDGF-AA may have a sequence as shown in SEQ ID NO. 9, Ang-1 may have a sequence as shown in SEQ ID NO. 10 while HGF may have a sequence as shown in SEQ ID NO. 11. Additionally or alternatively, essentially no PDGF-BB and/or IL-10 is detected before and/or after transporting. Both of PDGF-BB (Platelet-derived growth factor subunit BB) and/or IL-10 (interleukin-10) are also known to the skilled person. PDGF-BB may comprise a sequence as shown in SEQ ID NO. 12 while IL-10 may comprise a sequence as shown in SEQ ID NO: 13. The secretion of these factors can be determined with any suitable method, for example, by measuring the amount of protein (i.e., for example, PDGF-AA, PDGF-BB, VEGF, IL-10, Ang-1, HGF or TGFβ1) that the stem cells secrete into the carrier. The amount of protein can be measured by commercially available antibodies/immunoassays in an automated fashion, using, for example a system such as the FLEXMAP 3D system (Luminex Corporation, Austin, Tex., USA). In this context, it is noted that involvement of the proteins Angiopoietin 1 (Ang-1), TGF-β1, VEGF, and HGF in the wound healing process is known to the person skilled in the art. For the involvement of Angiopoietin 1 in wound healing, see, for example, Li et al. Stem Cell Research & Therapy 2013, 4:113 "Mesenchymal stem cells modified with angiopoietin-1 gene promote wound healing". For the involvement of Hepatocyte Growth Factor (HGF) in wound healing, in particular healing of chronic/non healing wounds see for example, Yoshida et al., "Neutralization of Hepatocyte Growth Factor Leads to Retarded Cutaneous Wound Healing Associated with Decreased Neovascularization and Granulation Tissue Formation J. Invest. Dermatol. 120:335-343, 2003, Li, Jin-Feng et al. "HGF Accelerates Wound Healing by Promoting the Dedifferentiation of Epidermal Cells through β 1-Integrin/ILK Pathway." BioMed Research International 2013 (2013): 470418 or Conway et al, "Hepatocyte growth factor regulation: An integral part of why wounds become chronic". Wound Rep Reg (2007) 15 683-692. For the involvement of Vascular Endothelial Growth Factor (VEGF) in wound healing, in particular healing of chronic/non-healing wounds, see for example Froget et al., Eur. Cytokine Netw., Vol. 14, March 2003, 60-64 or Bao et al., "The Role of Vascular Endothelial Growth Factor in Wound Healing" J Surg Res. 2009 May 15; 153(2): 347-358.

For the involvement of Transforming Growth Factor Beta (including TGF-β1, TGF-β2, and TGF-β3) in wound healing, in particular healing of chronic/non-healing wounds see for example, Ramirez et al. "The Role of TGFb Signaling in Wound Epithelialization" Advances In Wound Care, Volume 3, Number 7, 2013, 482-491 or Pakyari et al., Critical Role of Transforming Growth Factor Beta in Different Phases of Wound Healing, Advances In Wound Care, Volume 2, Number 5, 2012, 215-224.

Turning now to the culture medium used in the present invention, the culture medium may comprise, for the isolation or cultivation of the mesenchymal cord lining stem cells, DMEM in a final concentration of about 55 to 65% (v/v), F12 in a final concentration of about 5 to 15% (v/v), M171 in a final concentration of about 15 to 30% (v/v) and FBS in a final concentration of about 1 to 8% (v/v). The value of "% (v/v)" as used herein refers to the volume of the individual component relative to the final volume of the culture medium. This means, if DMEM is, for example, present in the culture medium at a final concentration of about 55 to 65% (v/v), 1 liter of culture medium contains about 550 to 650 ml DMEM.

In other embodiments, the culture medium may comprise DMEM in a final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v). In further embodiments, the culture medium may comprise DMEM in a final concentration of about 61.8% (v/v), F12 in a final concentration of about 11.8% (v/v), M171 in a final concentration of about 23.6% (v/v) and FBS in a final concentration of about 2.5% (v/v).

In addition to the above-mentioned components, the culture medium may comprise supplements that are advantageous for cultivation of the mesenchymal cord lining stem cells. The culture medium of the present invention may, for example, comprise Epidermal Growth Factor (EGF). If present, EGF may be present in the culture medium in a final concentration of about 1 ng/ml to about 20 ng/ml. In some of these embodiments, the culture medium may comprise EGF in a final concentration of about 10 ng/ml.

The culture medium may also comprise insulin. If present, insulin may be present in a final concentration of about 1 µg/ml to 10 µg/ml. In some of these embodiments, the culture medium may comprise Insulin in a final concentration of about 5 g/ml.

The culture medium may further comprise at least one of the following supplements: adenine, hydrocortisone, and 3,3',5-Triiodo-L-thyronine sodium salt (T3). In such embodiments, the culture medium may comprise all three of adenine, hydrocortisone, and 3,3',5-Triiodo-L-thyronine sodium salt (T3). In these embodiments, the culture medium may comprise adenine in a final concentration of about 0.05 to about 0.1 µg/ml, hydrocortisone in a final concentration of about 1 to about 10 µg/ml and/or 3,3',5-Triiodo-L-thyronine sodium salt (T3) in a final concentration of about 0.5 to about 5 ng/ml.

In one embodiment, the mesenchymal stem cells are cultured in PTT6 medium to obtain the highly purified mesenchymal stem cell population described and used herein. In this context it is noted that PTT6 medium as described herein is obtained by mixing to obtain a final volume of 500 ml culture medium:
  i. 250 ml of DMEM
  ii. 118 ml M171
  iii. 118 ml DMEM/F12
  iv. 12.5 ml Fetal Bovine Serum (FBS) to reach a final concentration of 2.5% (v/v)
  v. EGF in a final concentration of 10 ng/ml
  vi. Insulin in a final concentration of 5 µg/ml.
  vii. Insulin 0.175 ml (final concentration of 5 µg/ml)

By "DMEM" is meant Dulbecco's modified eagle medium which was developed in 1969 and is a modification of basal medium eagle (BME) (cf. FIG. 1 showing the data sheet of DMEM available from Lonza). The original DMEM formula contains 1000 mg/L of glucose and was first reported for culturing embryonic mouse cells. DMEM has since then become a standard medium for cell culture that is commercially available from various sources such as ThermoFisher Scientific (catalogue number 11965-084), Sigma Aldrich (catalogue number D5546) or Lonza, to new only a few suppliers. Thus, any commercially available DMEM can be used in the present invention. In preferred embodiments, the DMEM used herein is the DMEM medium available from Lonza under catalog number 12-604F. This medium is DMEM supplemented with 4.5 g/L glucose and L-glutamine. In another preferred embodiment the DMEM used herein is the DMEM medium of Sigma Aldrich catalogue number D5546 that contains 1000 mg/L glucose, and sodium bicarbonate but is without L-glutamine.

By "F12" medium is meant Ham's F12 medium. This medium is also a standard cell culture medium and is a nutrient mixture initially designed to cultivate a wide variety of mammalian and hybridoma cells when used with serum in combination with hormones and transferrin (cf. FIG. 2, showing the data sheet of Ham's F12 medium from Lonza). Any commercially available Ham's F12 medium (for example, from ThermoFisher Scientific (catalogue number 11765-054), Sigma Aldrich (catalogue number N4888) or Lonza, to name only a few suppliers) can be used in the present invention. In preferred embodiments, Ham's F12 medium from Lonza is used.

By "DMEM/F12" or "DMEM:F12" is meant a 1:1 mixture of DMEM with Ham's F12 culture medium (cf. FIG. 3 showing the data sheet for DMEM: F12 (1:1) medium from Lonza). DMEM/F12 (1:1) medium is a widely used basal medium for supporting the growth of many different mammalian cells and is commercially available from various suppliers such as ThermoFisher Scientific (catalogue number 11330057), Sigma Aldrich (catalogue number D6421) or Lonza. Any commercially available DMEM:F12 medium can be used in the present invention. In preferred embodiments, the DMEM:F12 medium used herein is the DMEM/F12 (1:1) medium available from Lonza under catalog number 12-719F (which is DMEM: F12 with L-glutamine, 15 mM HEPES, and 3.151 g/L glucose).

By "M171" is meant culture medium 171, which has been developed as basal medium for the culture and growth of normal human mammary epithelial cells (cf. FIG. 4 showing the data sheet for M171 medium from Life Technologies Corporation). This basal medium is widely used and is commercially available from suppliers such as ThermoFisher Scientific or Life Technologies Corporation (catalogue number M171500), for example. Any commercially available M171 medium can be used in the present invention. In preferred embodiments, the M171 medium used herein is the M171 medium available from Life Technologies Corporation under catalogue number M171500.

By "FBS" is meant fetal bovine serum (that is also referred to as "fetal calf serum"), i.e. the blood fraction that remains after the natural coagulation of blood, followed by centrifugation to remove any remaining red blood cells. Fetal bovine serum is the most widely used serum-supplement for in vitro cell culture of eukaryotic cells because it has very low level of antibodies and contains more growth factors, allowing for versatility in many different cell culture applications. The FBS is preferably obtained from a member of the International Serum Industry Association (ISIA) whose primary focus is the safety and safe use of serum and animal derived products through proper origin traceability, truth in labeling, and appropriate standardization and oversight. Suppliers of FBS that are ISIA members include Abattoir Basics Company, Animal Technologies Inc., Biomin Biotechnologia LTDA, GE Healthcare, Gibco by Thermo Fisher Scientific and Life Science Production, to mention only a few. In currently preferred embodiments, the FBS is obtained from GE Healthcare under catalogue number A15-151.

As mentioned above, a method of making a culture medium for isolating the mesenchymal stem cell population used in the invention comprises mixing to obtain a final volume of 500 ml culture medium:
  i. 250 ml of DMEM
  ii. 118 ml M171
  iii. 118 ml DMEM/F12
  iv. 12.5 ml Fetal Bovine Serum (FBS) to reach a final concentration of 2.5% (v/v).

As explained above, DMEM/F12 medium is a 1:1 mixture of DMEM and Ham's F12 medium. Thus, 118 ml DMEM/F12 medium contain 59 ml DMEM and 59 ml F12. Accordingly, when using this method of making a culture medium, the final concentrations (v/v) with 500 ml total volume are as follows:
  DMEM: 250 ml+59 ml=309 ml, corresponds to 309/500=61.8% (v/v)
  M171: 118 ml, corresponds to 118/500=23.6% (v/v)
  F12: 59 ml, corresponds to 59/500=11.8% (v/v).

Embodiments of this method of making a culture medium further comprise adding
  v. 1 ml EGF stock solution (5 µg/ml) to achieve a final EGF concentration of 10 ng/ml, and
  vi. Insulin 0.175 ml stock solution (14.28 mg/ml) to achieve a final insulin concentration of 5 µg/ml.

It is noted here that in these embodiments, the above-mentioned volumes of these components i. to vi. will result in a final volume of 499.675 ml culture medium. If no further components are added to the culture medium, the remaining 0.325 ml (to add up to a volume of 500 ml) can, for example, be any of components i. to iv., that means either DMEM, M171, DMEM/F12 or FBS. Alternatively, the concentration of the stock solution of EGF or Insulin can of course be adjusted such that the total volume of the culture medium is 500 ml. In addition, it is also noted that components i. to iv. do not necessarily have to be added in the order in which they are listed but it is of course also possible to use any order to mix these components to arrive at the culture medium of the present invention. This means, that for example, M171 and DMEM/F12 can be mixed together and then combined with DMEM and FBS to reach final concentrations as described here, i.e. a final concentration of DMEM of about 55 to 65% (v/v), a final concentration of F12 of about 5 to 15% (v/v), a final concentration of M171 of about 15 to 30% (v/v) and a final concentration of FBS of about 1 to 8% (v/v).

In other embodiments, the method further comprises adding to DMEM a volume of 0.325 ml of one or more of the following supplements: adenine, hydrocortisone, 3,3',5-Triiodo-L-thyronine sodium salt (T3), thereby reaching a total volume of 500 ml culture medium. In this embodiment, the final concentration of these supplements in DMEM may be as follows:
about 0.05 to 0.1 µg/ml adenine, for example about 0.025 µg/ml adenine,
about 1 to 10 µg/ml hydrocortisone,
about 0.5 to 5 ng/ml 3,3',5-Triiodo-L-thyronine sodium salt (T3), for example 1.36 ng/ml 3,3',5-Triiodo-L-thyronine sodium salt (T3).

In line with the above disclosure, a cell culture medium used herein is obtainable or that is obtained by the method of making the medium as described here.

In addition, a method of isolating mesenchymal stem cells from the amniotic membrane of the umbilical cord, wherein this method comprises cultivating amniotic membrane tissue in the culture medium prepared by the method is described here.

Thus, the present invention is also directed to (the use of) a cell culture medium comprising:
  DMEM in the final concentration of about 55 to 65% (v/v),
  F12 in a final concentration of about 5 to 15% (v/v),
  M171 in a final concentration of about 15 to 30% (v/v) and
  FBS in a final concentration of about 1 to 8% (v/v).

In certain embodiments of the culture medium described here, the medium comprises DMEM in the final concentration of about 57.5 to 62.5% (v/v), F12 in a final concentration of about 7.5 to 12.5% (v/v), M171 in a final concentration of about 17.5 to 25.0% (v/v) and FBS in a final concentration of about 1.75 to 3.5% (v/v). In other embodiments the culture medium may comprise DMEM in a final concentration of about 61.8% (v/v), F12 in a final concentration of about 11.8% (v/v), M171 in a final concentration of about 23.6% (v/v) and FBS in a final concentration of about 2.5% (v/v).

In addition, the culture medium may further comprise Epidermal Growth Factor (EGF) in a final concentration of about 1 ng/ml to about 20 ng/ml. In certain embodiments, the culture medium comprises EGF in a final concentration of about 10 ng/ml. The culture medium described herein may further comprise Insulin in a final concentration of about 1 µg/ml to 10 µg/ml. In such embodiments the culture medium may comprise Insulin in a final concentration of about 5 µg/ml.

The cell culture medium may further comprise at least one of the following supplements: adenine, hydrocortisone, and 3,3',5-Triiodo-L-thyronine sodium salt (T3). In certain embodiments the culture medium comprises all three of adenine, hydrocortisone, and 3,3',5-Triiodo-L-thyronine sodium salt (T3). If present, the culture medium may comprise adenine in a final concentration of about 0.01 to about 0.1 µg/ml adenine or of about 0.05 to about 0.1 µg/ml adenine, hydrocortisone in a final concentration of about 0.1 to about 10 µg/ml hydrocortisone or of about 1 to about 10

µg/ml hydrocortisone and/or 3,3',5-Triiodo-L-thyronine sodium salt (T3) in a final concentration of about 0.5 to about 5 ng/ml.

In embodiments of the cell culture medium, 500 ml of the cell culture medium of the present invention comprise:
i. 250 ml of DMEM
ii. 118 ml M171
iii. 118 ml DMEM/F12
iv. 12.5 ml Fetal Bovine Serum (FBS) (final concentration of 2.5%)
In further embodiments, the cell culture medium may further comprise
v. EGF in a final concentration of 10 ng/ml, and
vi. Insulin in a final concentration of 5 µg/ml.
Both, insulin and EGF can be added to the culture medium using a stock solution of choice, such that the total volume of the culture medium does not exceed 500 ml.

In a particular example, the components i. to vi. of the culture medium used in the present invention are the components indicated in FIG. 5, meaning they are obtained from the respective manufacturers using the catalogue number indicated in FIG. 5. The medium that is obtained from mixing the components i. to vi. as indicated in FIG. 5 is also referred herein as "PTT-6". It is again noted in this context that the constituents i. to vi. as well as any other ingredient such as an antibiotic of any other commercial supplier can be used in making the medium of the present invention.

In addition, the cell culture medium of the invention may comprise adenine in a final concentration of about 0.01 to about 0.1 µg/ml adenine or of about 0.05 to about 0.1 µg/ml adenine, hydrocortisone in a final concentration of about 0.1 to 10 µg/ml, of about 0.5 to about 10n/ml, or of about 1 to about 10 µg/ml hydrocortisone and/or 3,3',5-Triiodo-L-thyronine sodium salt (T3) in a final concentration of about 0.1 to about 5 ng/ml or of about 0.5 to about 5 ng/ml.

To obtain the mesenchymal stem cell population as described herein the umbilical cord tissue may be cultured till a suitable number of (primary) mesenchymal cord lining stem cells have outgrown from the tissue. In typical embodiments, the umbilical cord tissue is cultivated until cell outgrowth of the mesenchymal stem cells of the amniotic membrane reaches about 70 to about 80% confluency. It is noted here that the term "confluency" or "confluence" is used in its regular meaning in the art of cell culture and is meant as an estimate/indicator of the number of adherent cells in a culture dish or a flask, referring to the proportion of the surface which is covered by cells. For example, 50 percent confluence means roughly half of the surface is covered and there is still room for cells to grow. 100 percent confluence means the surface is completely covered by the cells, and no more room is left for the cells to grow as a monolayer.

Once a suitable number of primary cells (mesenchymal cord lining stem cells) have been obtained from the cord lining tissue by tissue explant, the mesenchymal stem cells are removed from the cultivation container used for the cultivation. By so doing, a master cell bank containing the (primary) isolated mesenchymal stem cells of the amniotic membrane can be obtained. Typically, since mesenchymal stem cells are adherent cells, removing is carried out using standard enzymatic treatment. For example, the enzymatic treatment may comprise trypsination as described in International US patent application 2006/0078993, International patent application WO2006/019357 or International patent application WO2007/046775, meaning outgrowing cells can be harvested by trypsinization (0.125% trypsin/0.05% EDTA) for further expansion. If the harvested mesenchymal stem cells are, for example, used for generating a master cell bank, the cells can also be cryo-preserved and stored for further use as explained herein below.

Once being harvested, the mesenchymal stem cells can be transferred to a cultivation container for subculturing. The subculturing can also be started from frozen primary cells, i.e. from the master cell bank. For subculturing, any suitable amount of cells can be seeded in a cultivation container such as cell culture plate. The mesenchymal stem cells can, for this purpose, be suspended in a suitable medium (most conveniently, the culture medium PTT-6) for subculturing at a concentration of, for example, about $0.5 \times 10^6$ cells/ml to about $5.0 \times 10^6$ cells/ml. In one embodiment the cells are suspended for subcultivation at a concentration of about $1.0 \times 10^6$ cells/ml. The subculturing can be carried out by cultivation either in simple culture flasks but also, for example, in a multilayer system such as CellStacks (Corning, Corning, N.Y., USA) or Cellfactory (Nunc, part of Thermo Fisher Scientific Inc., Waltham, Mass., USA) that can be stacked in incubators. Alternatively, the subculturing can also be carried out in a closed self-contained system such as a bioreactor. Different designs of bioreactors are known to the person skilled in the art, for example, parallel-plate, hollow-fiber, or micro-fluidic bioreactors. See, for example, Sensebe et al. "Production of mesenchymal stromal/stem cells according to good manufacturing practices: a review", supra. An illustrative example of a commercially available hollow-fiber bioreactor is the Quantum® Cell Expansion System (Terumo BCT, Inc). that has, for example, been used for the expansion of bone marrow mesenchymal stem cells for clinical trials (cf., Hanley et al, Efficient Manufacturing of Therapeutic Mesenchymal Stromal Cells Using the Quantum Cell Expansion System, *Cytotherapy*. 2014 August; 16(8): 1048-1058). Another example of commercially available bioreactors that can be used for the subculturing of the mesenchymal stem cell population of the present invention is the Xuri Cell Expansion System available from GE Heathcare. The cultivation of the mesenchymal stem cell population in an automated system such as the Quantum® Cell Expansion System is of particular benefit if a working cell bank for therapeutic application is to be produced under GMP conditions and a high number of cells is wanted.

The subculturing of the mesenchymal cord ling stem cells described herein takes place in a culture medium described herein such as the PTT-6 medium. Accordingly, the culture medium such as PTT-6 can be used both for the isolation of the mesenchymal stem cells from the amniotic membrane and the subsequent cultivation of the isolated primary cells by subcultivation. Also for the subcultivation, the mesenchymal stem cells can be cultured till a suitable number of cells have grown. In illustrative embodiments the mesenchymal stem cells are subcultured till the mesenchymal stem cells reach about 70 to about 80% confluency.

The isolation/cultivation of the population of mesenchymal cord lining stem cells can be carried out under standard conditions for the cultivation of mammalian cells. Typically, the method of the invention of isolating the population of the mesenchymal cord lining stem cells is typically carried out at conditions (temperature, atmosphere) that are normally used for cultivation of cells of the species of which the cells are derived. For example, human umbilical cord tissue and the mesenchymal cord lining stem cells, respectively, are usually cultivated at 37° C. in air atmosphere with 5% $CO_2$. In this context, it is noted that the mesenchymal cells may be derived of any mammalian species, such as mouse, rat, guinea pig, rabbit, goat, horse, dog, cat, sheep, monkey or human, with mesenchymal stem cells of human origin being preferred in one embodiment.

Once a desired/suitable number of mesenchymal cord lining stem cells have been obtained from the subculture, the mesenchymal stem cells can be harvested by removing them from the cultivation container used for the subcultivation. The harvesting of the mesenchymal stem cells is typically again carried out by enzymatic treatment, including trypsination of the cells. The isolated mesenchymal stem cells are subsequently collected and are either directly used or preserved for further use. Typically, preserving is carried out by cryo-preservation. The term "cryo-preservation" is used herein in its regular meaning to describe a process where the mesenchymal stem cells are preserved by cooling to low sub-zero temperatures, such as (typically) −80° C. or −196° C. (the boiling point of liquid nitrogen). Cryo-preservation can be carried out as known to the person skilled in the art and can include the use of cryo-protectors such as dimethylsulfoxide (DMSO) or glycerol, which slow down the formation of ice-crystals in the cells of the umbilical cord.

The isolated population of the mesenchymal cord lining stem cells that is obtained by the isolation method as described herein is highly defined and homogenous. In typical embodiments of the method at least about 90% or more, about 91% or more, about 92% or more, about 93% or more, about 94% or more, about 95% or more, about 96% or more, about 97% or more, about 98% or more about 99% or more of the isolated mesenchymal stem cells express the following markers: CD73, CD90 and CD105. In addition, in these embodiments at least about 90% or more, about 91% or more, about 92% or more, about 93% or more, about 94% or more, about 95% or more, about 96% or more, about 97% or more, about 98% or more about 99% or more of the isolated mesenchymal stem cells may lack expression of the following markers: CD34, CD45 and HLA-DR. In particular embodiments, about 97% or more, about 98% or more, or about 99% or more of the isolated mesenchymal stem cell population express CD73, CD90 and CD105 while lacking expression of CD34, CD45 and HLA-DR.

Thus, in line with the above disclosure a mesenchymal stem population isolated from the amniotic membrane of the umbilical cord, wherein at least about 90% or more cells of the stem cell population express each of the following markers: CD73, CD90 and CD105. In preferred embodiments at least about 91% or more, about 92% or more, about 93% or more, about 94% or more, about 95% or more, about 96% or more, about 97% or more, about 98% or more about 99% or more cells of the isolated mesenchymal stem cell population are CD73+, CD90+ and CD105+, meaning that this percentage of the isolate cell population express each of CD73, CD90 and CD105 (cf. the Experimental Section of the present application) can be used herein. In addition, at least about 90% or more, about 91% or more, about 92% or more, about 93% or more, about 94% or more, about 95% or more, about 96% or more, about 97% or more, about 98% or more about 99% or more of the isolated mesenchymal stem cells may lack expression of the lack expression of the following markers. In particular embodiments about 97% or more, about 98% or more, or about 99% or more cells of the isolated mesenchymal stem cell population express CD73, CD90 and CD105 while lacking expressing of CD34, CD45 and HLA-DR. Such a highly homogenous population of mesenchymal stem cells derived from the amniotic membrane of the umbilical cord has been reported for the first time in U.S. provisional application No. 62/404,582, filed Oct. 5, 2016 as well as in co-pending U.S. application Ser. No. 15/725,913, filed 5 Oct. 2017 as well as in co-pending PCT application PCT/S G2017/050500, also filed 5 Oct. 2017, and meets the criteria for mesenchymal stem cells to be used for cellular therapy (also cf. the Experimental Section and, for example, Sensebe et al. "Production of mesenchymal stromal/stem cells according to good manufacturing practices: a review", supra). It is noted in this context that this mesenchymal stem cell population can be obtained by either the isolating method of the present invention but also by a different method such as cell sorting, if needed.

A method of making a culture medium for isolating mesenchymal stem cells as described herein can comprise, mixing to obtain a final volume of 500 ml culture medium:
i. 250 ml of DMEM
ii. 118 ml M171
iii. 118 ml DMEM/F12
iv. 12.5 ml Fetal Bovine Serum (FBS) to reach a final concentration of 2.5% (v/v).

As explained above, DMEM/F12 medium is a 1:1 mixture of DMEM and Ham's F12 medium.

Thus, 118 ml DMEM/F12 medium contain 59 ml DMEM and 59 ml F12. Accordingly, when using this method of making a culture medium, the final concentrations (v/v) with 500 ml total volume are as follows:
DMEM: 250 ml+59 ml=309 ml, corresponds to 309/500=61.8% (v/v)
M171: 118 ml, corresponds to 118/500=23.6% (v/v)
F12: 59 ml, corresponds to 59/500=11.8% (v/v).

The present invention also relates to a method of treating a subject having a disease, the method comprising topically administering a mesenchymal stem cell population as described herein to the subject, wherein the mesenchymal stem cell population is administered within about 96 hours from the time point the mesenchymal stem cell population has been harvested.

Similarly, the present invention also relates to mesenchymal stem cell population as described herein for use in a method of treating a disease of a subject, wherein the mesenchymal stem cell population is topically administered within about 96 hours from the time point the mesenchymal stem cell population has been harvested The subject to be treated may be any suitable subject. The subject can be a vertebrate, more preferably a mammal. Mammals include, but are not limited to, farm animals, sport animals, pets, primates, dogs, horses, mice and rats. A mammal can also be a human, dog, cat, cow, pig, mouse, rat etc. Thus, in one embodiment, the subject is a vertebrate. The subject can also be a human subject. The subject therefore can be a subject in need of treatment. As such the subject may be afflicted with a disease as described elsewhere herein. In some embodiments the subject is afflicted with Type I or Type II diabetes with chronic foot ulcers. Preferably, the subject is negative for HLA antibodies to the mesenchymal stem cell population.

The mesenchymal stem cell population may be applied in any dosage. The dosage may be therapeutically effective. The "therapeutically effective amount/dosage" can vary with factors including but not limited to the activity of the cells used, stability of the cells in the patient's body, the severity of the conditions to be alleviated, the age and sensitivity of the patient to be treated, adverse events, and the like, as will be apparent to a skilled artisan. The amount of administration can be adjusted as the various factors change over time.

The dosage in which the mesenchymal stem cells are applied can also be a unit dosage. For example, the mesenchymal stem cell population can be applied in a unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells. In a particular embodiment, the mesenchymal stem cell population is applied in a unit dosage of about 10 million cells.

The mesenchymal stem cells may be applied several times to the same subject. For example, stem cells are applied once, twice, three times or more a week. In principle any unit dosage of mesenchymal stem cells may be applied for the number of times suitable to cure or alleviate the disease. For example, the mesenchymal stem cell population can be applied once, twice three times or more a week. The mesenchymal stem cell population may also be applied for one, two, three, four, five, six, seven, eight, nine, ten, elven weeks or more.

Thus, the unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells is administered once or twice a week. The unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells can also be administered one or twice a week for a period of time of three weeks, of four weeks, or five weeks or of six weeks, or of seven weeks, or of eight weeks or of ten weeks or more weeks.

It is also contemplated by the method of treatment of the present invention that the mesenchymal stem cell population is applied in a dosage of about 1000 cells/cm$^2$ to about 5 million cells/cm$^2$. Here, the expression cm$^2$ means the area of the wound/skin to which the stem cells are applied. It is also envisioned that the mesenchymal stem cell population is applied in a dosage of about 100,000 cells/cm$^2$, 300,000 cells/cm$^2$ or 500,000 cells/cm$^2$. The mesenchymal stem cell population can also be applied two times a week for about 8 weeks in a dosage of about 100,000 cells/cm$^2$, about 300,000 cells/cm$^2$ or about 500,000 cells/cm$^2$.

The mesenchymal stem cell population is administered within about 96 hours from the time point where the mesenchymal stem cell population has been harvested. How harvesting can take place is described elsewhere herein. It is also possible that the mesenchymal stem cell population is applied within about 72 hours, about 48 hours, about 24 hours, about 12 hours, about 6 hours or less from the time point where the mesenchymal stem cell population has been harvested. Between the time of harvesting and application, the mesenchymal stem cell population may be transported or stored by the method of transporting/storing of the present invention. Thus, aspects as described for the method of transporting/storing of the present application equally relate to the method of treatment of the present invention mutatis mutandis.

The method of treatment of the present invention serves to alleviate a disease suffered by the subject. In principle, any disease that may be treated by the mesenchymal stem cell population as described herein is meant here. In particular, the disease may be a skin disease or a wound. The wound may be caused by any cause e.g. by a burn, a bite, a trauma, a surgery, or a disease. The wound can also be caused by diabetic disease. Therefore, the wound can also be a diabetic wound. The wound may also be a diabetic foot ulcer. Notably, the mesenchymal stem cell population may, for example, be placed directly onto a wound such as a burn or a diabetic wound (see International patent application WO2007/046775).

As described herein, between the harvesting of the mesenchymal stem cell population as described herein and their application to a subject the cells may be transported/stored in the carrier as defined herein. Therefore, the method of treating a subject of the present invention may also comprise the step of separating the mesenchymal stem cell population from the carrier before administering the mesenchymal stem cell population to the subject. The person skilled in the art knows how to perform the separation of cells from a carrier. For example, the separating of the mesenchymal stem cell population from the carrier may comprise centrifugation. Additionally or alternatively, separating the mesenchymal stem cell population from the carrier can comprise withdrawing the cell population from the vial by means of syringe.

After separating the stem cells from the carrier or after harvesting the mesenchymal stem cells or after obtaining mesenchymal stem cell population as described herein by any other method these cells are topically applied to a subject. In principle any way of topical administration is meant herein. The administering the mesenchymal stem cell population may be performed by means of a syringe. It is however also possible, to contact the mesenchymal stem cells within a cream, ointment, gel, suspension or any other suitable substance before applying the mesenchymal stem cells to the subject. The mesenchymal stem cell population after application to the subject may be held in place e.g. by a dressing such as Tegaderm® dressing and a crepe bandage to cover the Tegaderm® dressing. For a more even distribution of cells the application site may be gently massaged.

The present invention also relates to a unit dosage comprising about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells of a mesenchymal stem cell population as described herein.

It is also envisioned that the unit dosage comprises about 10, about 9, about 8, about 7, about 6, about 5, about 4, about 3, about 2, about 1, about 0.5, about 0.25, or about 0.1 million cells. Preferably the unit dosage comprises about 10 million cells. It is further envisioned that the unit dosage comprises about 1000 cells to about 5 million cells. The unit dosage can be applied in a dosage of about 100,000 cells, 300,000 cells or 500,000 cells. As described herein the unit dosage may be applied topically. For example, the unit dosage may be applied topically per cm$^2$.

The unit dosage can be applied once, twice, three times or more a week. For example, the unit dosage can be applied for one, two, three, four, five, six, seven, eight, nine, ten, elven weeks or more. The unit dosage comprising of about 100,000 cells, about 300,000 cells or about 500,000 cells can be applied two times a week for 8 weeks, preferably onto 1 cm$^2$.

The unit dosage can be contained in any suitable container. For example, the unit dosage can be contained in a 1 ml vial. In such cases, for example 0.1 ml of the vial can be applied onto the subject, preferably per cm$^2$. The unit dosage may alternatively be contained in a syringe.

The unit dosage of the present invention the cells can be in contact with a liquid carrier as defined herein. If this is the case then the mesenchymal stem cells are separated from the carrier before administration. For example, the cells can be centrifuged and isolated before administration to a subject. The carrier may be any carrier as described herein, such as HypoThermosol™ or Hypothermosol™-FRS The method of treatment and the unit dosage of the present invention can comprise utilization of viable cells. How viability can be tested is described elsewhere herein.

The invention will be further illustrated by the following non-limiting Experimental Examples.

Sequences as used herein are depicted in below Table 1.

TABLE 1

Sequences as used herein.

| SEQ ID NO. | What | Sequence |
|---|---|---|
| 1 | CD73 identifier P21589 of Uniprot, version number 1 as of May 1, 1991: | MCPRAARAPATLLLALGAVLWPAAGAWELTILHTNDVHSRLEQTSEDS SKCVNASRCMGGVARLFTKVQQIRRAEPNVLLLDAGDQYQGTIWFTVY KGAEVAHFMNALRYDAMALGNHEFDNGVEGLIEPLLKEAKFPILSANIK AKGPLASQISGLYLPYKVLPVGDEVVGIVGYTSKETPFLSNPGTNLVFED EITALQPEVDKLKTLNVNKIIALGHSGFEMDKLIAQKVRGVDVVVGGHS NTFLYTGNPPSKEVPAGKYPFIVTSDDGRKVPVVQAYAFGKYLGYLKIE FDERGNVISSHGNPILLNSSIPEDPSIKADINKWRIKLDNYSTQELGKTIVY LDGSSQSCRFRECNMGNLICDAMINNNLRHTDEMFWNHVSMCILNGGG IRSPIDERNNGTITWENLAAVLPFGGTFDLVQLKGSTLKKAFEHSVHRYG QSTGEFLQVGGIHVVYDLSRKPGDRVVKLDVLCTKCRVPSYDPLKMDE VYKVILPNFLANGGDGFQMIKDELLRHDSGDQDINVVSTYISKMKVIYP AVEGRIKFSTGSHCHGSFSLIFLSLWAVIFVLYQ |
| 2 | CD90 identifier P04216 of Uniprot, version number 2 as of May 2, 2002: | MNLAISIALLLTVLQVSRGQKVTSLTACLVDQSLRLDCRHENTSSSPIQY EFSLTRETKKHVLFGTVGVPEHTYRSRTNFTSKYNMKVLYLSAFTSKDE GTYTCALHHSGHSPPISSQNVTVLRDKLVKCEGISLLAQNTSWLLLLLLS LSLLQATDFMSL |
| 3 | CD105 identifier P17813 of Uniprot, version number 2 as of Jul. 15, 1998: | MDRGTLPLAVALLLASCSLSPTSLAETVHCDLQPVGPERGEVTYTTSQVS KGCVAQAPNAILEVHVLFLEFPTGPSQLELTLQASKQNGTWPREVLLVL SVNSSVFLHLQALGIPLHLAYNSSLVTFQEPPGVNTTELPSFPKTQILEWA AERGPITSAAELNDPQSILLRLGQAQGSLSFCMLEASQDMGRTLEWRPRT PALVRGCHLEGVAGHKEAHILRVLPGHSAGPRTVTVKVELSCAPGDLDA VLILQGPPYVSWLIDANHNMQIWTTGEYSFKIFPEKNIRGFKLPDTPQGL LGEARMLNASIVASFVELPLASIVSLHASSCGGRLQTSPAPIQTTPPKDTC SPELLMSLIQTKCADDAMTLVLKKELVAHLKCTITGLTFWDPSCEAEDR GDKFVLRSAYSSCGMQVSASMISNEAVVNILSSSSPQRKKVHCLNMDSL SFQLGLYLSPHFLQASNTIEPGQQSFVQVRVSPSVSEFLLQLDSCHLDLGP EGGTVELIQGRAAKGNCVSLLSPSPEGDPRFSFLLHFYTVPIPKTGTLSCT VALRPKTGSQDQEVHRTVFMRLNIISPDLSGCTSKGLVLPAVLGITFGAF LIGALLTAALWYIYSHTRSPSKREPVVAVAAPASSESSSTNHSIGSTQSTP CSTSSMA |
| 4 | CD34 identifier P28906 of Uniprot, version number 2 as of Jul. 15, 1998: | MLVRRGARAGPRMPRGWTALCLLSLLPSGFMSLDNNGTATPELPTQGT FSNVSTNVSYQETTTPSTLGSTSLHPVSQHGNEATTNITETTVKFTSTSVIT SVYGNTNSSVQSQTSVISTVFTTPANVSTPETTLKPSLSPGNVSDLSTTSTS LATSPTICPYTSSSPILSDIKAEIKCSGIREVICLTQGICLEQNKTSSCAEFKK DRGEGLARVLCGEEQADADAGAQVCSLLLAQSEVRPQCLLLVLANRTEI SSKLQLMKKHQSDLKKLGILDFTEQDVASHQSYSQKTLIALVTSGALLA VLGITGYFLMNRRSWSPTGERLGEDPYYTENGGGQGYSSGPGTSPEAQG KASVNRGAQENGTGQATSRNGHSARQHVVADTEL |
| 5 | CD45 identifier P08575 of Uniprot, version number 2 as of Jul. 19, 2003: | MYLWLKLLAFGFAFLDTEVFVTGQSPTPSPTGLTTAKMPSVPLSSDPLPT HTTAFSPASTFERENDFSETTTSLSPDNTSTQVSPDSLDNASAFNTTGVSS VQTPHLPTHADSQTPSAGTDTQTFSGSAANAKLNPTPGSNAISDVPGERS TASTFPTDPVSPLTTTLSLAHHSSAALPARTSNTTITANTSDAYLNASETT TLSPSGSAVISTTTIATTPSKPTCDEKYANITVDYLYNKETKLFTAKLNVN ENVECGNNTCTNNEVHNLTECKNASVSISHNSCTAPDKTLILDVPPGVEK FQLHDCTQVEKADTTICLKWKNIETFTCDTQNITYRFQCGNMIFDNKEIK LENLEPEHEYKCDSEILYNNHKFTNASKIIKTDFGSPGEPQIIFCRSEAAHQ GVITWNPPQRSFHNFTLCYIKETEKDCLNLDKNLIKYDLQNLKPYTKYV LSLHAYIIAKVQRNGSAAMCHFTTKSAPPSQVWNMTVSMTSDNSMHVK CRPPRDRNGPHERYHLEVEAGNTLVRNESHKNCDFRVKDLQYSTDYTF KAYFHNGDYPGEPFILHHSTSYNSKALIAFLAFLIWTSIALLVVLYKIYDL HKICRSCNLDEQQELVERDDEKQLMNVEPIHADILLETYKRKIADEGRLF LAEFQSIPRVFSKFPIKEARKPFNQNICNRYVDILPYDYNRVELSEINGDAG SNYINASYIDGFICEPRKYIAAQGPRDETVDDFWRMIWEQKATVIVMVTR CEEGNRNKCAEYWPSMEEGTRAFGDVVVKINQHICRCPDYIIQICLNIVNK KEICATGREVTHIQFTSWPDHGVPEDPHLLLICLRRRVNAFSNFFSGPIVVH CSAGVGRTGTYIGIDAMLEGLEAENKVDVYGYVVKLRRQRCLMVQVE AQYILIHQALVEYNQFGETEVNLSELHPYLHNMKKRDPPSEPSPLEAEFQ RLPSYRSWRTQHIGNQEENKSKNRNSNVIPYDYNRVPLICHELEMSKESE |

TABLE 1-continued

Sequences as used herein.

| SEQ ID NO. | What | Sequence |
|---|---|---|
| | | HDSDESSDDDSDSEEPSKYINASFIMSYWKPEVMIAAQGPLKETIGDFWQ MIFQRKVKVIVMLTELKHGDQEICAQYWGEGKQTYGDIEVDLKDTDKS STYTLRVFELRHSKRKDSRTVYQYQYTNWSVEQLPAEPKELISMIQVVK QKLPQKNSSEGNKHHKSTPLLIHCRDGSQQTGIFCALLNLLESAETEEVV DIFQVVKALRKARPGMVSTFEQYQFLYDVIASTYPAQNGQVKKNNHQE DKIEFDNEVDKVKQDANCVNPLGAPEKLPEAKEQAEGSEPTSGTEGPEH SVNGPASPALNQGS |
| 6 | HLA-DR identifier P01903 of Uniprot, version number 1 as of Jul. 21, 1986: | MAISGVPVLGFFIIAVLMSAQESWAIKEEHVIIQAEFYLNPDQSGEFMFDF DGDEIFHVDMAKKETVWRLEEFGRFASFEAQGALANIAVDKANLEIMT KRSNYTPITNVPPEVTVLTNSPVELREPNVLICHDKFTPPVVNVTWLRNG KPVTTGVSETVFLPREDHLFRKFHYLPFLPSTEDVYDCRVEHWGLDEPLL KHWEFDAPSPLPETTENVVCALGLTVGLVGIIIGTIFIIKGVRKSNAAERR GPL |
| 7 | Human TGFbeta1 Uniprot no: P36897 version number 1 as of Jun. 1, 1994 | MEAAVAAPRPRLLLLVLAAAAAAAAALLPGATALQCFCHLCTKDNFTC VTDGLCFVSVTETTDKVIHNSMCIAEIDLIPRDRPFVCAPSSKTGSVTTTY CCNQDHCNKIELPTTVKSSPGLGPVELAAVIAGPVCFVCISLMLMVYICH NRIVIHHRVPNEEDPSLDRPFISEGTTLKDLIYDMTTSGSGSGLPLLVQRT IARTIVLQESIGKGRFGEVWRGKWRGEEVAVKIFSSREERSWFREAEIYQ TVMLRHENILGFIAADNKDNGTWTQLWLVSDYHEHGSLFDYLNRYTVT VEGMIKLALSTASGLAHLHMEIVGTQGKPAIAHRDLKSKNILVKKNGTC CIADLGLAVRHDSATDTIDIAPNHRVGTKRYMAPEVLDDSINMKHFESF KRADIYAMGLVFWEIARRCSIGGIHEDYQLPYYDLVPSDPSVEEMRKVV CEQKLRPNIPNRWQSCEALRVMAKIMRECWYANGAARLTALRIKKTLS QLSQQEGIKM |
| 8 | Human VEGFA Uniprot no: P15692 version number 2 as of Nov. 16, 2001 | MNFLLSWVHWSLALLLYLHHAKWSQAAPMAEGGGQNHHEVVKFMDV YQRSYCHPIETLVDIFQEYPDEIEYIFKPSCVPLMRCGGCCNDEGLECVPT EESNITMQIMRIKPHQGQHIGEMSFLQHNKCECRPKKDRARQEKKSVRG KGKGQKRKRKKSRYKSWSVYVGARCCLMPWSLPGPHPCGPCSERRKH LFVQDPQTCKCSCKNTDSRCKARQLELNERTCRCDKPRR |
| 9 | HUMAN Platelet-derived growth factor receptor alpha Uniprot no: P16234, version number 1 as of Apr. 1, 1990 | MGTSHPAFLVLGCLLTGLSLILCQLSLPSILPNENEKVVQLNSSFSLRCFG ESEVSWQYPMSEEESSDVEIRNEENNSGLFVTVLEVSSASAAHTGLYTCY YNHTQTEENELEGRHIYIYVPDPDVAFVPLGMTDYLVIVEDDDSAIIPCR TTDPETPVTLHNSEGVVPASYDSRQGFNGTFTVGPYICEATVKGKKFQTI PFNVYALKATSELDLEMEALKTVYKSGETIVVTCAVFNNEVVDLQWTY PGEVKGKGITMLEEIKVPSIKLVYTLTVPEATVKDSGDYECAARQATRE VKEMKKVTISVHEKGFIEIKPTFSQLEAVNLHEVKHFVVEVRAYPPPRIS WLKNNLTLIENLTEITTDVEKIQEIRYRSKLKLIRAKEEDSGHYTIVAQNE DAVKSYTFELLTQVPSSILDLVDDHHGSTGGQTVRCTAEGTPLPDIEWMI CKDIKKCNETSWTILANNVSNIITEIHSRDRSTVEGRVTFAKVEETIAVR CLAKNLLGAENRELKLVAPTLRSELTVAAAVLVLLVIVIISLIVLVVIWK QKPRYEIRWRVIESISPDGHEYIYVDPMQLPYDSRWEFPRDGLVLGRVLG SGAFGKVVEGTAYGLSRSQPVMKVAVKMLKPTARSSEKQALMSELKIM THLGPHLNIVNLLGACTKSGPIYIITEYCFYGDLVNYLHKNRDSFLSHHPE KPKKELDIFGLNPADESTRSYVILSFENNGDYMDMKQADTTQYVPMLER KEVSKYSDIQRSLYDRPASYKKKSMLDSEVKNLLSDDNSEGLTLLDLLSF TYQVARGMEFLASKNCVHRDLAARNVLLAQGKIVKICDFGLARDIMHD SNYVSKGSTFLPVKWMAPESIFDNLYTTLSDVWSYGILLWEIFSLGGTPY PGMMVDSTFYNKIKSGYRMAKPDHATSEVYEIMVKCWNSEPEKRPSFY HLSEIVENLLPGQYKKSYEKIHLDFLKSDHPAVARMRVDSDNAYIGVTY KNEEDKLKDWEGGLDEQRLSADSGYIIPLPDIDPVPEEEDLGKRNRHSSQ TSEESAIETGSSSSTFIKREDETIEDIDMMDDIGIDSSDLVEDSFL |
| 10 | Human Ang-1 Uniprot no: Q15389 version number 2 as of Jan. 1, 1998 | MTVFLSFAFLAAILTHIGCSNQRRSPENSGRRYNRIQHGQCAYTFILPEHD GNCRESTTDQYNTNALQRDAPHVEPDFSSQKLQHLEHVMENYTQWLQ KLENYIVENMKSEMAQIQQNAVQNHTATMLEIGTSLLSQTAEQTRKLTD VETQVLNQTSRLEIQLLENSLSTYKLEKQLLQQTNEILKIHEKNSLLEHKI LEMEGKHKEELDTLKEEKENLQGLVTRQTYIIQELEKQLNRATTNNSVL QKQQLELMDTVHNLVNLCTKEGVLLKGGKREEEKPFRDCADVYQAGF NKSGIYTIYINNMPEPKKVFCNMDVNGGGWTVIQHREDGSLDFQRGWK EYKMGFGNPSGEYWLGNEFIFAITSQRQYMLRIELMDWEGNRAYSQYD RFHIGNEKQNYRLYLKGHTGTAGKQSSLILHGADFSTKDADNDNCMCK CALMLTGGWWFDACGPSNLNGMFYTAGQNHGKLNGIKWHYFKGPSYS LRSTTMMIRPLDF |
| 11 | Human HGF Uniprot no: P14210 | MWVTKLLPALLLQHVLLHLLLLPIAIPYAEGQRKRRNTIHEFKKSAKTTL IKIDPALKIKTKKVNTADQCANRCTRNKGLPFTCKAFVFDKARKQCLWF PFNSMSSGVKKEFGHEFDLYENKDYIRNCIIGKGRSYKGTVSITKSGIKCQ |

TABLE 1-continued

Sequences as used herein.

| SEQ ID NO. | What | Sequence |
|---|---|---|
| | version number 2 as of Aug. 1, 1991 | PWSSMIPHEHSFLPSSYRGKDLQENYCRNPRGEEGGPWCFTSNPEVRYE VCDIPQCSEVECMTCNGESYRGLMDHTESGKICQRWDHQTPHRHKELPE RYPDKGFDDNYCRNPDGQPRPWCYTLDPHTRWEYCAIKTCADNTMND IDVPLETTECIQGQGEGYRGTVNTIWNGIPCQRWDSQYPHEHDMTPENF KCKDLRENYCRNPDGSESPWCFTTDPNIRVGYCSQIPNCDMSHGQDCYR GNGKNYMGNLSQTRSGLTCSMWDKNMEDLHRHIFWEPDASKLNENYC RNPDDDAHGPWCYTGNPLIPWDYCPISRCEGDTTPTIVNLDHPVISCAKT KQLRVVNGIPTRTNIGWMVSLRYRNKHICGGSLIKESWVLTARQCFPSR DLKDYEAWLGIHDVHGRGDEKCKQVLNVSQLVYGPEGSDLVLMKLAR PAVLDDEVSTIDLPNYGCTIPEKTSCSVYGWGYTGLINYDGLLRVAHLYI MGNEKCSQHHRGKVTLNESEICAGAEKIGSGPCEGDYGGPLVCEQHKM RMVLGVIVPGRGCAIPNRPGIFVRVAYYAKWIHKIILTYKVPQS |
| 12 | PDGFB human Uniprot no: P01127 version number 1 as of Jul. 21, 1986 | MNRCWALFLSLCCYLRLVSAEGDPIPEELYEMLSDHSIRSFDDLQRLLHG DPGEEDGAELDLNMTRSHSGGELESLARGRRSLGSLTIAEPAMIAECKTR TEVFEISRRLIDRTNANFLVWPPCVEVQRCSGCCNNRNVQCRPTQVQLR PVQVRKIEIVRKKPIFKKATVTLEDHLACKCETVAAARPVTRSPGGSQEQ RAKTPQTRVTIRTVRVRRPPKGKHRKFKHTHDKTALKETLGA |
| 13 | Human IL-10 Uniprot no: P22301 version number 1 as of Aug. 1, 1991 | MHSSALLCCLVLLTGVRASPGQGTQSENSCTHFPGNLPNMLRDLRDAFS RVKTFFQMKDQLDNLLLKESLLEDFKGYLGCQALSEMIQFYLEEVMPQ AENQDPDIKAHVNSLGENLKTLRLRLRRCHRFLPCENKSKAVEQVKNAF NKLQEKGIYKAMSEFDIFINYIEAYMTMKIRN |

EXPONENTIAL EXAMPLES

1. Cryopreservation of Umbilical Cord Tissue Prior to Isolation of Mesenchymal Stem Cells Umbilical cord tissue (the umbilical cords were donated with informed consent of the mother) was processed for the subsequent isolation of the mesenchymal stem cells from the amniotic membrane of the umbilical cord as follows.

1.1 Washing of Umbilical Cord Tissue Sample:

a. Remove scalpels from the protective cover.
b. Hold the umbilical cord securely using the forceps and cut the cord into a 10 cm length piece using a scalpel. Place the unused cord back in the original tissue cup.
c. Transfer the 10 cm long umbilical cord piece into a new 150 mm culture dish. The 150 mm culture dish may be used in place of the cups.
d. Use the cover of the 150 mm culture dish as a resting place for forceps and scalpel.
e. Remove 25 ml Plasmalyte A (Baxter, Catalog #2B2543Q) with a 30 ml syringe. Hold the syringe at a 45° angle using one hand and dispense the Plasmalyte A directly onto the umbilical cord tissue.
f. Holding the culture dish at a slight angle remove the Plasmalyte A with a 30 ml syringe and blunt needle.
g. Collect used Plasmalyte A in a 300 ml transfer bag that serves as a trash container and dispose it in the biohazard bin.
h. Repeat wash procedure, if necessary using a new culture dish for each wash. Make sure all blood clots on the surface have been removed. More Plasmalyte A can be used if needed to clean the tissue.
i. Place the tissue into a new labeled tissue culture dish to continue cutting the tissue. Place 20 ml of Plasmalyte A into the dish so the tissue does not dry out while cutting it.
j. Cut the cords into equal approximately 1-cm sections resulting in 10 sections in total.
k. Further cut each 1 cm section into smaller pieces with approximately 0.3 cm×0.3 cm to 0.5 cm×0.5 cm per section.
l. Remove any Plasmalyte A that is in the dish.
m. Pull 25 ml Plasmalyte A with a 30 ml syringe from the original Plasmalyte A bag and dispense directly on the umbilical cord tissue pieces.
n. Hold culture dish in an angle to collect all Plasmalyte A used for washing the tissue on one side and remove it with a syringe and blunt needle.
o. Repeat wash one more time. There should not be any clots left.

NOTE: If the cord is not frozen right away, the umbilical cord tissue is kept in Plasmalyte A until ready to freeze.

1.2 Cryopreservation of Umbilical Cord Tissue:

a. Prepare cryopreservation solution:
i. Prepare 50 ml freezing solution consisting of 60% Plasmalyte A, 30% of 5% Human Serum Albumin, and 10% dimethyl sulfoxide (DMSO).
ii. Label a 150 ml transfer bag with "Tissue freeze solution" and attach a plasma transfer set to the port using aseptic technique.
iii. Remove 30 ml Plasmalyte A with a 30 ml Syringe from the original Plasmalyte A bag and transfer it in the transfer bag labeled "tissue freeze solution" with the time and date solution is made.
iv. Remove 15 ml of 5% Human Serum Albumin with a 20 ml syringe and transfer it into the labeled transfer bag.
v. Add 5 ml DMSO to the transfer bag.
vi. Mix well and record mixing of freeze solution
b. Remove the Plasmalyte A from the tissue before adding the freeze solution.
c. Using a 60 ml syringe, pull all 50 mls of the freeze solution into the syringe add approximately 30 ml freeze solution to the 150 mm cell culture dish containing the umbilical cord tissue. Place a blunt needle on the syringe to keep it sterile.

d. Swirl the culture dish containing the tissue and freezing solution every minute for 10 minutes.

e. Using forceps, select 8 randomly chosen sections and place them in each of the four 4 ml cryovials. Select 4 randomly chosen sections and place them into one 1.8 ml cryovial. These sections should be free of blood clots.

f. Fill each cryovial containing the umbilical cord tissue with the remaining freezing solution to the 3.6 ml filling line for the 4 ml tubes and the 1.8 ml line for the 1.8 nil Nunc vial.

g. Label one Bactec Lytic/10—Anaerobic/F and one Bactec Plus Aerobic/F bottle with tissue ID.

h. Remove 20 ml freeze solution from the culture dish with a syringe and a blunt needle, after wiping the Bactec vials with an alcohol swab, switch the blunt needle for an 18 g needle and inoculate the aerobic and the anaerobic Bactec bottles with 10 ml each.

i. Start controlled rate freezer.

j. After controlled rate freeze is completed place the units in a continuous temperature monitored liquid nitrogen freezer until further use.

2. Isolation of Mesenchymal Cord Lining Stem Cells from Umbilical Cord Tissue 2.1. Preparing Media for Processing MSCs from Umbilical Cord Tissue:

a. To make 500 ml PTT6 (culture/growth media) add the following in the order listed:
i. DMEM, 250 ml
ii. M171 118 ml
iii. DMEM F12 118 ml
iv. FBS 12.5 ml (final concentration of 2.5%)
v. EGF 1 ml (final concentration of 10 ng/ml)
vi. Insulin 0.175 ml (final concentration of 5 µg/ml)

The above-mentioned volumes of components i. to vi when result in a final volume of 499.675 ml culture medium. If no further components are added to the culture medium, the remaining 0.325 ml (to add up to a volume of 500 ml) can, for example, be any of components i. to iv, that means either DMEM, M171, DMEM/F12 or FBS. Alternatively, the concentration of the stock solution of EGF or Insulin can of course be adjusted such that the total volume of the culture medium is 500 ml. Alternatively, a stock solution of an antibiotic such as Penicillin-Streptomycin-Amphotericin can be added to result in a final volume of 500 ml. It is also possible to, add to the culture medium a volume of 0.325 ml of one or more of the following supplements: adenine, hydrocortisone, 3,3',5-Triiodo-L-thyronine sodium salt (T3), thereby reaching a total volume of 500 ml culture medium.

vii. Label the bottle "PTT6" with date media was prepared, initial of the operator, and the phrase "expires on" followed by the expiration date. Expiration date is the earliest expiration date of any of the component or 1 month from the preparation date, whichever comes first.

b. To make the rinse media (Hank's Buffered Salt Solution (HBSS) without Calcium or Magnesium and with 5% FBS), add 2.5 ml FBS to 47.5 ml of HBSS in a 50 ml centrifuge tube. Label the tube "Rinse Media" with operator initials and date the media is made.

c. All media will be tested for sterility using Bactec Lytic/10—Anaerobic/F (Becton Dickinson & Company) and Bactec Pluc+Aerobic/F (Becton Dickinson & Company). Inject 20 ml of prepared media into each bottle.

2.2 Thawing of Umbilical Cord Tissue for MSC Harvesting:

a. Initiate the thaw once an operator is prepared to process the sample in the clean room. Do not thaw more than 1 vial at a time unless the vials originate from the same donor.

b. Wipe the water bath with disinfectant followed by 70% isopropanol and fill it with 1 L sterile water. Heat the water bath up to 36-38° C.

c. Prepare 10 mL of rinse medium consisting of 70% to 90% PlasmaLyte A in the clean room under a biosafety cabinet. Sterile filter the solution with a 0.2-µm syringe filter attached to a 10 ml syringe and keep the solution refrigerated until use.

d. Place a processing label on a 50 ml conical tube.

e. Confirm water bath temperature is at 36-38° C.

f. Take vial(s) of tissue from the liquid nitrogen storage and thaw rapidly in the 37° C. water bath filled with 1 L of sterile water. The vial holder for the Mr. Frosty Nalgene Cryo 1° C. freezing container floats with vials in place and can be used as a floating rack when thawing samples.

g. Remove the vial from the water bath and spray them with 70% Isopropanol solution. A good time to pull the vial from the water bath is when small ice can be seen floating in the vial—suggest internal temperature of the vial is less than 37° C.

h. Place vial into pass-through and alert the clean room processing technician.

2.3 Preparing for Tissue Processing:

a. Umbilical cord tissue processing should be performed in an environmentally monitored (EM) clean room. At the end of each shift, full room and hood cleaning are performed b. Prepare/clean the biosafety cabinet.

c. Perform viable particle counting while working in the biosafety cabinet.

d. Assemble all necessary supplies in the biosafety cabinet checking each for packaging damage and expiration dates. When handling syringes, serological pipets, sterile forceps, scalpels, tissue plates, and needles, make sure not to touch any surface that will come in contact with the sterile product. Only the exterior of the syringe barrel, tubing, plunger tip and/or needle cap or sheath may be safely handled. Discard supply if the surface has been touched or has touched a non-sterile surface.

e. Record lot numbers and expiration dates (if applicable) of all reagents and supplies to be used.

f. Receive the thawed vial by cleaning the vial with lint-free wipe moistened with 70% alcohol before transferring into the biosafety cabinet.

g. Using an aspirating needle with a syringe, withdraw as much liquid from the vial. Avoid suctioning the tissue.

h. Using sterile forceps, transfer the tissue into a sterile 100 mm petri dish.

i. Add an aliquot of 5 ml rinse medium to the tissue fragments.

j. Swirl the contents for 15-30 seconds, then remove the rinse medium with a pipette or syringe with aspirating needle. Repeat this rinse process twice.

k. Add 2 mL of rinse medium to the tissue to avoid drying out the tissue.

2.4. Initiating MSC Outgrowth from Tissue:

a. Label the bottom of a 6-well plate "Outgrowth 1" with MSC lot number or umbilical cord tissue ID and the date outgrowth is initiated. If 60 mm tissue culture dish is used, divide the plate into 4 quadrants by drawing a grid on the bottom of the dish.

b. Using sterile, disposable forceps, place one 3×3 mm to 5×5 mm tissue into each well. If using a 60 mm tissue culture dish, place the tissue into the middle of each quadrant to keep the tissues apart (more than 1 cm from each other).

c. Fill each well with 3 ml of PTT6.

d. Using an aspirating needle coupled to 30 ml syringe, withdraw enough media to barely cover the tissue. Do not tilt the plate. Do not touch the bottom of the well with the aspirating needle.
e. Using an inverted light microscope, observe for cell outgrowth every day (24±6 hrs). Real time cell culture imaging system may be used in place of the light microscope.
f. Change media every day. Be sure to equilibrate the media to room temperature before use.
  i. Aspirate off the medium.
  ii. Add 3 ml of PTT6.
  iii. Aspirate until tissue is barely submerged in the medium.
g. When cellular outgrowth is observed from the tissue, transplant the tissue to a new 6-well plate using the same procedure as 4.a to 4.e above except label the plate "Outgrowth 2". Maintain cell outgrowth in "Outgrowth 1" plate by adding 2 ml of PTT6 to each well. Observe for confluency every day. Replace media every 2-3 days (be sure to equilibrate the media to room temperature before use).
h. When cell outgrowth is observed in "Outgrowth 2" plate, repeat step 4.a to 4.e except label the plate "Outgrowth 3." Maintain cell outgrowth in "Outgrowth 2" plate by adding 2 nil of PTT6 to each well. Observe for confluency every day. Replace media every 2-3 days (be sure to equilibrate the media to room temperature before use).
i. When outgrowth is observed in "Outgrowth 3" plate, discard the tissue. If the tissues are very small and do not seem to interfere with cell growth, dispose of the tissue when subculturing.
j. When cells reach 40-50% confluency, observe cells every days to prevent over-expansion.
k. When cells reach 70-80% confluency, subculture the cells. Do not allow cells to expand beyond 80% confluence.

With the size of the tissue explants being about 1-3 mm, and the tissue explant/cell culture is performed in 175 mm squared culture dishes, the average number of mesenchymal stem cells harvested from an explant is typically about 4,000-6,000 cells/explant. Accordingly, when the mesenchymal stem cells are simultaneously grown out of 48 explants about 300,000 cells can be obtained at harvest. These 300,000 mesenchymal stem cells collected from explants can then be used for subculturing by seeding a 175 cm$^2$ cell culture flask with such 300,000 cells as described in the following Example 2.5 (this can be referred to as Passage 1). The mesenchymal stem cells obtained from this passage 1 can then be used to seed again 175 cm$^2$ flasks (Passage 2) and expand the cells as described in the following Example 2.5. The cells obtained from both Passage 1 and Passage 2 can be "banked" by cryo-preservation, with the mesenchymal stem cells obtained after Passage 2 being considered to represent the Master Cell Bank which will be for further expansion of the mesenchymal stem cells, for example, in a bioreactor as explained below in Example 2.7.

2.5. Subculturing MSC in Cell Culture Dishes
a. Perform viable particle while working in the biosafety cabinet. Equilibrate all media to room temperature before use.
b. When cell outgrowth reaches about 70-80% confluency, subculture cells.
  i. Remove PTT6 from the petri dish.
  ii. Rinse with HBSS without Calcium or Magnesium.
  iii. Add 0.2 ml 1× TrypLE-EDTA and swirl for 1-2 minutes.
  iv. Tilt the dish 30-45° to allow cells to shift down by gravitational flow. Gentle tapping on the side of the plate expedites detachment.
  v. Add 1 ml of PTT6. Pipette up and down gently then transfer cells to a 15 ml centrifuge tube. Use clean pipette tip with each well. Cells from all 6 wells can be pooled into a single 15 ml tube.
  vi. Centrifuge for 10 minutes at 1200 rpm.
  vii. Remove supernatant and resuspend cells with 5 ml PTT6.
c. Subculturing MSC
  i. Aliquot 50 µl of the cell suspension and assay for TNC and viability by Trypan Blue Exclusion Assay.
  ii. Count cells using a hemocytometer. Expect to count 20-100 cells/square. If the count higher than 100, dilute the original sample 1:5 and repeat Trypan Blue method using a hemocytometer.
  iii. Calculate viable cells/ml and total viable cells:
    1. Viable cells/ml=viable cell count×dilution factor×$10^4$
    2. Total viable cells=viable cell count×dilution factor×total volume×$10^4$
  iv. Calculate % viability:
    1. % viability=viable cell count×100/(viable cell count+dead cell count)
  v. Dilute the cell suspension to $1.0 \times 10^6$ cells/ml:
    1. "X" volume=Total viable cells/$10^6$ cells/ml
    2. For example, if total viable cell number is $1.0 \times 10^7$;
    3. "X"=$10^7/10^6$ cells/ml or 10 ml, therefore, you would bring your total cell volume up to 10 ml by adding 5 ml to your cell suspension (that is at 5 ml).
  vi. If the cell suspension is less than 106/ml, determine the volume required to seed $2 \times 106$ cells for each 150 mm petri dish or 175 cm2 flask.
    1. Volume for $2 \times 10^6$ cells=$2 \times 10^6$ cells÷viable cells/ml
    2. For example, if viable cells/ml is $8 \times 10^5$ cells/ml, $2 \times 10^6$ cells÷$8 \times 10^5$ cells/ml or 2.5 ml are needed.
  vii: Set aside 0.5 ml for MSC marker analysis.
  viii. Seed $2 \times 10^6$ cells to each 150 mm petri dish or 175 cm$^2$ flask with 30 ml PTT6.
  ix. Observe cells for attachment, colony formation, and confluence every three days. When cells reach 40-50% confluence, observe cells every one-two days to prevent over-expansion. DO NOT allow cells to expand beyond 80% confluence. A real time cell culturing monitoring system can be used in place of the light microscope.
  x. Replace media every 2-3 days.

2.6 Cryopreserving MSC Cells
a. Perform viable particle while working in the biosafety cabinet.
b. When cells reach 70-80% confluence, detach cells using 2 ml 1× TrypLE-EDTA for each 150 mm petri dish or 175 cm2 flask.
  i. Remove PTT6 from the petri dish.
  ii. Wash with 5 ml HBSS or PBS without calcium or magnesium.
  iii. Add 2 ml 1× TrypLE-EDTA and swirl for 1-2 minutes.
  iv. Tilt the dish 30-45° to allow cells to shift down by gravitational flow. Gentle tapping on the side of the petri dish helps to expedite detachment.
  v. Add 10 nil PTT6 to inactivate TrypLE. Mix well to dissociate cell clumps.
  vi. Transfer cells to 15 ml centrifuge tube using a Pasteur pipette.
  vii. Centrifuge for 10 minutes at 1200 rpm.
  viii. Aspirate medium and resuspend with 10 ml PTT6.
  ix. Aliquot 50 µl and determine total viable cell number and % viability as above. Cell count will need to be performed within 15 minutes as the cells may start clumping.

c. Preparing cells for cryopreservation
i. Prepare Cell Suspension Media and Cryopreservation Media and freeze the cells 2.7. Subculturing (Expansion) of MSC in a Quantum Bioreactor (Terumo BTC, Inc.)

It is also possible to use a Quantum Bioreactor can used to expand the MSC. The starting cell number for the expansion in the Quantum Bioreactor should range between 20 to 30 million cells per run. The typical yield per run is 300 to 700 million MSC at harvest. The Bioreactor is operated following the protocol of the manufacturer. The so obtained mesenchymal stem cells are typically cryo-preserved (see below) and serve as Working Cell Bank.

Materials/Reagents:
1. Quantum Expansion Set
2. Quantum Waste Bag
3. Quantum Media Bag
4. Quantum Inlet Bag
5. PTT6
6. PBS
7. Fibronectin
8. TrypLE
9. 3 ml syringe
10. Glucose test strips
11. Lactate test strips
12. 60 ml Cell Culture Plate or equivalent
13. Medical Grade 5% $CO_2$ Gas-mix
14. 50 ml Combi-tip Equipment:
1. Biosafety Cabinet
2. Glucose Meter (Bayer Healthcare/Ascensia Contour Blood Glucose Meter)
3. Lactate Plus (Nova Biomedical)
4. Peristaltic pump with head
5. Centrifuge, Eppendorf 5810
6. Sterile Tube Connector
7. M4 Repeat Pipettor
8. RF Sealer Procedure:
1. Preparing the Quantum Bioreactor
   a) Priming the Quantum Bioreactor
   b) Coating the bioreactor:
      1) Prepare the fibronectin solution in the biosafety cabinet.
         1) Allow lyophilized fibronectin to acclimate to room temperature (≥15 min at room temperature)
         2) Add 5 ml of sterile distilled water; do not swirl or agitate
         3) Allow fibronectin to go into solution for 30 min.
         4) Using a 10 ml syringe attached with an 18 g needle, transfer the fibronectin solution to a cell inlet bag containing 95 ml of PBS.
      2) Attach the bag to the "reagent" line
      3) Check for bubbles (bubbles may be removed by using "Remove IC Air" or "Remove EC Air" and using "Wash" as the inlet source.
      4) Open or set up program for coating the bioreactor (FIG. 1. Steps 3-5).
      5) Run the program
      6) While the program is running to coat the bioreactor, prepare a media bag with 4 L of PTT6 media.
      7) Attach the media bag to the IC Media line using a sterile tube connector.
      8) When the bioreactor coating steps are completed, detach the cell inlet bag used for fibronectin solution using a RF sealer.
   c) Washing off excess fibronectin
   d) Conditioning the bioreactor with media
2. Culturing the Cells in the Quantum Bioreactor
   a) Loading and attaching the cells with Uniform Suspension:
   b) Feeding and cultivation of the cells
      1) Chose media flow rate to feed the cells.
      2) Sample for lactate and glucose every day.
      3) Adjust the flow rate of the media as the lactate levels increase. The actual maximal tolerable lactate concentration will be defined by a flask culture from which the cells originate. Determine if adequate PTT6 media is in the media bag. If necessary, replace the PTT6 media bag with a fresh PTT6 media bag.
      4) When the flow rate has reached the desired value, measure lactate level every 8-12 hours. If the lactate level does not decrease or if the lactate level continues to increase, harvest the cells.
3. Harvesting the Cells from the Quantum Bioreactor
   a) When lactate concentration does not decrease, harvest the cells after sampling for lactate and glucose for the last time.
   b) Harvesting the cells:
      1) Attach cell inlet bag filled with 100 ml TrypLE to the "Reagent" line using a sterile tube connector.
      2) Confirm sufficient PBS is in the PBS bag. If not, attach a new bag with at least 1.7 liters of PBS to the "Wash" line using a sterile tube connector.
      3) Run the Harvest program
4. Cryopreserving the Cells
      1) Once the cells have been harvested, transfer the cells to 50 ml centrifuge tube to pellet the cells.
      2) Resuspend using 25 ml of cold cell suspension solution. Count the cells using Sysmex or Biorad Cell counter. Attach the cell count report to the respective Quantum Processing Batch Record.
      3) Adjust cell concentration to $2 \times 10^7$/ml
      4) Add equal volume cryopreservation solution and mix well (do not shake or vortex)
      5) Using a repeat pipettor, add 1 ml of the cell suspension in cryopreservative to each 1.8 ml vial. Cryopreserve using the CRF program as described in the SOP D6.100 CB Cryopreservation Using Controlled Rate Freezers
      6) Store the vials in a designated liquid nitrogen storage space.
      7) Attach the CRF run report to the form respective MSC P3-Quantum Processing Batch Record.

3. Analysis of Stem Cell Marker Expression in Mesenchymal Cord Lining Stem Populations Isolated from Umbilical Cord Tissue, Using Different Culture Media Flow cytometry experiments were carried out to analyse mesenchymal stem cells isolated from the umbilical cord for the expression of the mesenchymal stem cell markers CD73, CD90 and CD105.

For these experiments, mesenchymal stem cells were isolated from umbilical cord tissue by cultivation of the umbilical cord tissue in three different cultivation media, followed by subculturing of the mesenchymal stem cells in the respective medium as set forth in Example 2.

The three following culture media were used in these experiments: a) 90% (v/v/DMEM supplemented with 10% FBS (v/v), b) the culture medium PTT-4 described in US patent application US 2008/0248005 and the corresponding International patent application WO2007/046775 that consist of 90% (v/v) CMRL1066, and 10% (v/v) FBS (see paragraph [0183] of WO2007/046775) and c) the culture medium of the present invention PTT-6 the composition of which is described herein. In this flow cytometry analysis, two different samples of the cord lining mesenchymal stem cell (CLMC) population were analysed for each of the three used culture media.

The following protocol was used for the flow cytometry analysis.

Materials and Methods

| Instruments name | Company Name | Serial Name |
|---|---|---|
| BD FACS CANDO | BD | V07300367 |
| Inverted Microscope, CKX41SF | Olympus | 4K40846 |
| Centrifuge, Micro spin Tabletop | Biosan | 010213-1201-0003 |

| Reagent list | Company Name | CatLog Number |
|---|---|---|
| 10 X Trypsin | Biowest | X0930-100 |
| 10 X PBS | Lonza | 17-517Q |
| DMEM | Lonza | 12-604F |
| Fetal Bovine Serum | GE healthcare | A11-151 |

| Antibody list | Company Name | CatLog Number |
|---|---|---|
| Human CD73 Purified AD2 0.1 mg | BD | 550256 |
| Human CD90 Purified 5E10 1 mL | BD | 550402 |
| Human CD 105 Purified 266 0.1 mg | BD | 555690 |
| Alexa Fluor 647 goat anti-mouse IgG (H + L) *2 mg/mL* | BD | A21235 |

| Reagents name | Composition |
|---|---|
| 1 X PBS (1 L) | 100 ml of 10 X PBS + 900 ml of sterile distilled H20 |
| 1x PBA (50 ml) | 49.5 ml of 1XPBS + 0.5 ml of FBS |

Procedure a) Cell Isolation and Cultivation from the Umbilical Cord Lining Membrane
1. Explant tissue samples were incubated in a cell culture plate and submerged in the respective medium, then keep it in $CO_2$ incubator at 37° C. as explained in Example 2.
2. The medium was changed every 3 days.
3. Cell outgrowth from tissue culture explants was monitored under light microscopy.
4. At a confluence of about 70%, cells were separated from dish by trypsinization (0.0125% trypsin/0.05% EDTA) and used for flow cytometry experiments.

b) Trypsinization of Cells for Experiments
1. Remove medium from cell culture plate
2. Gently rinse with sterile 1×PBS to remove traces of FBS as FBS will interfere with the enzymatic action of trypsin.
3. Add 1× trypsin to cell culture plate and incubate for 3-5 min in 37° C.
4. Observe cells under microscope to ensure that they are dislodged. Neutralize trypsin by adding complete media containing FBS (DMEM with 10% FBS).
5. Use a pipette to break up cell clumps by pipetting cells in media against a wall of the plate. Collect and transfer cell suspension into 50 ml centrifuge tubes 6. Add sterile 1×PBS to plate and rinse it, Collect cell suspension into the same centrifuge tube.
7. Centrifuge it at 1800 rpm for 10 mins.
8. Discard supernatant and re-suspend cell pellet with PBA medium.

c) Counting Cells
1. Ensure that the haemocytometer and its cover slip are clean and dry, preferably by washing them with 70% ethanol and letting them dry before wiping them with Kim wipes (lint-free paper).
2. Aliquot a small amount of cells in suspension into a micro centrifuge tube and remove from the BSC hood.
3. Stain cells in suspension with an equal volume of Trypan Blue, e.g. to 500 µl of suspension add 500 µl of Trypan Blue (dilution factor=2×, resulting in 0.2% Trypan Blue solution).
4. Avoid exposure of cells to Trypan Blue for longer than 30 mins as Trypan Blue is toxic and will lead to an increase in non-viable cells, giving a false cell count.
5. Add 20 µl of the cell suspension mixture to each chamber of a haemocytometer and view under a light microscope.
   a. Count the number of viable cells (bright cells; non-viable cells take up Trypan Blue readily and thus are dark) in each quadrant of the haemocytometer for a total of 8 quadrants in the upper and lower chamber.
   Total cell count is given as (Average number of cells/quadrant)×$10^4$ cells/ml.

d) Staining Cells
i. Preparation before staining cells
   Cell suspension are aliquot into 3 tubes (CD73, CD90, CD105) in duplicates and 2 tubes (negative control), each containing 50,000 cells.
ii. Staining with primary antibody (Ab)
   Add 1 µl [0.5 mg/ml Ab] of primary antibody to 100 ul cell suspension. Incubate at 4° C. for 45 min.
   Make up to 1 ml with PBA.
   Centrifuge 8000 rpm at 4° C. for 5 mins.
   Remove supernatant.
   Add 1 ml of PBA and re-suspend pellet
   Centrifuge 8000 rpm at 4° C. for 5 mins.
   Remove supernatant.
   Re-suspend in 100 ul PBA.
iii. Staining with secondary Ab—in the dark
   Add 1 ul [0.5 mg/ml ab] of secondary antibody to 100 ul cell suspension. Incubate at 4° C. for 30 min.
   Make up to 1 ml with PBA.
   Centrifuge 8000 rpm at 4° C. for 5 mins.
   Remove supernatant.
   Add 1 ml of PBA and re-suspend pellet
   Centrifuge 8000 rpm at 4° C. for 5 mins.
   Remove supernatant
   Re-suspend in 200-300 ul PBA for flow cytometry analysis
   Transfer cells to FACS tube for reading in BD FACS CANDO flow cytometry.

Figure 6B:
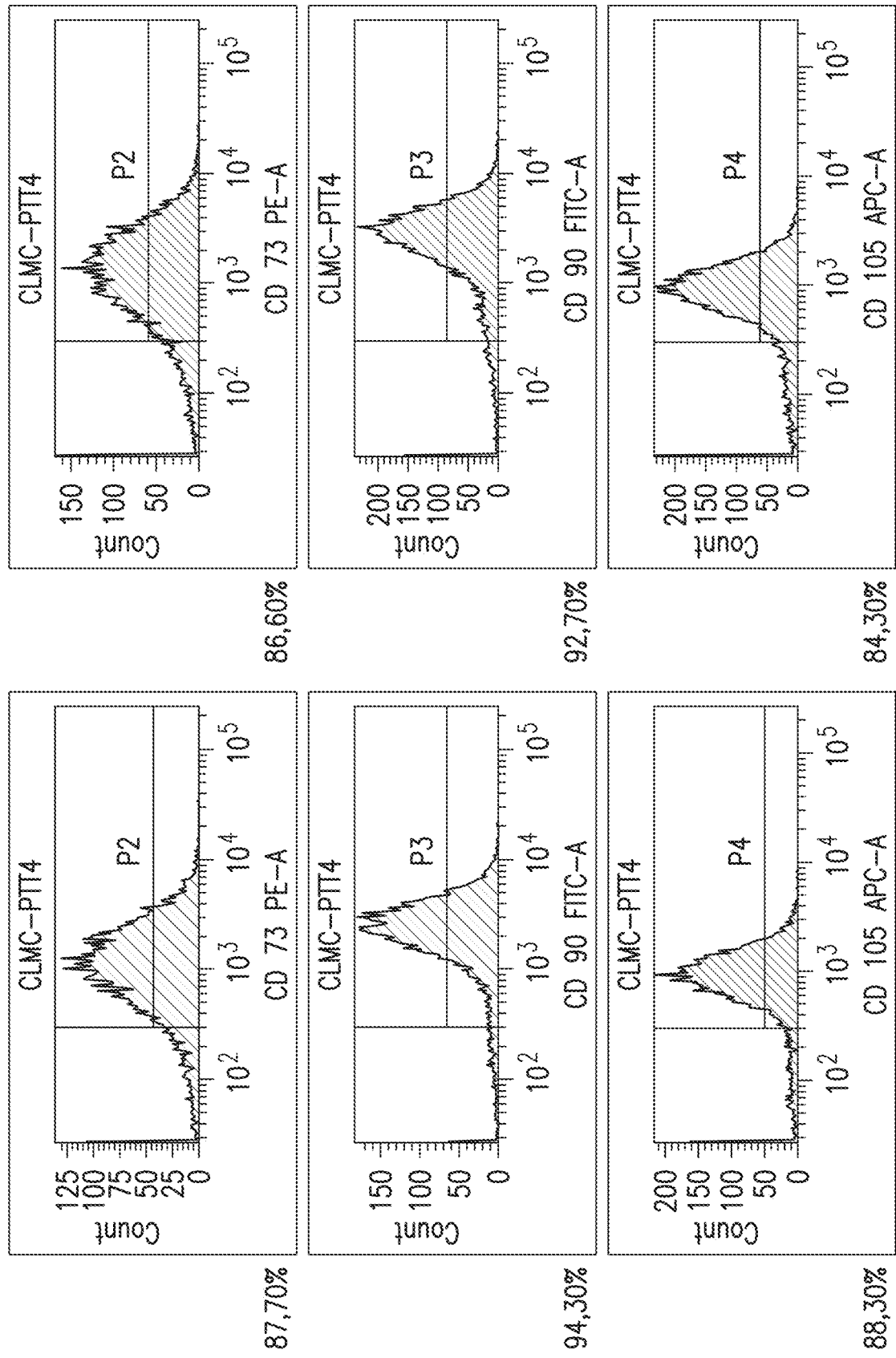
Figure 6C:
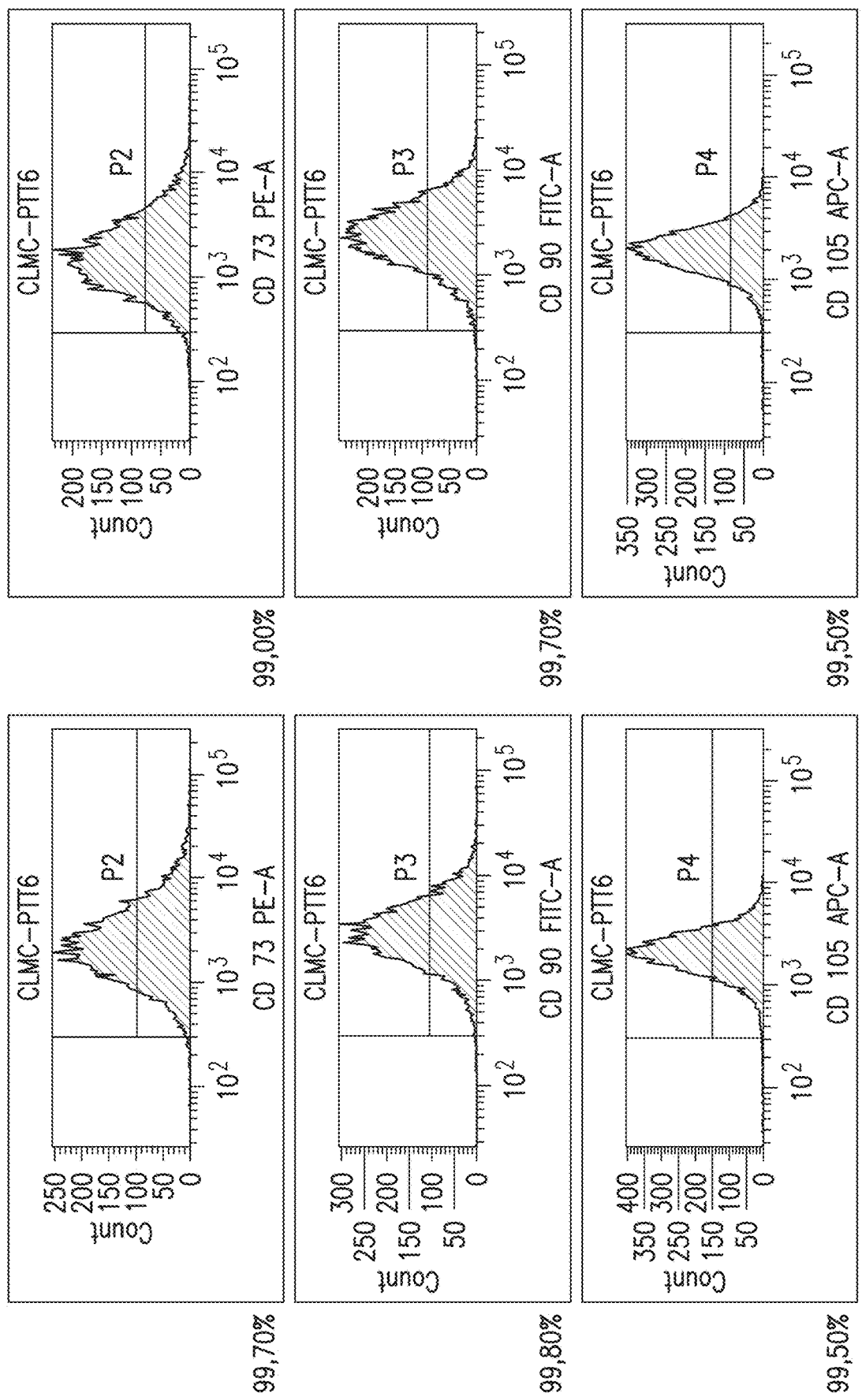

The results of the flow cytometry analysis are shown in FIG. 6a to FIG. 6c. FIG. 6a shows the percentage of isolated mesenchymal cord lining stem cells expressing stem cell markers CD73, CD90 and CD105 after isolation from umbilical cord tissue and cultivation in DMEM/10% FBS, FIG. 6b shows the percentage of isolated mesenchymal cord lining stem cells expressing stem cell markers CD73, CD90 and CD105 after isolation from umbilical cord tissue and cultivation in PTT-4 and FIG. 6c shows the percentage of isolated mesenchymal cord lining stem cells expressing stem cell markers CD73, CD90 and CD105 after isolation from umbilical cord tissue and cultivation in PTT-6. As can be seen from FIG. 6a, the population isolated using DMEM/10% FBS as culture medium cultivation has about 75% CD73+ cells, 78% CD90+ cells and 80% CD105+ cells (average of two experiments), while after isolation/cultivation of umbilical cord tissue using PTT-4 culture medium (see FIG. 6b) the number of mesenchymal stem cells that are CD73-positive, CD90-positive and CD105-positive are about 87% (CD73+ cells), 93%/CD90+ cells) and 86% (CD105+ cells) average of two experiments. The purity of the mesenchymal stem cell population that was obtained by means of cultivation in the PTT-6 medium of the present invention is at least 99.0% with respect to all three markers (CD73, CD90, CD105), meaning the purity of this cell population is significant higher than for cultivation using PTT-4 medium or DMEM/10% FBS. In addition and even more importantly, the mesenchymal stem cell population obtained by means of cultivation in PTT-6 is essentially a 100% pure and defined stem cell population. This makes the stem cell population of the present invention the ideal candidate for stem cell based therapies. Thus, this population of mesenchymal cord lining stem cells may become the gold standard for such stem cell based therapeutic approaches.

Figure 7A:
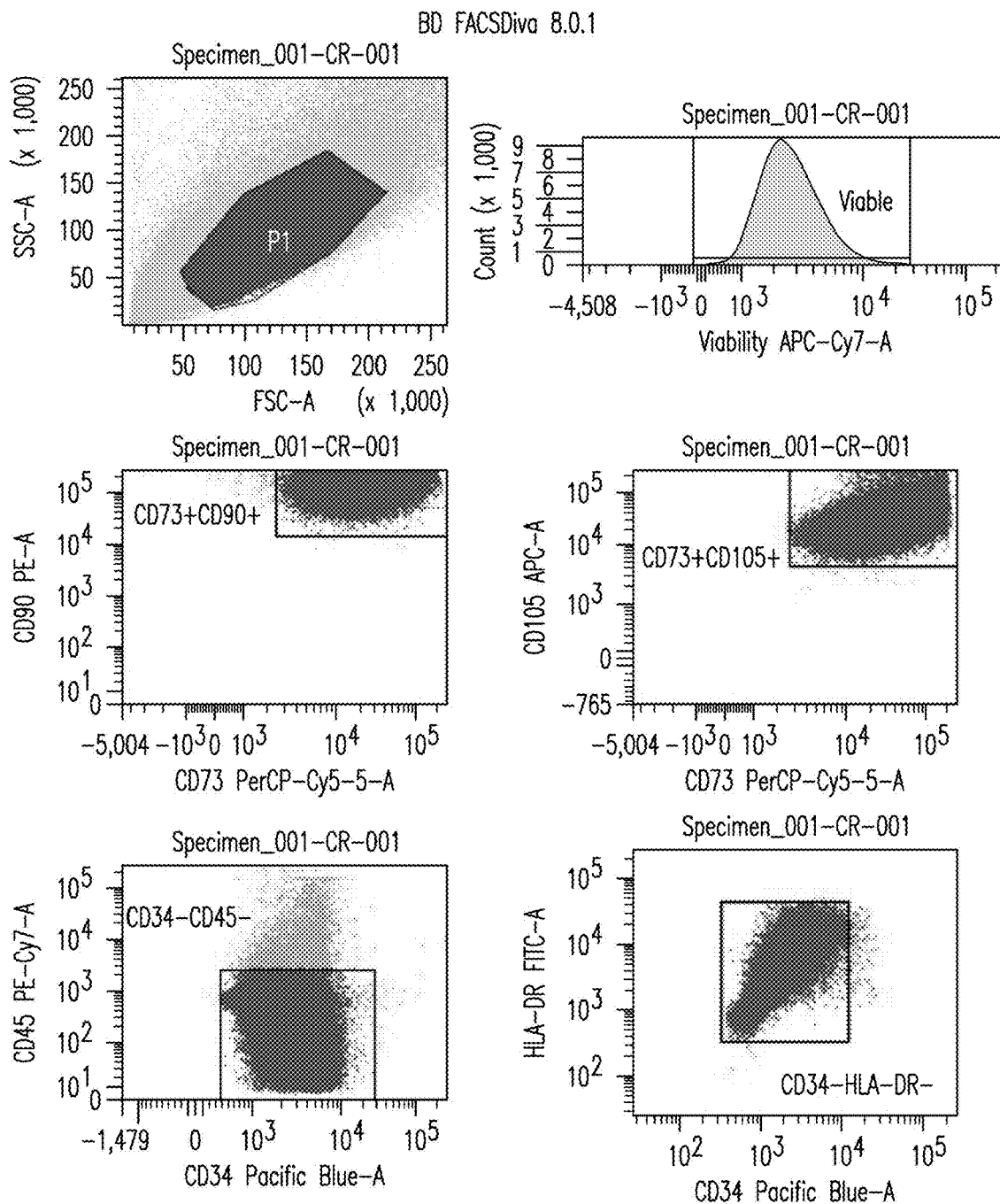
FIGS. 7A-7B show the results of flow, cytometry experiments in which mesenchymal stem cells isolated from the umbilical cord have been analysed for their expression of stem cells markers (CD73, CD90 and CD105, CD34, CD45 and HLA-DR (Human Leukocyte Antigen—antigen D Related) that are used for defining the suitability of multipotent human mesenchymal stem cells for cellular therapy and compared to the expression of these markers by bone marrow mesenchymal stem cells. For this experiment, the mesenchymal stem cells of the amniotic membrane of the umbilical cord were isolated from umbilical cord tissue by cultivation of the umbilical cord tissue in the culture medium of the present invention PTT-6 while the bone marrow mesenchymal stem cells were isolated from human bone marrow using a standard protocol.
Figure 7B:
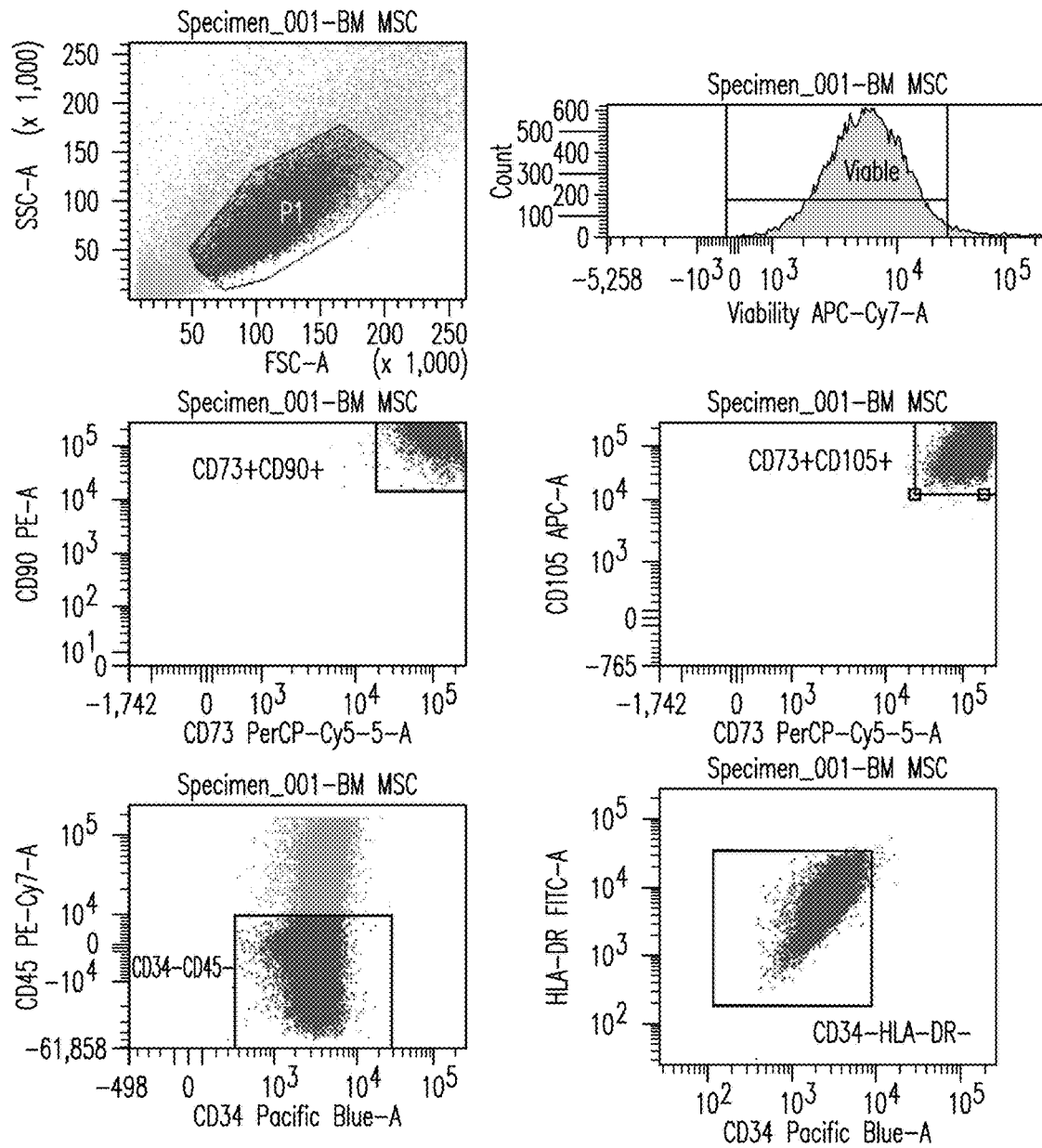

The findings shown in FIG. 6 are further corroborated by the results of the flow cytometry analysis that are shown in FIG. 7a and FIG. 7b. FIG. 7a shows the percentage of isolated mesenchymal cord lining stem cells (mesenchymal stem cells of the amniotic membrane of umbilical cord) that express the stem cell markers CD73, CD90 and CD105 and lack expression of CD34, CD45 and HLA-DR after isolation from umbilical cord tissue and cultivation in PTT-6 medium. As shown in FIG. 7a, the mesenchymal stem cell population contained 97.5% viable cells of which 100% expressed each of CD73, CD90 and CD105 (see the rows "CD73+CD90+" and "CD73+CD105+") while 99.2% of the stem cell population did not express CD45 and 100% of the stem cell population did not express CD34 and HLA-DR (see the rows "CD34−CD45− and "CD34-HLA-DR-). Thus, the mesenchymal stem cells population obtained by cultivation in PTT-6 medium is essentially a 100% pure and defined stein cell population that meets the criteria that mesenchymal stem cells are to fulfill to be used for cell therapy (95% or more of the stem cell population express CD73, CD90 and CD105, while 98% or more of the stem cell population lack expression of CD34, CD45 and HLA-DR, see Sensebe et al. "Production of mesenchymal stromal/stem cells according to good manufacturing practices: a review", supra). It is noted here that the present mesenchymal stem cells of the amniotic membrane adhere to plastic in standard culture conditions and differentiate in vitro into osteoblasts, adipocytes and chondroblasts, see U.S. Pat. No. 9,085,755, 8,287,854 or WO2007/046775 and thus meet the criteria generally accepted for use of mesenchymal stem cells in cellular therapy.

FIG. 7b shows the percentage of isolated bone marrow mesenchymal stem cells that express CD73, CD90 and CD105 and lack expression of CD34, CD45 and HLA-DR. As shown in FIG. 7b, the bone marrow mesenchymal stem cell population contained 94.3% viable cells of which 100% expressed each of CD73, CD90 and CD105 (see the rows "CD73+CD90+" and "CD73+CD105+") while only 62.8% of the bone marrow stem cell population lacked expression of CD45 and 99.9% of the stem cell population lacked expression CD34 and HLA-DR (see the rows "CD34−CD45− and "CD34-HLA-DR-). Thus, the bone marrow mesenchymal stem cells that are considered to be gold standard of mesenchymal stem cells are by far less homogenous/pure in terms of stem cell marker than the mesenchymal stem cells population (of the amniotic membrane of the umbilical cord) of the present application. This finding also shows that the stem cell population of the present invention may be the ideal candidate for stem cell based therapies and may become the gold standard for stem cell based therapeutic approaches.

Experiments Showing that the Mesenchymal Stem Cell Population of the Invention can be Transported/Stored in HypoThermosol™:

To analyze health and viability of the mesenchymal stem cells as described herein in different storage or transport carrier, two different carriers were compared to each other. Namely, the carrier HypoThermosol™-FRS was compared to the carrier PlasmaLyte-A. Both are commercially available. HypoThermosol™-FRS the product sheet of which is shown in FIG. 30 and its composition is described elsewhere herein. Each 100 mL PlasmaLyte contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2.3H_2O$); 37 mg of Potassium Chloride, USP (KCl); and 30 mg of Magnesium Chloride, USP ($MgCl_2.6H_2O$). PlasmaLyte does not contain antimicrobial agents. The pH of PlasmaLyte is adjusted with sodium hydroxide to 7.4 (6.5 to 8.0).

Figure 8:
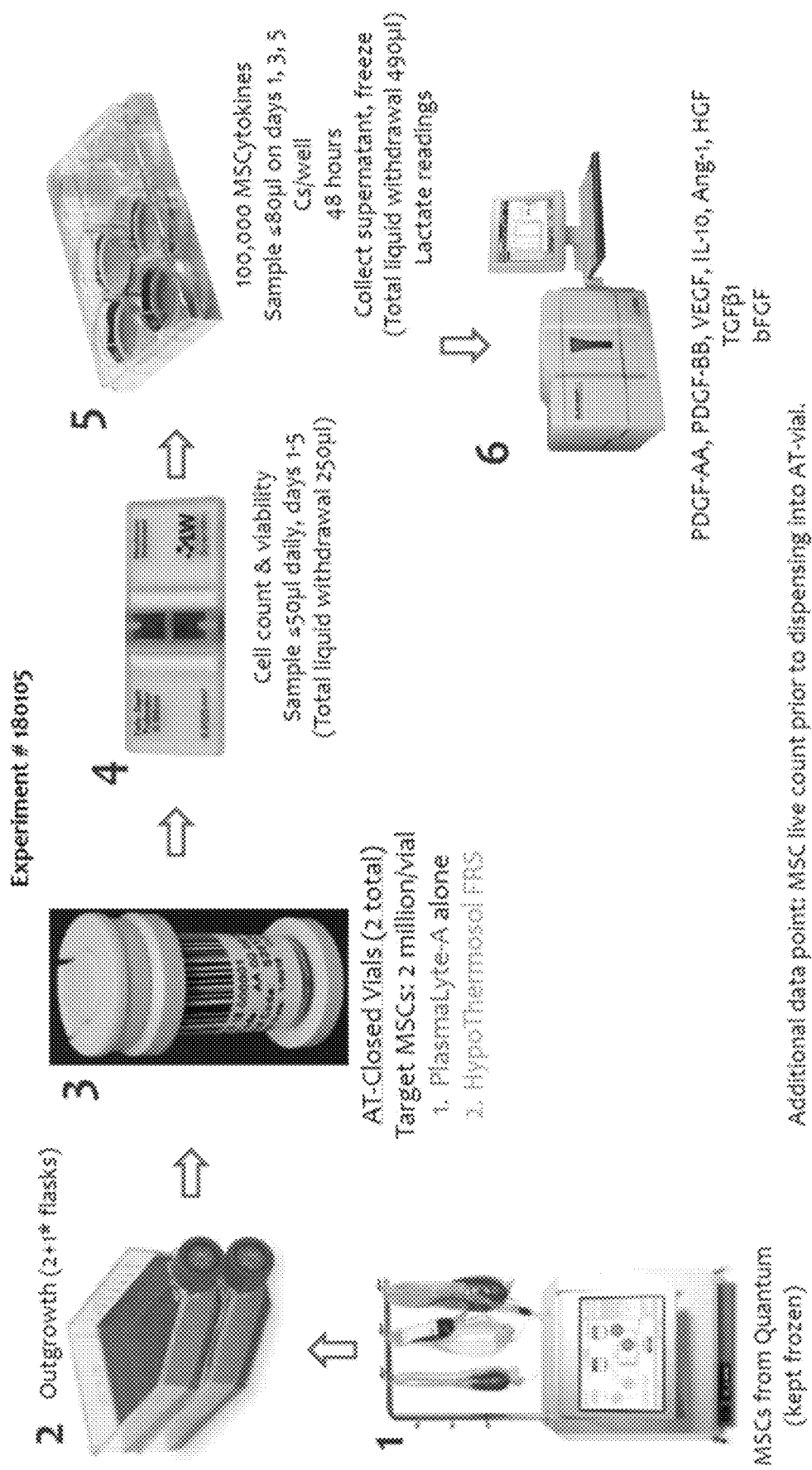
FIG. 8 shows the experimental setup for comparison of different carriers. First mesenchymal stem cell population as described herein were outgrown in cell culture flasks. The amount of living mesenchymal stem cells was counted and then 2 million cells/vial were stored for different periods of time in either PlasmaLyte-A or HypoThermosol™-FRS. After storage cells have been counted in sample of ≤50 μl daily for days 1-5 (Total liquid withdrawal 250 μl) and checked for viability by staining the cells with Trypan blue. Further, on days 1, 3 and 5 sample ≤80 μl were taken and analyzed. In addition, the supernatant was obtained and frozen. Then PDGF-AA, PDGF-BB, VEGF, IL-10, Ang-1, HGF and TGFβ1 were measured by FLEXMAP 3D system.

The experimental setup for comparison is shown in FIG. 8. First the mesenchymal stem cell population as described herein were outgrown in cell culture flasks. The number of living mesenchymal stem cells was counted and then 2 million cells/vial were stored for different periods of time in either PlasmaLyte-A or Hypothermosol™-FRS. After storage cells have been counted in sample of ≤50 μl daily for days 1-5 (total liquid withdrawal 250 μl) and checked for viability by staining the cells with Trypan blue. Further, on days 1, 3 and 5 sample ≤80 μl were taken and analyzed. In addition, the supernatant was obtained and frozen. Then PDGF-AA, PDGF-BB, VEGF, IL-10, Ang-1, HGF and TGFβ1 were measured by FLEXMAP 3D system.

Figure 9:
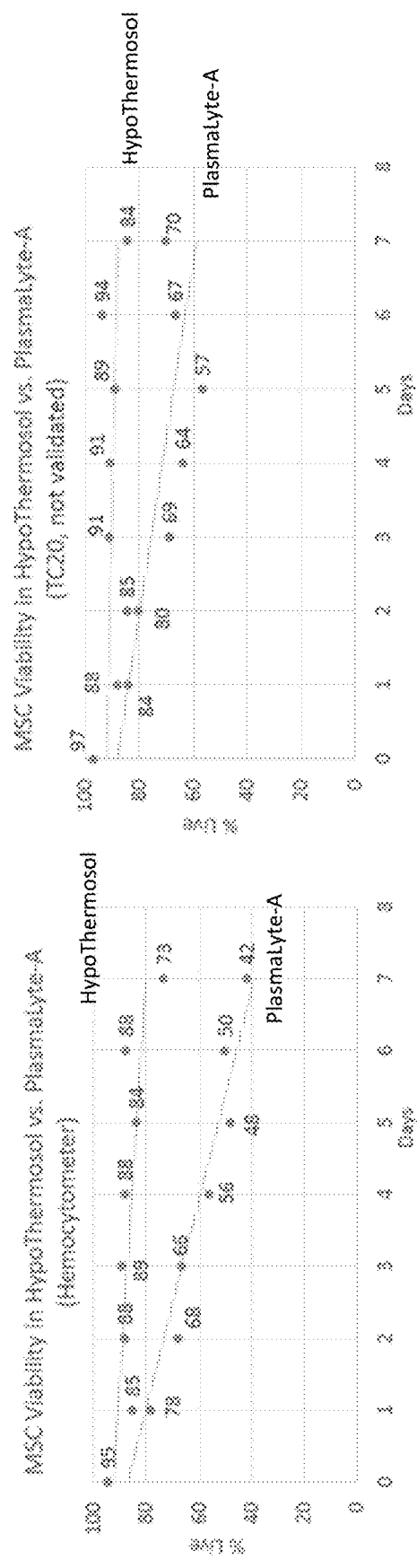
FIG. 9 summarizes viability data. As can be seen from the left-hand graph, 73% of the total number of cells (about 95%) when the storing started were still viable 7 days after storage in HypoThermosol™. On the contrary after 7 days of storage in PlasmaLyte-A only 42% of the total number of cells (about 94%) when the storage started were still viable. All counts were based on duplicate readings that are within 10% of one another (following SOP CR D2.600.1). During counting, cells stored in HypoThermosol™ were noticeably smaller with smooth and defined edges. By contrast, cells in Plasmalyte-A appeared in a range of sizes. HypoThermosol™ noticeably supports membrane integrity and presumably survival over a 6 day timespan. Similar results are also shown in the graph of the right-hand side.

FIG. 9 summarizes viability data. As can be seen from the left-hand graph, 73% of the total cells (about 95%) with which the storing started were still viable 7 days after storage in HypoThermosol™. On the contrary after 7 days of storage in PlasmaLyte-A only 42% of the total of cells (about 94%) with which the storage started were still viable. All counts based on duplicate readings that are within 10% of one another (following SOP CR D2.600.1). During counting, cells stored in HypoThermosol™ were noticeably smaller with smooth and defined edges. By contrast, cells in Plasmalyte-A appeared of a range of sizes. HypoThermosol™ noticeably supports membrane integrity and presumably survival over a week timespan (6 days). Similar results are also shown in the graph of the right-hand side.

Figure 10:
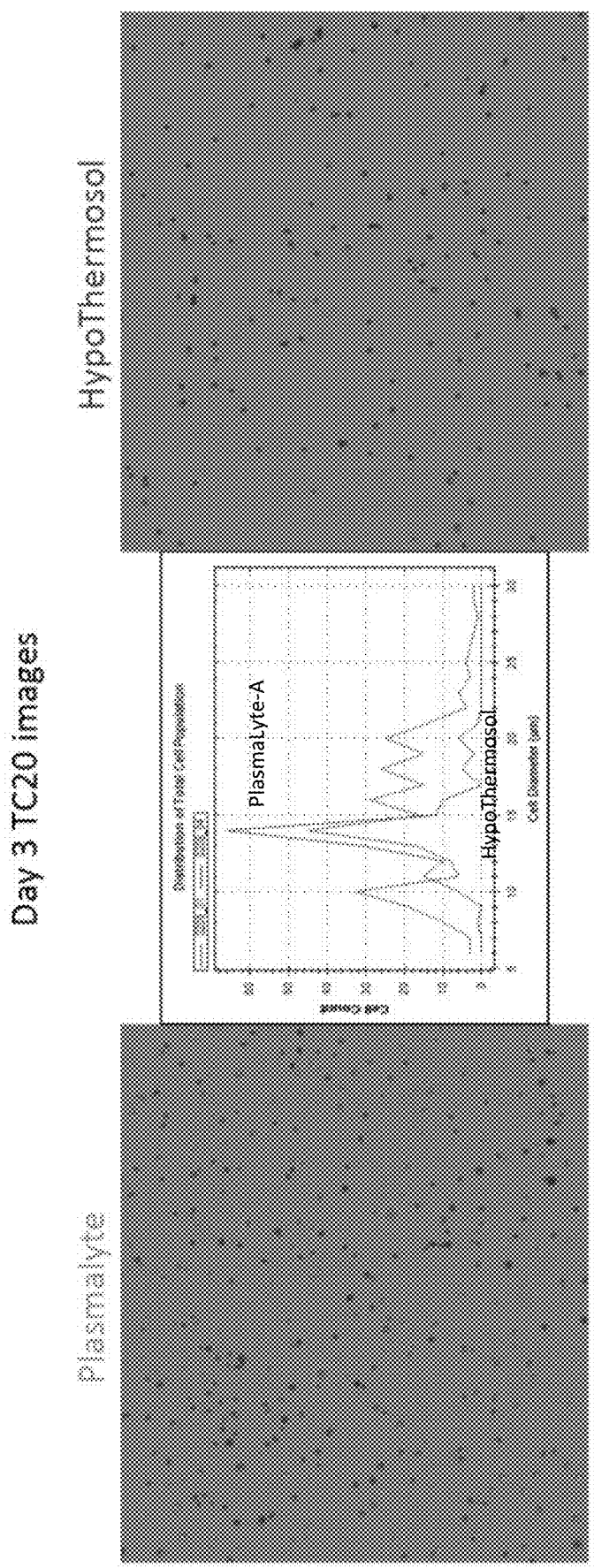
FIG. 10 shows the results obtained when measuring the cell diameter of cells. The mesenchymal stem cell population as described herein when kept in HypoThermosol™ are narrower in diameter range when compared to cells kept in PlasmaLyte-A. Comparison took place after 3 days of storage.

FIG. 10 shows the results obtained when measuring the cell diameter of cells. The mesenchymal stem cell population as described herein when kept in HypoThermosol™ are narrower in diameter range when compared to cells kept in PlasmaLyteA. Comparison took place after 3 days of storage.

Figure 11:
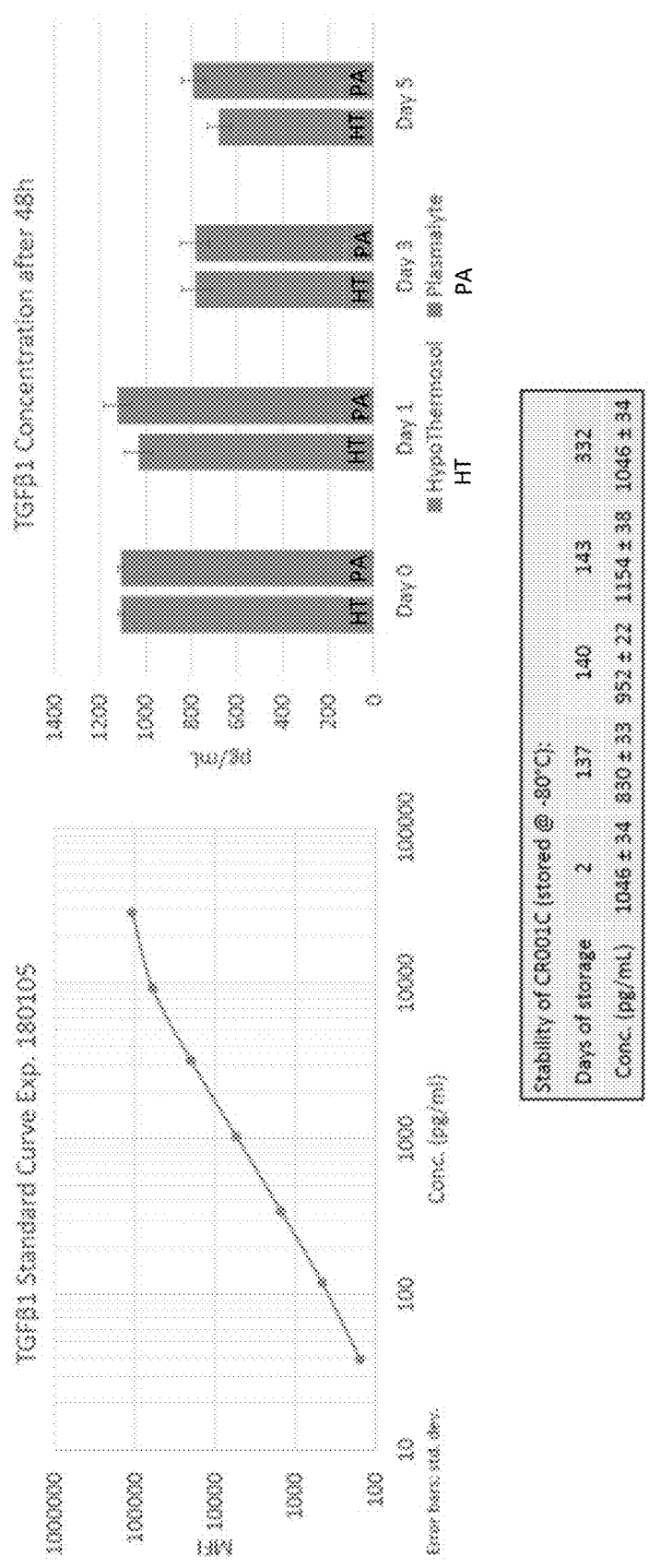
FIG. 11 shows the TGFß1 concentration in supernatant from the mesenchymal stem cell population as described herein stored in HypoThermosol™ or PlasmaLyte-A after 48 hrs of storage. As can be seen from the graph on the right-hand side, cells secrete about as much TGFß1 when stored in HypoThermosol™ as when stored in PlasmaLyte-A. In general, over time, the amount of secreted TGFß1 decreased (graph on the right hand side).

FIG. 11 shows the TGFβ1 concentration in supernatant from the mesenchymal stem cell population as described herein stored in HypoThermosol™ or PlasmaLyte-A after 48 hrs of storage. As can be seen from the graph on the right-hand side, cells secrete about as much TGFβ1 when stored in HypoThermosol™ and when stored in PlasmaLyte- A. In general, over time, the amount of secreted TGFß1 decreased (graph on the right hand side).

Figure 12:
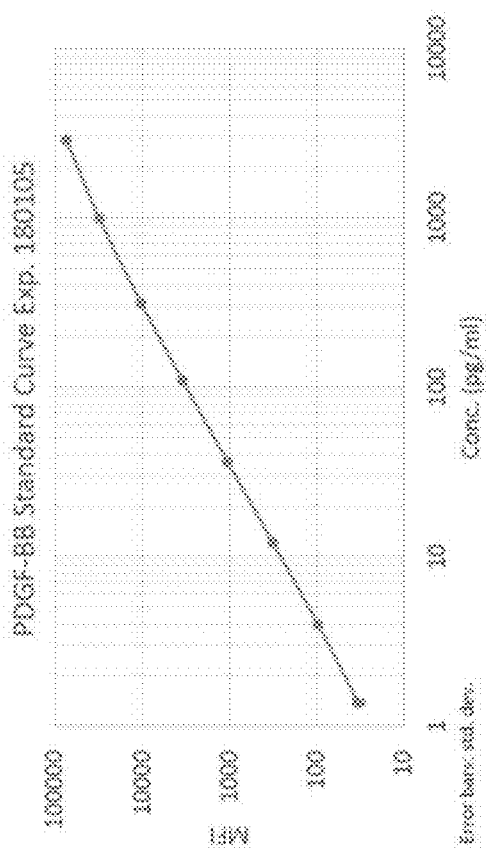
FIG. 12 shows control experiments. Here, the PDGF-BB concentrations were measured in supernatant from mesenchymal stem cell populations as described herein stored in HypoThermosol™ or PlasmaLyte-A for 48 hrs. Since PDGF-BB are not normally secreted by the mesenchymal stem cell population as described herein, no PDGF-BB were detectable in any sample.
Figure 13:
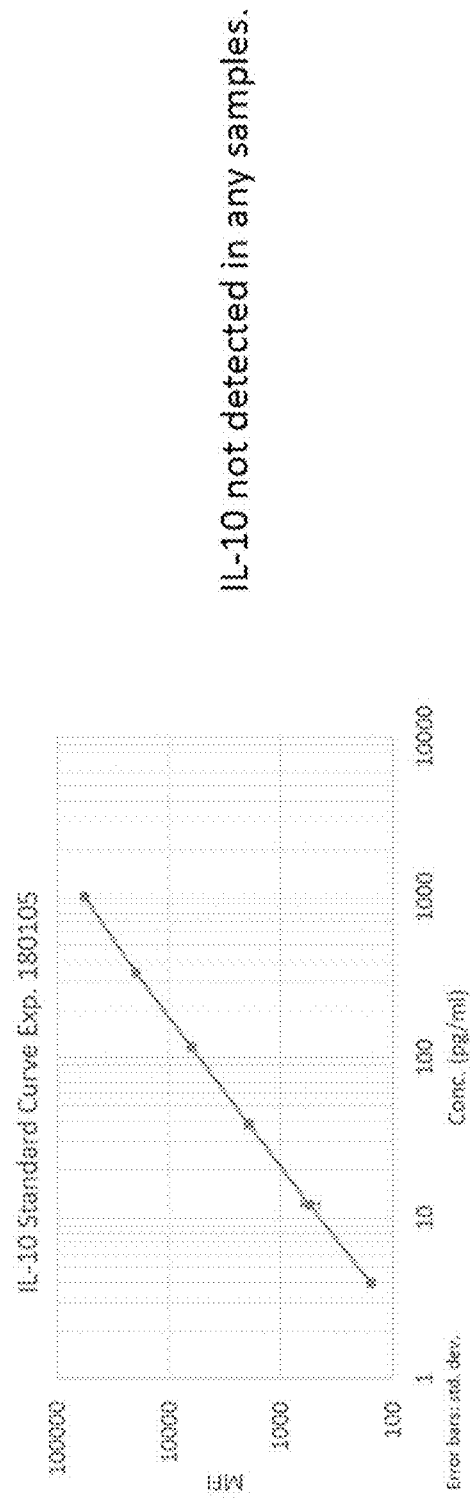
FIG. 13 shows control experiments. Here, the IL-10 concentrations were measured in supernatant from mesenchymal stem cell populations as described herein stored in HypoThermosol™ or PlasmaLyte-A for 48 hrs. Since IL-10 are not normally secreted by the mesenchymal stem cell population as described herein, no IL-10 were detectable in any sample.

FIGS. 12 and 13 show control experiments. Here, the PDGF-BB and IL-10 concentration was measured in supernatant from mesenchymal stem cell population as described herein stored in HypoThermosol™ or PlasmaLyte-A for 48 hrs. Since PDGF-BB or IL-10 are not normally secreted by the mesenchymal stem cell population as described herein, no PDGF-BB or IL-10 were detectable in any sample.

Figure 14:
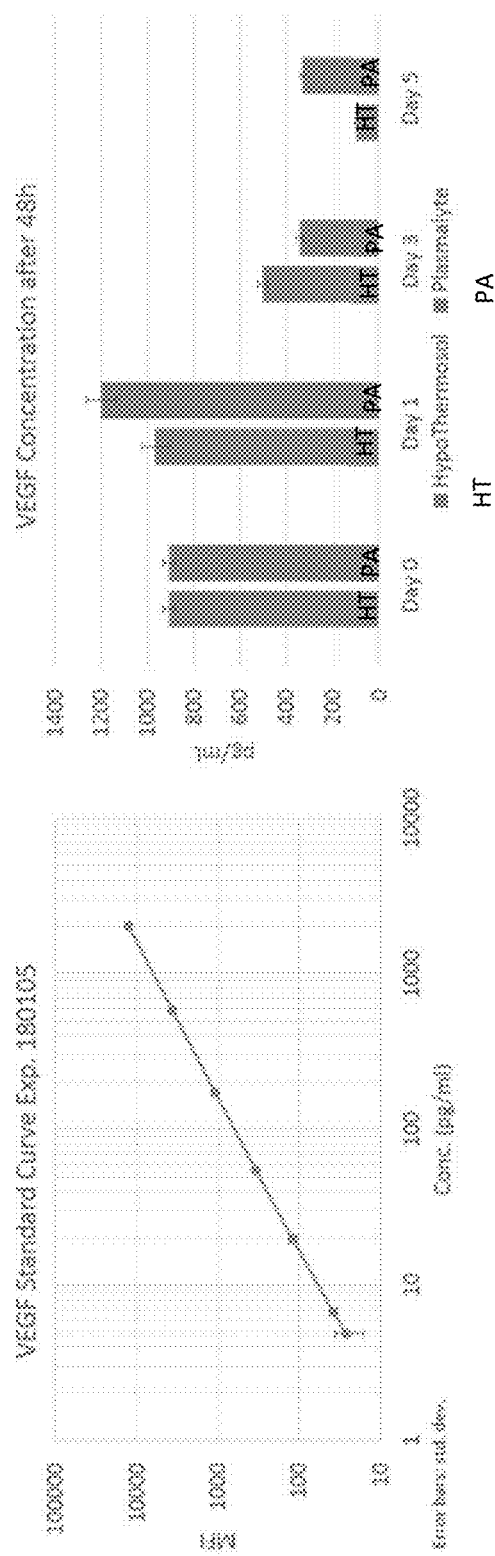
FIG. 14 shows the VEGF concentration in supernatant from mesenchymal stem cell populations as described herein stored in HypoThermosol™ or PlasmaLyte-A for 48 hrs. As can be seen from the graph on the right-hand side, cells secrete about as much VEGF when stored in HypoThermosol™ or PlasmaLyte-A on day 0. On day 1 and 5 cells secreted more VEGF when stored in PlasmaLyte-A. Notably, when stored for 3 days cells secreted more VEGF when stored in HypoThermosol™ than when stored in PlasmaLyte-A. Thus, HypoThermosol™ outperforms PlasmaLyte-A by day 3 of storage. The more VEGF detected, the healthier is the culture. Thus, by secreting more VEGF after 3 days storage in HypoThermosol™ than when stored in PlamsaLyte-A, cells were healthier in HypoThermosol™ than in PlamsaLyte-A. From 5 days, storage in PlasmaLyte seems to become more favourable, because at the time point cells stored in PlasmaLyte-A secreted more VEGF. In general, over time, the amount of secreted VEGF decreased (graph on the right hand side).

FIG. 14 shows the VEGF concentration in supernatant from mesenchymal stem cell population as described herein stored in HypoThermosol™ or PlasmaLyte-A for 48 hrs. As can be seen from the graph on the right-hand side, cells secrete about as much VEGF when stored in HypoThermosol™ or PlasmaLyte-A on day 0. On day 1 and 5 cells secreted more VEGF when stored in PlasmaLyte-A. Notably, when stored for 3 days cells secreted more VEGF when stored in HypoThermosol™ than when stored in PlasmaLyte-A. Thus, HypoThermosol™ outperforms PlasmaLyte-A after day 3 of storage. The more VEGF is detected the healthier is the culture. Thus, by secreting more VEGF after 3 days storage in HypoThermosol™ than when stored in PlasmaLyte-A, cells are healthier in HypoThermosol™ than in PlasmaLyte-A. From 5 days of storage onwards PlasmaLyte seems to become a more favourable carrier, because at the time point 5 days, cells stored in PlasmaLyte-A secreted more VEGF. In general, over time, the amount of secreted VEGF decreased (graph on the right hand side).

Figure 15:
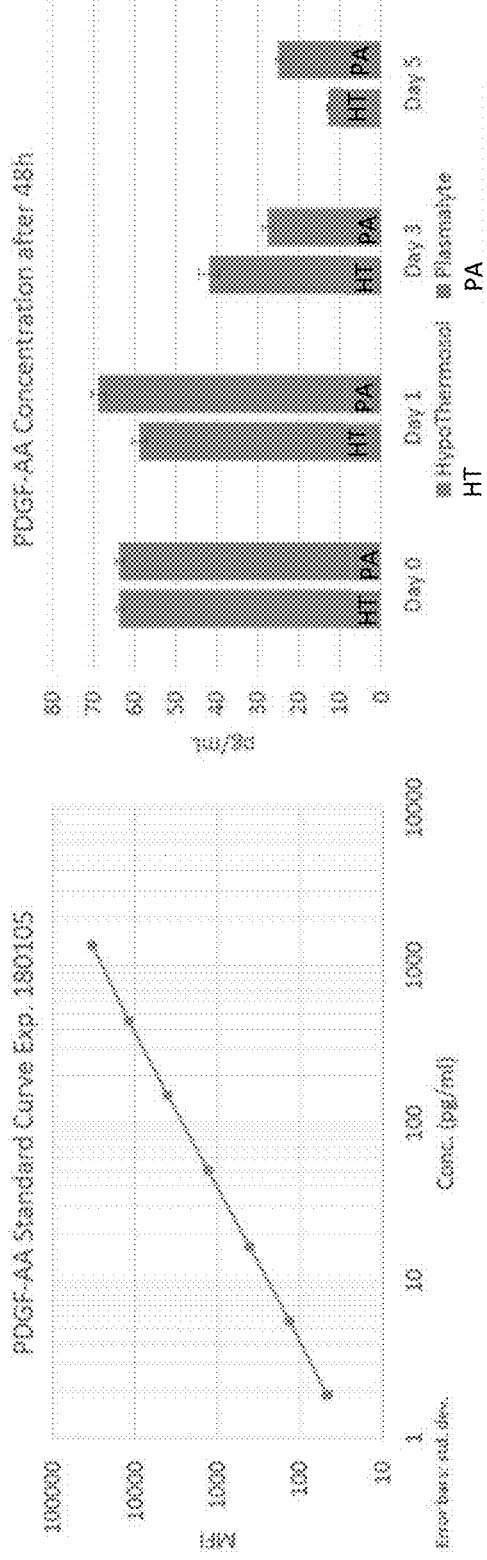
FIG. 15 shows the PDGF-AA concentration in supernatant from mesenchymal stem cell population as described herein stored in HypoThermosol™ or PlasmaLyte-A for 48 hrs. As can be seen from the graph on the right-hand side, cells secrete about as much PDGF-AA when stored in HypoThermosol™ as when stored in PlasmaLyte-A on day 0. On day 1 and 5 cells secreted more PDGF-AA when stored in PlasmaLyte-A. Notably, when stored for 3 days, cells secreted more PDGF-AA when stored in HypoThermosol™ than when stored in PlasmaLyte-A. Thus, cells stored in HypoThermosol™ are healthier than cells stored in PlasmaLyte-A after 3 days of storage. From 5 days of storage onwards, PlasmaLyte seems to become a more favourable carrier, because at the time point cells stored in PlasmaLyte-A secreted more PDGF-AA. In general, over time, the amount of secreted PDGF-AA decreased (graph on the right hand side).

FIG. 15 shows the PDGF-AA concentration in supernatant from mesenchymal stem cell population as described herein stored in HypoThermosol™ or PlasmaLyte-A for 48 hrs. As can be seen from the graph on the right-hand side, cells secrete about as much PDGF-AA when stored in HypoThermosol™ than when stored in PlasmaLyte-A on day 0. On day 1 and 5 cells secreted more PDGF-AA when stored in PlasmaLyte-A. Notably, when stored for 3 days cells, secreted more PDGF-AA when stored in HypoThermosol™ than when stored in PlasmaLyte-A. Thus, cells stored in HypoThermosol™ are healthier than cells stored in PlasmaLyte-A after 3 days of storage. From 5 days of storage onwards, PlasmaLyte seems to become a more favourable carrier, because at the time point 5 days cells stored in PlasmaLyte-A secreted more PDGF-AA. In general over time the amount of secreted PDGF-AA decreased (graph on the right hand side).

Figure 16:
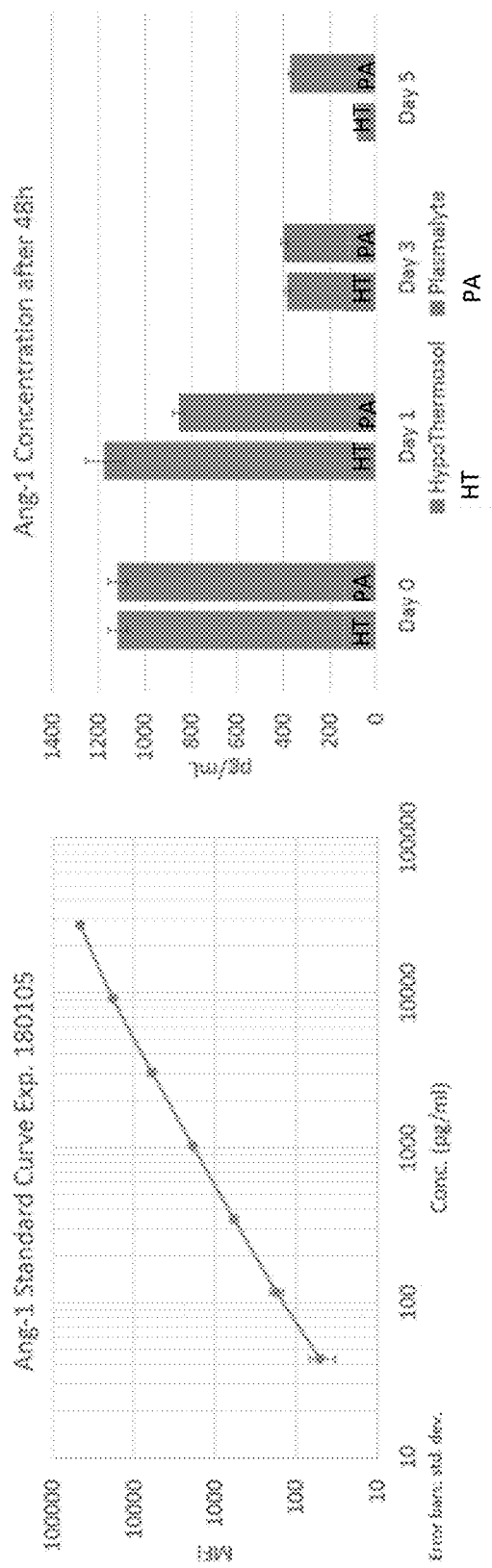
FIG. 16 shows the Ang-1 concentration in supernatant from mesenchymal stem cell populations as described herein stored in HypoThermosol™ or PlasmaLyte-A for 48 hrs. As can be seen from the graph on the right-hand side, cells secrete about as much Ang-1 when stored in HypoThermosol™ or PlasmaLyte-A on day 0 and 3. On day 5 cells secreted more Ang-1 when stored in PlasmaLyte-A. Noticably, when stored for 1 day, cells secreted much more Ang-1 when stored in HypoThermosol™ than when stored in PlasmaLyte-A. Thus, cells stored in Hypomermosol™ seem to be healthier than when stored in PlasmaLyte-A for at least 48 hrs until day 3 of storage. From day 5, PlasmaLyte seems to become a more favourable carrier, because at this time point cells stored in PlasmaLyte-A secreted more Ang-1. In general, over time, the amount of secreted Ang-1 decreased (graph on the right hand side).

FIG. 16 shows the Ang-1 concentration in supernatant from mesenchymal stem cell population as described herein stored in HypoThermosol™ or PlasmaLyte-A for 48 hrs. As can be seen from the graph on the right-hand side, cells secrete about as much Ang-1 when stored in HypoThermosol™ or PlasmaLyte-A on day 0 and 3. On day 5 cells secreted more Ang-1 when stored in PlasmaLyte-A. Notably, when stored for 1 day, cells secreted much more Ang-1 when stored in HypoThermosol™ than when stored in PlasmaLyte-A. Thus, cells stored in HypoThermosol™ seem to be healthier than when stored in PlasmaLyte-A for at least 48 hrs until 3 days of storage. From 5 days of storage onwards PlasmaLyte seems to become a more favourable carrier, because at this time point cells stored in PlasmaLyte-A secreted more Ang-1. In general, over time, the amount of secreted Ang-1 decreased (graph on the right hand side).

Figure 17:
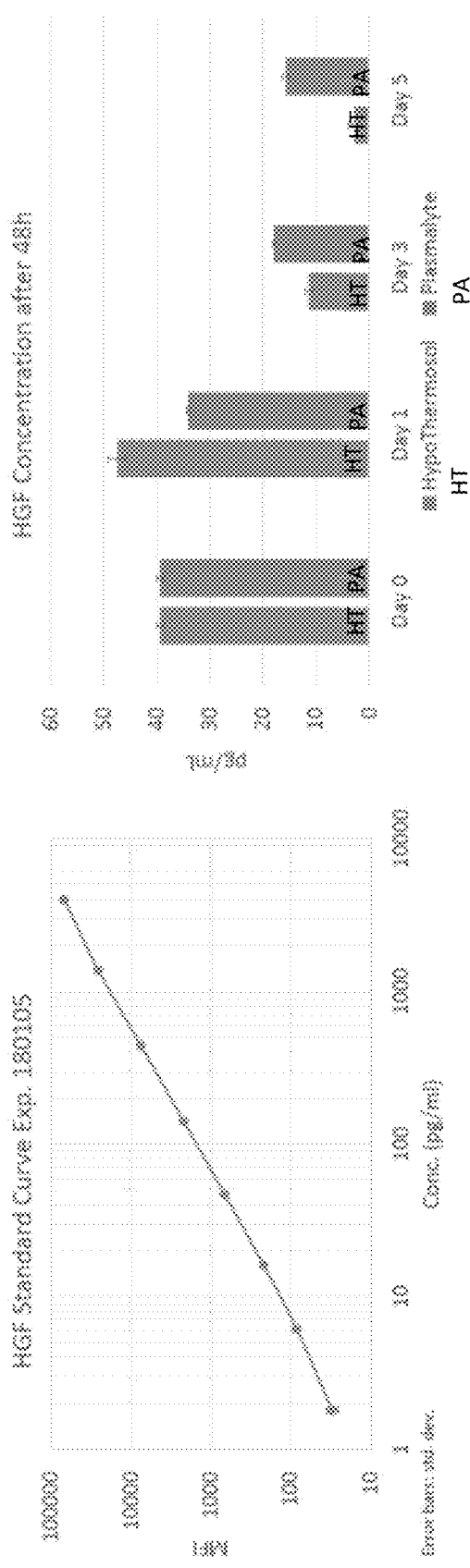
FIG. 17 shows the HGF concentration in supernatant from mesenchymal stem cell populations as described herein stored in HypoThermosol™ or PlasmaLyte-A after 48 hrs of storage. As can be seen from the graph on the right-hand side, cells secrete about as much HGF when stored in HypoThermosol™ than when stored in PlasmaLyte-A on day 0. On day 3 and 5 cells secreted more HGF when stored in PlasmaLyte-A. Notably when stored for 1 day, cells secreted much more HGF when stored in HypoThermosol™ than when stored in PlasmaLyte-A. Thus, cells stored in HypoThermosol™ seem to be healthier than cells stored in PlasmaLyte-A between at least 1 day (48 hrs) until 3 days of storage. From 3 days onwards PlasmaLyte-A seems to become a more favourable carrier, because at the time points 3 and 5 days, cells stored in PlasmaLyte-A secreted more HGF. In general, over time, the amount of secreted HGF decreased (graph on the right hand side).

FIG. 17 shows the HGF concentration in supernatant from mesenchymal stem cell population as described herein stored in HypoThermosol™ or PlasmaLyte-A after 48 hrs of storage. As can be seen from the graph on the right-hand side, cells secrete about as much HGF when stored in HypoThermosol™ than when stored in PlasmaLyte-A on day 0. On day 3 and 5 cells secreted more HGF when stored in PlasmaLyte-A. Notably, when stored for 1 day, cells secreted much more HGF when stored in HypoThermosol™ than when stored in PlasmaLyte-A. Thus, cells stored in HypoThermosol™ seem to be healthier than cells stored in PlasmaLyte-A between at least 1 day (48 hrs) until 3 days of storage. From 3 days on PlasmaLyte-A seems to become a more favourable carrier, because at the time points 3 and 5 days cells stored in PlasmaLyte-A secreted more HGF. In general, over time, the amount of secreted HGF decreased (graph on the right hand side).

In summary from the above data it can be concluded that storage of the mesenchymal stem cell population of the present invention in HypoThermosol™ outperforms storage in PlasmaLyte-A especially for the first 3 days of storage.

Figure 18:
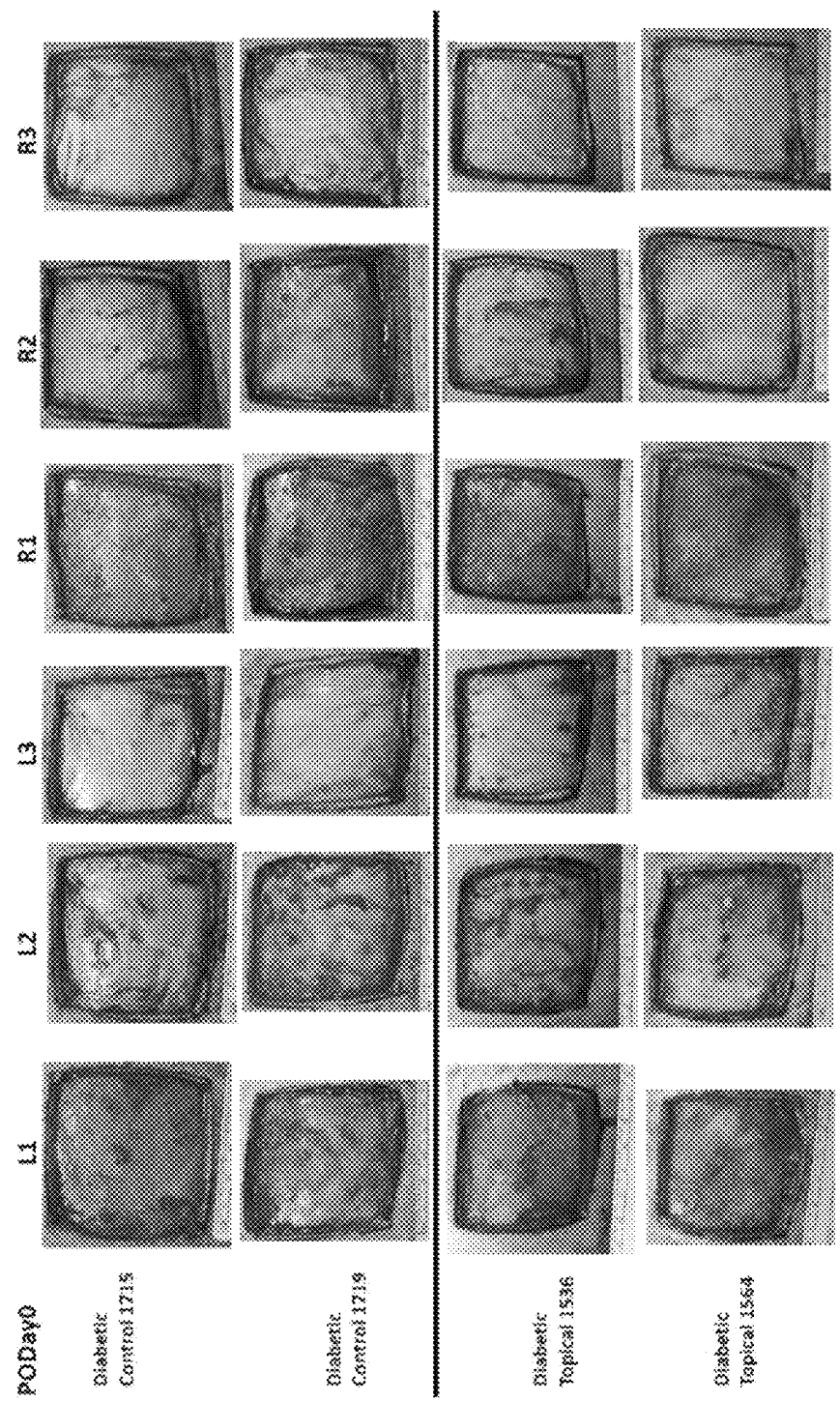
FIG. 18 are photographs obtained from a preclinical study with the mesenchymal stem cell population of the present invention in pigs. The pigs were rendered diabetic with 120 mg/kg streptozotocin and allowed to recover for 45 days prior to creating six 5 cm×5 cm full thickness wounds on their backs. Pigs (n=2) were treated twice weekly with $10^5$ human mesenchymal stem cell population as described herein per $cm^2$ for 4 weeks. The two control pigs were treated with PBS. Wounds were photographed on postoperative day 0 (PODay 0) and every seven days until postoperative Day 35. The wounds were analyzed for surface area size by ImageJ. By Day 35, the addition of mesenchymal stem cell population as described herein had resulted in closure of 10 of 12 diabetic wounds (83%), compared to only 3 of 12 (25%) of the PBS-treated control wounds. The rate of wound healing was 0.8 $cm^2$/day with the mesenchymal stem cell population as described herein compared to 0.6 $cm^2$/day in the control animals, an improvement of 33%.
Figure 18:
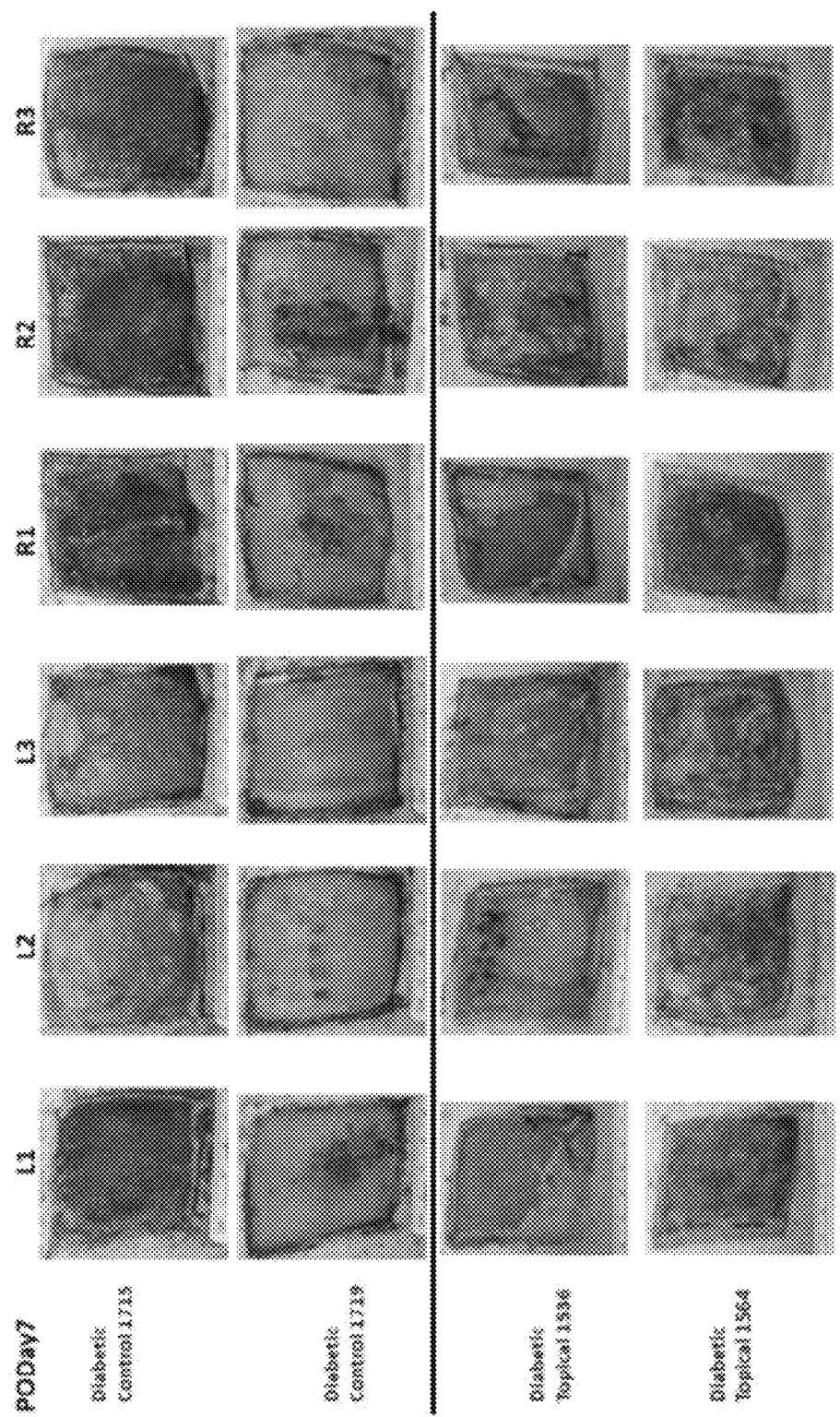
Figure 18:
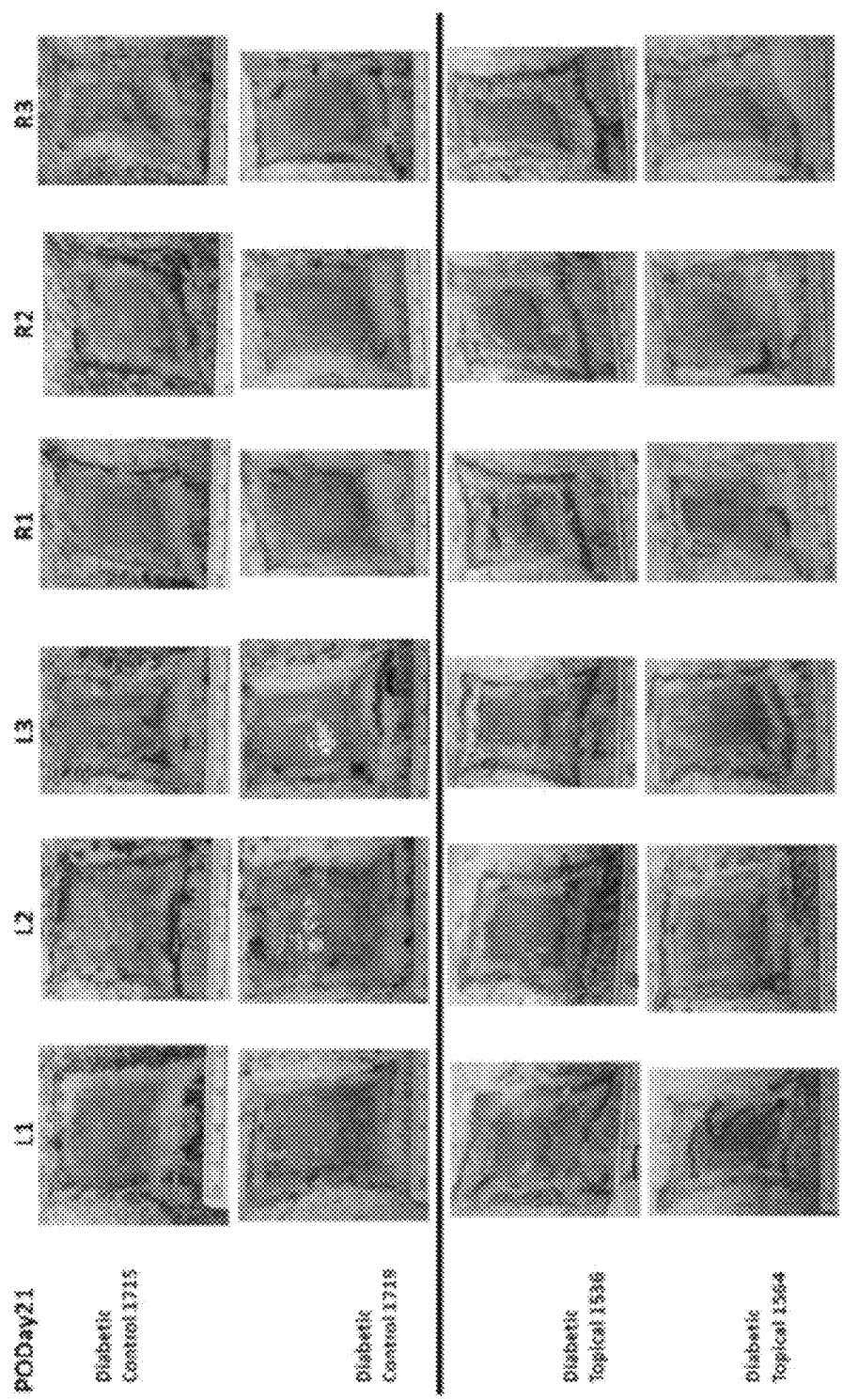
Figure 18:
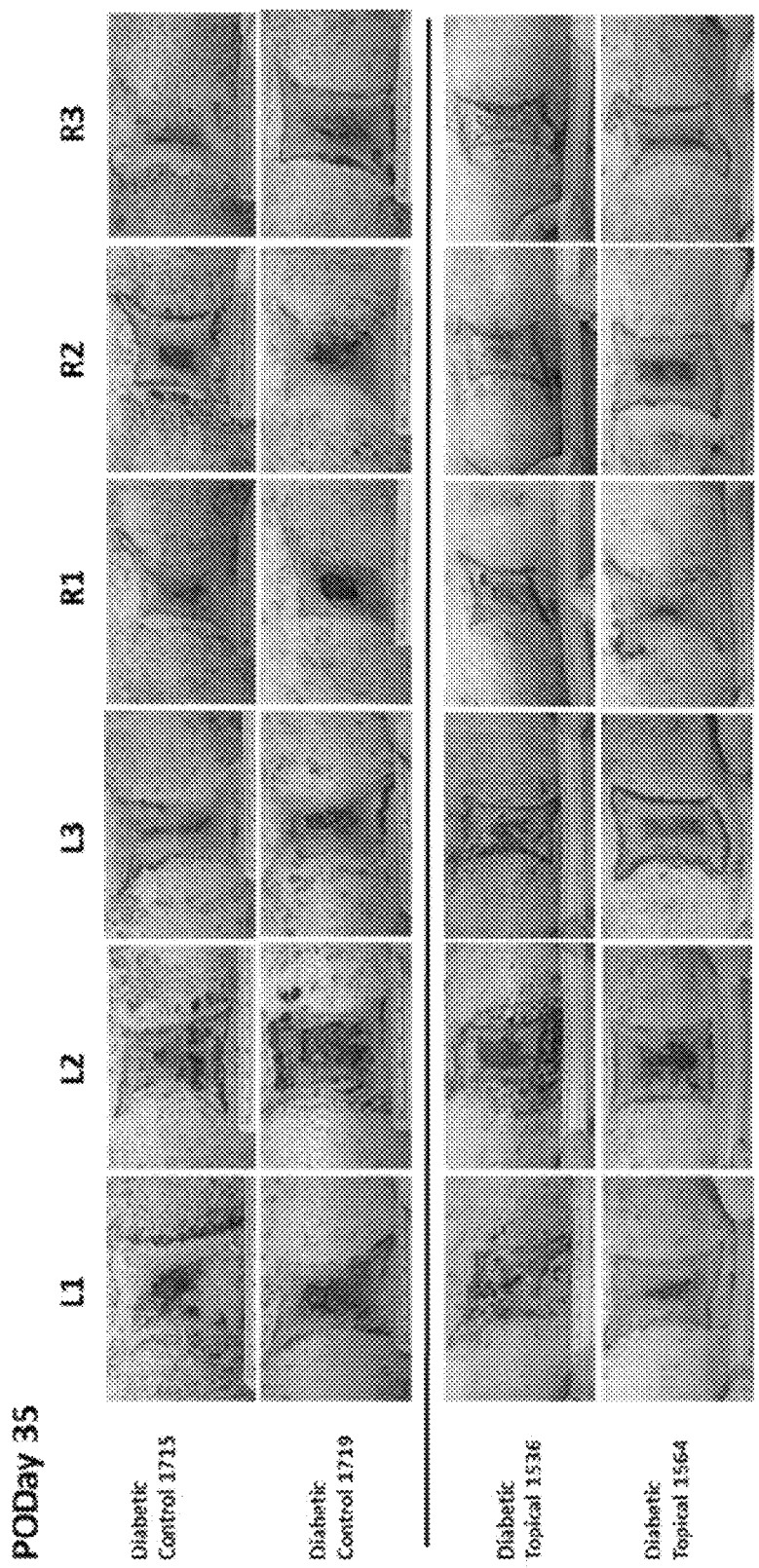

Experiments Showing that the Mesenchymal Stem Cell Population of the Invention have Wound Healing Properties by Topical Treatment of Pigs:

Preclinical studies have also been performed using 10-week old female Yorkshire-Landrace pigs (50 kg). The treatments were performed at SingHealth Experimental Medicine Centre in Singapore. The pigs were rendered diabetic with 120 mg/kg streptozotocin and allowed to recover for 45 days prior to creating six 5 cm×5 cm full thickness wounds on their backs (see FIG. 18). Pigs (n=2) were treated twice weekly with $10^5$ human mesenchymal stem cell population as described herein per $cm^2$ for 4 weeks. The two control pigs were treated with PBS. Wounds were photographed on postoperative day 0 (PODay 0) and every seven days until postoperative Day 35. The wounds were analyzed for surface area size by ImageJ. By Day 35, the addition of mesenchymal stem cell population as described herein had resulted in closure of 10 of 12 diabetic wounds (83%), compared to only 3 of 12 (25%) of the PBS-treated control wounds. The rate of wound healing was 0.8 $cm^2$/day with the mesenchymal stem cell population as described herein compared to 0.6 $cm^2$/day in the control animals, an improvement of 33%. Results of this study are summarized in FIG. 18.

The pig model is not spontaneous, but the skin architecture most closely resembles humans. The data suggest that umbilical cord lining mesenchymal stem cell population of the present invention will improve wound healing without the risk of serious adverse side effects. These data thus strongly support the hypothesis that human umbilical cord lining mesenchymal stem cell population as described herein can promote chronic wound healing by suppressing inflammation and promoting angiogenesis. Furthermore, there is clearly no sign of inflammation with the use of xenogeneic mesenchymal stem cells in either mice or pigs, and therefore the likelihood that allogeneic mesenchymal stem cells will have any serious adverse effect in humans is very low.

Experiments Showing that the Mesenchymal Stem Cells as Described Herein are Effective in Topical Treatments in Humans:

Experiments showing that the mesenchymal stem cells as described herein are effective in topical treatments in humans have been described in WO 2007/046775. In particular, as explained in Examples 23-26 of WO 2007/046775 mesenchymal stem cells of the amniotic membrane of the umbilical cord (UCMC) could alleviate full thickness burns (Example 23), partial-thickness wounds (Example 24), non-healing radiation wound (Example 25) as well as non-healing diabetic wound and non-healing diabetic foot wounds (Example 26). Notably, in accordance with Example 2 of WO 2007/046775 mesenchymal stem cells were resuspended in PTT-4 medium.

Notably, as depicted in FIGS. 6b and 6c the stem cell population obtained by cultivation when using PTT6 (as used herein) cultivation medium is significantly more homogenous than the population of cells obtained by using PTT4 medium (used in WO 2007/046775). Since PTT-4 was used as medium for mesenchymal stem cells in Examples 23-26 of WO 2007/046775 it is clear that the even more homogenous mesenchymal stem cell population isolated after cultivation in PTT-6 (as used herein) will have the same beneficial effects in wound healing applications, such as full thickness burns, partial-thickness wounds, non-healing radiation wound as well as non-healing diabetic wound and non-healing diabetic foot wounds.

Experiments Showing that the Mesenchymal Stem Cells as Described Herein are Effective in Topical Treatments in Humans:

This is a planned study of escalating doses of the mesenchymal stem cell population obtained as described herein performed at the University of Colorado Anschutz Medical Campus in Aurora, Colo. The goal of this study is to determine a safe dose of mesenchymal stem cell population as described herein (human umbilical cord lining mesenchymal stem cells). This is a single-center, dose-escalation study where each of three dose levels will enroll five subjects for a total of fifteen subjects. The first group of 5 patients will receive 100,000 MSC/cm$^2$ (skin/wound area) twice per week for 8 weeks. The second group of 5 patients will receive 300,000 MSC/cm$^2$ twice per week for 8 weeks. The third group of 5 patients will receive 500,000 MSC/cm$^2$ twice per week for 8 weeks. This schedule will continue until either the highest dose is reached, or until at least 2 subjects at a dose level have ≥Grade 2 allergic reaction that is suspected to be related to mesenchymal stem cell population as obtained herein or 2 or more subjects at a dose level experience an unexpected, treatment-related serious adverse event or dose limiting toxicity within 14 days following the initial dose of mesenchymal stem cell population as obtained as described herein. All of the patients will be evaluated 30 days posttreatment for the production of anti-HLA antibodies and for wound closure. At the present time, we do not consider production of HLA antibodies to be an absolute contraindication to a particular dose, but it will factor into our overall assessment of safety. This is an open-label study where all subjects will be taking the study drug and all study personnel will know the dose each subject receives. A secondary endpoint of this study will be significant improvement in the condition of the wound. This endpoint will be based on the rate of wound closure, the percent of wound area successfully closed, and the percent of wounds fully closed, as measured using the Silhouette Wound Measurement and Documentation System. This device is approved by the FDA for this purpose.

Subject Population. Patients with Type I or Type II diabetes with chronic foot ulcers that have not healed after at least 30 days of conventional therapy and are negative for HLA antibodies to the mesenchymal stem cell population as described herein. Patients will continue with conventional wound treatment for the first 2 weeks commencing at the time of enrollment, at which time they will have already been screened for having a diabetic foot ulcer that has not healed in 30 days. Photodocumentation and measurement of wound parameters will start at this time. Conventional dressing changes will be performed twice a week for the first 2 weeks, after which mesenchymal stem cell population as described herein will be applied to the wound at the specified concentrations twice a week. The mesenchymal stem cell population as described herein-treated wounds will also be covered with Tegaderm® and a crepe dressing.

Dose Levels. The goal of this study is to determine a safe dose of human umbilical cord lining mesenchymal stem cells as described herein for further study. Patients will be treated with one of three doses: 100,000 cells/cm$^2$ skin/wound area, 300,000 cells/cm$^2$ or 500,000 cells/cm$^2$ twice a week for 8 weeks. Each 100,000 cell dose represents 0.1 ml of the mesenchymal stem, cell population as described herein from a vial containing 1 million cells/ml in Hypo-Thermosol.

Dosing Regimen. This is a safety and tolerability study of escalating doses of mesenchymal stem cells as described herein. The goal of this study is to determine a safe dose of the human umbilical cord lining mesenchymal stem cells as described herein for further study. Each of three dose levels will enroll five subjects. The first group of 5 patients will receive 100,000 MSC/cm$^2$ skin/wound area twice per week for 8 weeks. The second group of 5 patients will receive 300,000 MSC/cm$^2$ twice per week for 8 weeks. The third group of 5 patients will receive 500,000 MSC/cm$^2$ twice per week for 8 weeks. This schedule will continue until either the highest dose is reached, or until at least 2 subjects at a dose level have ≥Grade 2 allergic reaction that is suspected to be related to mesenchymal stem cells as described herein or 2 or more subjects at a dose level experience an unexpected, treatment-related serious adverse event or dose limiting toxicity within 30 days following the initial dose of a mesenchymal stem cell population as described herein. All of the patients will be evaluated 30 days posttreatment for the production of anti-HLA antibodies and for degree of wound closure. At the present time, we do not consider production of HLA antibodies to be an absolute contraindication to a particular dose, but it will factor into our overall assessment of safety. This is an open-label study where all subjects will be taking the study drug and all study personnel will know the dose each subject receives.

Route of Administration. The mesenchymal stem cell population as described herein as described herein are applied topically to debrided diabetic foot ulcers and held in place by a Tegaderm® bandage.

Dosing Procedure. Following suitable debridement, if needed, the patient is placed in the prone position and the affected leg bent at a 90° angle. This vial of the mesenchymal stem cell population as described herein is gently swirled to ensure equal distribution of the cells. The elevated foot is then treated by removing 100,000 (0.1 ml) to 500,000 (0.5 ml) cells per cm$^2$ from the vial using a sterile syringe and placing it in the center of the wound. The wound is then sealed with a Tegaderm® membrane and gently massaged to distribute the cells evenly. The foot is maintained elevated for five minutes to allow the cells to settle and attach. The foot is then dressed with a crepe bandage to cover the Tegaderm® dressing.

The invention is further characterized by the following items:
1. A method of transporting a stem cell population, the method comprising transporting said stem cell population contacted with a liquid carrier, said liquid carrier comprising
   i) Trolox;
   ii) Na$^+$;
   iii) K$^+$;
   iv) Cl$^-$;
   v) H$_2$PO$_4^-$;

vi) HEPES;
vii) Lactobionate;
viii) Sucrose;
ix) Mannitol;
x) Glucose;
xi) Dextran-40;
xii) Adenosine, and
xiii) Glutathione.

2. The method of item 1, wherein the transporting is performed for about 7 days or less.

3. The method of item 1 or 2, wherein the transporting is performed for about 6 days, about 5 days, about 4 days, about 3 days, about 2 days, about 1 day or for less than about 1 day.

4. The method of any one of the preceding items, wherein the transporting is performed for about 48 hours or about 24 hours or less.

5. The method of any one of the foregoing items, wherein the transporting is performed at a temperature of about −5° C. to about 15° C.

6. The method of any one of the foregoing items, wherein the transporting is performed at a temperature of about 2° C. to about 8° C.

7. The method of any one of the foregoing items, wherein the transporting is carried out at a temperature of more than about −5° C., more than about −10° C., more than about −15° C., or more than about −20° C.

8. The method of any one of the foregoing items, wherein the stem cell population is transported in a concentration of about 70 million cells per 1 ml carrier, of about 60 million cells million cells per 1 ml carrier, of about 50 million cells per 1 ml carrier, of about 40 million cells per 1 ml carrier, of about 30 million cells per 1 ml carrier, of about 20 million cells per 1 nil carrier, of about 10 million cells per 1 ml carrier, of about 5 million cells per 1 ml carrier, of about 4 million cells per 1 nil carrier, of about 3 million cells per 1 ml carrier, of about 2 million cells per 1 ml carrier, of about 1 million cells per 1 ml carrier, of about 0.5 million cells per 1 ml carrier, of about 0.1 million cells per 1 ml carrier or of less than 0.1 million cells per 1 ml carrier.

9. The method of item 8, wherein the stem cell population is transported in a concentration of about 10 million cells per ml carrier to about 1 million cells per 1 ml carrier.

10. The method of any one of the foregoing items, wherein the stem cell population is an embryonic stem cell population, an adult stem cell population, a mesenchymal stem cell population or an induced pluripotent stem cell population.

11. The method of any one of the foregoing items, wherein the stem cell population is a mesenchymal stem cell population.

12. The method of any one of the foregoing items, wherein the mesenchymal stem cell population is an isolated mesenchymal stem population of the amniotic membrane of the umbilical cord.

13. The method of item 11 or 12, wherein at least about 90% or more cells of the isolated mesenchymal stem cell population express each of the following markers: CD73, CD90 and CD105.

14. The method of item 13, wherein at least about 91% or more, about 92% or more, about 93% or more, about 94% or more, about 95% or more, about 96% or more, about 97% or more, about 98% or more about 99% or more cells of the isolated mesenchymal stem cell population express each of CD73, CD90 and CD105.

15. The method of any one of items 11-14, wherein at least about 90% or more, about 91% or more, about 92% or more, about 93% or more, about 94% or more, about 95% or more, about 96% or more, about 97% or more, about 98% or more about 99% or more of the isolated mesenchymal stem cells lack expression of the following markers: CD34, CD45 and HLA-DR (Human Leukocyte Antigen-antigen D Related).

16. The method of any one of the foregoing items, wherein the stem cell population is contacted with the carrier before transporting.

17. The method of any one of the foregoing items, wherein the stem cell population is contacted with the carrier after its harvest.

18. The method of item 17, wherein the stem cell population is contacted with the carrier about 0 minutes, about 1 minute, about 5 minutes, about 10 minutes, about 30 minutes, about 45 minutes, about 60 minutes or a longer time after its harvest.

19. The method of item 17 or 18, wherein the harvest comprises separating the stem cell population from culture medium.

20. The method of item 19, wherein separating is performed by centrifuging the stem cells within a culture medium and decanting the culture medium.

21. The method of any one of the foregoing items, wherein the contacting is performed by suspending the stem cell population in a density of about 70 million/ml, of about 60 million/ml, of about 50 million/ml, of about 40 million/ml, of about 30 million/ml, of about 20 million/ml, of about 10 million/ml, of about 5 million/ml, of about 4 million/ml, of about 3 million/ml, of about 2 million/ml, of about 1 million/ml, of about 0.5 million/ml, of about 0.1 million/ml or of less than 0.1 million cells in the carrier.

22. The method of item 21, wherein the contacting is performed by suspending the stem cell population in a density of about 10 million/ml in the carrier.

23. The method of item 21 or 22, wherein the stem cells contacted with the carrier are aliquoted into vials in a volume of about 50 ml, of about 20 ml, of about 10 ml, of about 5 ml, of about 4 ml, of about 3 ml, of about 2 ml, of about 1 ml, of about 0.5 ml, of about 0.25 ml or of less than 0.25 ml carrier.

24. The method of item 21 or 22, wherein the stem cells contacted with the carrier are aliquoted into vials in an amount of about 1 ml.

25. The method of any one of the foregoing items, wherein the carrier is a transport medium or an excipient.

26. The method of any one of the foregoing items, wherein the method does not comprise a thawing or freezing step.

27. The method of any one of the foregoing items, wherein the carrier does not include a dipolar aprotic solvent, in particular DMSO.

28. The method of any one of the foregoing items, wherein at most about 50%, about 40%, about 30%, about 20%, about 10% or less than about 10% of the stem cells of the population die during transporting compared to the amount of viable stem cells before transporting.

29. The method of any one of the foregoing items, wherein most of the stem cells in the stem cell population have a cell diameter between about 9 μm and about 20 μm after transporting.

30. The method of any one of the foregoing items, wherein most of the stem cells in the stem cell population have a cell diameter between about 12 μm and about 16 μm after transporting.

31. The method of any one of the foregoing items, wherein after transport the stem cell population secretes about as much TGFbeta-1 as before transporting.
32. The method of any one of the foregoing items, wherein essentially no PDGF-BB and/or IL-10 is detected before and/or after transporting.
33. The method of any one of the foregoing items, wherein after transporting the mesenchymal stem cell population secretes about as much VEGF, PDGF-AA, Ang-1, and/or HGF as before transporting.
34. A method of treating a subject having a disease, the method comprising topically administering a mesenchymal stem cell population as defined in any one of items 12-15 to the subject, wherein the mesenchymal stem cell population is administered within about 96 hours from the time point the mesenchymal stem cell population has been harvested.
35. The method of item 34, wherein the mesenchymal stem cell population is applied in a unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells.
36. The method of item 34 or 35, wherein the mesenchymal stem cell population is applied in a unit dosage of about 10 million cells.
37. The method of any one of items 34-36, wherein the mesenchymal stem cell population is applied within about 72 hours, about 48 hours, about 24 hours, about 12 hours, about 6 hours or less from the time point the mesenchymal stem cell population has been harvested.
38. The method of any one of items 34-37, wherein the disease is a skin disease or a wound.
39. The method of item 38, wherein the wound is caused by a burn, a bite, a trauma, a surgery, or a disease.
40. The method of item 39, wherein the wound is caused by diabetic disease, wherein the wound is preferably a diabetic wound.
41. The method of item 40, wherein the wound is diabetic foot ulcer.
42. The method of any of items 34 to 41, wherein the unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells is administered once or twice a week.
43. The method of item 42, wherein the unit dosage of about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells is administered one of twice a week for a period of time of three weeks, of four weeks, or five weeks or of six weeks, or of seven weeks, or of eight weeks or of ten weeks or more weeks.
44. The method of any one of items 34-43, wherein the mesenchymal stem cell population is applied topically and covered by a film or bandage.
45. The method of any one of items 34-44, wherein the mesenchymal stem cell population is applied in a dosage of about 1000 cells/cm$^2$ to about 5 million cells/cm$^2$.
46. The method of any one of items 34-45, wherein the mesenchymal stem cell population is applied in a dosage of about 100,000 cells/cm$^2$, of about 300,000 cells/cm$^2$ or of about 500,000 cells/cm$^2$.
47. The method of any one of items 34-46, wherein the mesenchymal stem cell population is applied once, twice or more times a week.
48. The method of any one of items 34-47, wherein the mesenchymal stem cell population is applied for one, two, three, four, five, six, seven, eight, nine, ten, elven weeks or more.
49. The method of any one of items 34-48, wherein the mesenchymal stem cell population is applied two times a week for about 8 weeks in a dosage of about 100,000 cells/cm$^2$, about 300,000 cells/cm$^2$ or about 500,000 cells/cm$^2$.
50. The method of any of items 34 to 49, wherein the mesenchymal stem cell population is administered to the subject after separating the mesenchymal stem cell population from the carrier.
51. The method of item 50, wherein separating the mesenchymal stem cell population from the carrier comprises centrifugation.
52. The method of item 50 and 51, separating the mesenchymal stem cell population from the carrier comprises withdrawing the cell population from the vial by means of syringe.
53. The method of any of items 34 to 52, comprising administering the mesenchymal stem cell population by means of a syringe.
54. A unit dosage comprising about 20 million cells, of about 15 million cells, of about 10 million cells, of about 5 million cells, of about 4 million cells, of about 3 million cells, of about 2 million cells, of about 1 million cells, of about 0.5 million cells, of about 0.25 million cells or of less than 0.25 million cells of a mesenchymal stem cell population as defined in any one of items 12-15.
55. The unit dosage of item 54, wherein the unit dosage comprises about 10, about 9, about 8, about 7, about 6, about 5, about 4, about 3, about 2, about 1, about 0.5, about 0.25, or about 0.1 million cells.
56. The unit dosage of item 54 or 55, wherein the unit dosage comprises about 10 million cells.
57. The unit dosage of any one of items 54-56, wherein the unit dosage comprises about 1000 cells to about 5 million cells.
58. The unit dosage of any one of items 54-57, wherein the unit dosage is applied in a dosage of about 100,000 cells, 300,000 cells or 500,000 cells.
59. The unit dosage of any one of items 54-58, wherein the unit dosage is applied topically.
60. The unit dosage of any one of items 54-59, wherein the unit dosage is applied topically per cm$^2$.
61. The unit dosage of any one of items 54-60, wherein the unit dosage is applied once, twice, three times or more times a week.
62. The unit dosage of any one of items 54-61, wherein the unit dosage is applied for one, two, three, four, five, six, seven, eight, nine, ten, eleven weeks or more.
63. The unit dosage of any one of items 54-62, wherein the unit dosage comprises of about 100,000 cells, about 300,000 cells or about 500,000 cells of any one of items is applied two times a week for 8 weeks.
64. The unit dosage of any one of items 54-63, wherein the unit dosage is contained in a 1 ml vial.
65. The unit dosage of item 64, wherein 0.1 ml of the vial are applied.

66. The unit dosage of any one of items 54 to 65, wherein the cells are in contact with a liquid carrier as defined in item 1.
67. The unit dosage of any one of items 54 to 66, wherein the cells are centrifuged and isolated before administration to a subject.
68. The unit dosage of any one of items 54 to 67, wherein the carrier is HypoThermosol™.
69. The method of any of items 34 to 53 and the unit dosage of any one of items 54-68 wherein the cells are viable cells.
70. The method of any of items 1 to 33, wherein the carrier is HypoThermosol.
71. The use of a liquid carrier for transporting a stem cell population, wherein the liquid carrier comprises
   i) Trolox;
   ii) Na+;
   iii) K+;
   iv) Cl−;
   v) H2PO4−;
   vi) HEPES;
   vii) Lactobionate;
   viii) Sucrose;
   ix) Mannitol;
   x) Glucose;
   xi) Dextran-40;
   xii) Adenosine, and
   xiii) Glutathione.
72. The use of item 71, wherein the transporting is performed for about 7 days or less.
73. The use of item 71 or 72, wherein the transporting is performed for about 6 days, about 5 days, about 4 days, about 3 days, about 2 days, about 1 day or for less than about 1 day.
74. The use of any one of the preceding items 71 to 73, wherein the transporting is performed for about 48 hours or about 24 hours or less.
75. The use of any one of the foregoing items 71 to 74, wherein the transporting is performed at a temperature of about −5° C. to about 15° C.
76. The use of any one of the foregoing items 71 to 75, wherein the transporting is performed at a temperature of about 2° C. to about 8° C.
77. The use of any one of the foregoing items 71 to 76, wherein the transporting is carried out at a temperature of more than about −5° C., more than about −10° C., more than about −15° C., or more than about −20° C.
78. The use of any one of the foregoing items 71 to 77, wherein the stem cell population is transported in a concentration of about 70 million cells per 1 ml carrier, of about 60 million cells million cells per 1 ml carrier, of about 50 million cells per 1 ml carrier, of about 40 million cells per 1 ml carrier, of about 30 million cells per 1 ml carrier, of about 20 million cells per 1 ml carrier, of about 10 million cells per 1 ml carrier, of about 5 million cells per 1 ml carrier, of about 4 million cells per 1 ml carrier, of about 3 million cells per 1 ml carrier, of about 2 million cells per 1 ml carrier, of about 1 million cells per 1 ml carrier, of about 0.5 million cells per 1 ml carrier, of about 0.1 million cells per 1 ml carrier or of less than 0.1 million cells per 1 ml carrier.
79. The use of item 78, wherein the stem cell population is transported in a concentration of about 10 million cells per 1 ml carrier to about 1 million cells per 1 ml carrier.
80. The use of any one of the foregoing items 71 to 79, wherein the stem cell population is an embryonic stem cell population, an adult stem cell population, a mesenchymal stem cell population or an induced pluripotent stem cell population.
81. The use of any one of the foregoing items 71 to 80, wherein the stem cell population is a mesenchymal stem cell population.
82. The use of any one of the foregoing items 71 to 81, wherein the mesenchymal stem cell population is an isolated mesenchymal stem population of the amniotic membrane of the umbilical cord.
83. The use of item 81 or 82, wherein at least about 90% or more cells of the isolated mesenchymal stem cell population express each of the following markers: CD73, CD90 and CD105.
84. The use of item 83, wherein at least about 91% or more, about 92% or more, about 93% or more, about 94% or more, about 95% or more, about 96% or more, about 97% or more, about 98% or more about 99% or more cells of the isolated mesenchymal stem cell population express each of CD73, CD90 and CD105.
85. The use of any one of items 81-84, wherein at least about 90% or more, about 91% or more, about 92% or more, about 93% or more, about 94% or more, about 95% or more, about 96% or more, about 97% or more, about 98% or more about 99% or more of the isolated mesenchymal stem cells lack expression of the following markers: CD34, CD45 and HLA-DR (Human Leukocyte Antigen-antigen D Related).
86. The use of any one of the foregoing items 71 to 85, wherein the stem cell population is contacted with the carrier before transporting.
87. The use of any one of the foregoing items 71 to 86, wherein the stem cell population is contacted with the carrier after its harvest.
88. The use of item 87, wherein the stem cell population is contacted with the carrier about 0 minutes, about 1 minute, about 5 minutes, about 10 minutes, about 30 minutes, about 45 minutes, about 60 minutes or a longer time after its harvest.
89. The use of item 87 or 88, wherein the harvest comprises separating the stem cell population from culture medium.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

When used herein, the term "about" is understood to mean that there can be variation in the respective value or range (such as pH, concentration, percentage, molarity, number of amino acids, time etc.) that can be up to 5%, up to 10%, up to 15% or up to and including 20% of the given value. For example, if a formulation comprises about 5 mg/ml of a compound, this is understood to mean that a formulation can have between 4 and 6 mg/ml, preferably between 4.25 and 5.75 mg/ml, more preferably between 4.5 and 5.5 mg/ml and even more preferably between 4.75 and 5.25 mg/ml, with the most preferred being 5 mg/ml. As used herein, an interval which is defined as "(from) X to Y" equates with an interval which is defined as "between X and Y". Both intervals specifically include the upper limit and also the lower limit. This means that for example an interval of "5 mg/ml to 10 mg/ml" or "between 5 mg/ml and 10 mg/ml" includes a concentration of 5, 6, 7, 8, 9, and 10 mg/ml as well as any given intermediate value.

What is claimed is:

1. A method of treating a subject having a disease, wherein the disease is a skin disease or a wound, the method comprising:
   a) isolating a human mesenchymal stem cell population from an amniotic membrane of human umbilical tissue by cultivating the amniotic membrane as a tissue explant in a culture medium comprising:
   DMEM in the final concentration of about 55 to 65% (v/v),
   F12 in a final concentration of about 5 to 15% (v/v),
   M171 in a final concentration of about 15 to 30% (v/v), and
   fetal bovine serum (FBS) in a final concentration of about 1 to 8% (v/v), and
   b) harvesting cells that have outgrown from the amniotic membrane during the cultivating step to provide primary isolated mesenchymal stem cells;
   c) subculturing the primary isolated mesenchymal stem cells in the culture medium, thereby providing the human mesenchymal stem cell population, wherein at least 97% cells of the isolated human mesenchymal stem cell population express each of CD73, CD90 and CD105 and lack expression of the following markers: CD34, CD45 and HLA•DR (Human Leukocyte Antigen-antigen D Related); and
   d) topically administering to the subject a therapeutically effective amount of the human mesenchymal stem cell population wherein the human mesenchymal stem cell population is administered within about 96 hours from the time point the human mesenchymal stem cell population has been harvested.

2. The method of claim 1, wherein the mesenchymal stem cell population is applied in a unit dosage of about 10 million cells.

3. The method of claim 1, wherein the wound is caused by diabetic disease.

4. The method of claim 1, wherein at least 98% cells of the isolated mesenchymal stem cell population express each of CD73, CD90 and CD105 and lack expression of the following markers: CD34, CD45 and HLA-DR (Human Leukocyte Antigen-antigen D Related).

5. The method of claim 4, wherein at least 99% cells of the isolated mesenchymal stem cell population express each of CD73, CD90 and CD105 and lack expression of the following markers: CD34, CD45 and HLA-DR (Human Leukocyte Antigen-antigen D Related).

6. The method of claim 3, wherein the wound is a diabetic wound.

7. The method of claim 1, wherein the mesenchymal stem cell population is applied once or twice a week for up to 8 weeks in a dosage of 100,000 cells/cm$^2$ to 500,000 cells/cm$^2$ skin/wound area.

* * * * *

SEQUENCE LISTING

```
<160> NUMBER OF SEQ ID NOS: 13

<210> SEQ ID NO 1
<211> LENGTH: 574
<212> TYPE: PRT
<213> ORGANISM: human

<400> SEQUENCE: 1

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255
```

Glu Val Pro Ala Gly Lys Tyr Pro Phe Ile Val Thr Ser Asp Asp Gly
                260                 265                 270

Arg Lys Val Pro Val Gln Ala Tyr Ala Phe Gly Lys Tyr Leu Gly
            275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570

<210> SEQ ID NO 2
<211> LENGTH: 161
<212> TYPE: PRT
<213> ORGANISM: human

<400> SEQUENCE: 2

Met Asn Leu Ala Ile Ser Ile Ala Leu Leu Leu Thr Val Leu Gln Val
1               5                   10                  15

Ser Arg Gly Gln Lys Val Thr Ser Leu Thr Ala Cys Leu Val Asp Gln
            20                  25                  30

Ser Leu Arg Leu Asp Cys Arg His Glu Asn Thr Ser Ser Ser Pro Ile
        35                  40                  45

```
Gln Tyr Glu Phe Ser Leu Thr Arg Glu Thr Lys Lys His Val Leu Phe
     50                  55                  60

Gly Thr Val Gly Val Pro Glu His Thr Tyr Arg Ser Arg Thr Asn Phe
 65                  70                  75                  80

Thr Ser Lys Tyr Asn Met Lys Val Leu Tyr Leu Ser Ala Phe Thr Ser
                 85                  90                  95

Lys Asp Glu Gly Thr Tyr Thr Cys Ala Leu His His Ser Gly His Ser
             100                 105                 110

Pro Pro Ile Ser Ser Gln Asn Val Thr Val Leu Arg Asp Lys Leu Val
         115                 120                 125

Lys Cys Glu Gly Ile Ser Leu Leu Ala Gln Asn Thr Ser Trp Leu Leu
     130                 135                 140

Leu Leu Leu Leu Ser Leu Ser Leu Leu Gln Ala Thr Asp Phe Met Ser
145                 150                 155                 160

Leu
```

<210> SEQ ID NO 3
<211> LENGTH: 658
<212> TYPE: PRT
<213> ORGANISM: human

<400> SEQUENCE: 3

```
Met Asp Arg Gly Thr Leu Pro Leu Ala Val Ala Leu Leu Leu Ala Ser
  1               5                  10                  15

Cys Ser Leu Ser Pro Thr Ser Leu Ala Glu Thr Val His Cys Asp Leu
                 20                  25                  30

Gln Pro Val Gly Pro Glu Arg Gly Glu Val Thr Tyr Thr Thr Ser Gln
             35                  40                  45

Val Ser Lys Gly Cys Val Ala Gln Ala Pro Asn Ala Ile Leu Glu Val
 50                  55                  60

His Val Leu Phe Leu Glu Phe Pro Thr Gly Pro Ser Gln Leu Glu Leu
 65                  70                  75                  80

Thr Leu Gln Ala Ser Lys Gln Asn Gly Thr Trp Pro Arg Glu Val Leu
                 85                  90                  95

Leu Val Leu Ser Val Asn Ser Ser Val Phe Leu His Leu Gln Ala Leu
             100                 105                 110

Gly Ile Pro Leu His Leu Ala Tyr Asn Ser Ser Leu Val Thr Phe Gln
         115                 120                 125

Glu Pro Pro Gly Val Asn Thr Thr Glu Leu Pro Ser Phe Pro Lys Thr
     130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255
```

```
Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
            275                 280                 285

Gly Phe Lys Leu Pro Asp Thr Pro Gln Gly Leu Leu Gly Glu Ala Arg
290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
            355                 360                 365

Thr Leu Val Leu Lys Lys Glu Leu Val Ala His Leu Lys Cys Thr Ile
            370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Lys Lys Val His Cys Leu Asn Met Asp Ser Leu
            435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
            595                 600                 605

Ala Leu Trp Tyr Ile Tyr Ser His Thr Arg Ser Pro Ser Lys Arg Glu
    610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala
```

<210> SEQ ID NO 4
<211> LENGTH: 385
<212> TYPE: PRT
<213> ORGANISM: human

<400> SEQUENCE: 4

Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Gly Glu Asp Pro Tyr Tyr Thr Glu Asn Gly Gly Gly
                325                 330                 335

Gln Gly Tyr Ser Ser Gly Pro Gly Thr Ser Pro Glu Ala Gln Gly Lys
            340                 345                 350

Ala Ser Val Asn Arg Gly Ala Gln Glu Asn Gly Thr Gly Gln Ala Thr
        355                 360                 365

Ser Arg Asn Gly His Ser Ala Arg Gln His Val Val Ala Asp Thr Glu
    370                 375                 380

Leu
385

<210> SEQ ID NO 5
<211> LENGTH: 1304
<212> TYPE: PRT
<213> ORGANISM: human

<400> SEQUENCE: 5

```
Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
        35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
        115                 120                 125

Ala Ala Asn Ala Lys Leu Asn Pro Thr Pro Gly Ser Asn Ala Ile Ser
    130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
                165                 170                 175

Ala Leu Pro Ala Arg Thr Ser Asn Thr Thr Ile Thr Ala Asn Thr Ser
            180                 185                 190

Asp Ala Tyr Leu Asn Ala Ser Glu Thr Thr Thr Leu Ser Pro Ser Gly
        195                 200                 205

Ser Ala Val Ile Ser Thr Thr Thr Ile Ala Thr Thr Pro Ser Lys Pro
    210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
            260                 265                 270

Glu Cys Lys Asn Ala Ser Val Ser Ile Ser His Asn Ser Cys Thr Ala
        275                 280                 285

Pro Asp Lys Thr Leu Ile Leu Asp Val Pro Pro Gly Val Glu Lys Phe
    290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
        355                 360                 365
```

```
Ile Leu Tyr Asn Asn His Lys Phe Thr Asn Ala Ser Lys Ile Ile Lys
    370                 375                 380

Thr Asp Phe Gly Ser Pro Gly Glu Pro Gln Ile Ile Phe Cys Arg Ser
385                 390                 395                 400

Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
                420                 425                 430

Leu Asn Leu Asp Lys Asn Leu Ile Lys Tyr Asp Leu Gln Asn Leu Lys
            435                 440                 445

Pro Tyr Thr Lys Tyr Val Leu Ser Leu His Ala Tyr Ile Ile Ala Lys
    450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
                500                 505                 510

His Glu Arg Tyr His Leu Glu Val Glu Ala Gly Asn Thr Leu Val Arg
            515                 520                 525

Asn Glu Ser His Lys Asn Cys Asp Phe Arg Val Lys Asp Leu Gln Tyr
    530                 535                 540

Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
                565                 570                 575

Leu Ile Ala Phe Leu Ala Phe Leu Ile Ile Val Thr Ser Ile Ala Leu
            580                 585                 590

Leu Val Val Leu Tyr Lys Ile Tyr Asp Leu His Lys Lys Arg Ser Cys
    595                 600                 605

Asn Leu Asp Glu Gln Gln Glu Leu Val Glu Arg Asp Asp Glu Lys Gln
610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
            660                 665                 670

Pro Phe Asn Gln Asn Lys Asn Arg Tyr Val Asp Ile Leu Pro Tyr Asp
    675                 680                 685

Tyr Asn Arg Val Glu Leu Ser Glu Ile Asn Gly Asp Ala Gly Ser Asn
690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Val Ile Val Met Val Thr Arg Cys
            740                 745                 750

Glu Glu Gly Asn Arg Asn Lys Cys Ala Glu Tyr Trp Pro Ser Met Glu
    755                 760                 765

Glu Gly Thr Arg Ala Phe Gly Asp Val Val Val Lys Ile Asn Gln His
770                 775                 780
```

-continued

```
Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
            805                 810                 815

Trp Pro Asp His Gly Val Pro Glu Asp Pro His Leu Leu Leu Lys Leu
        820                 825                 830

Arg Arg Arg Val Asn Ala Phe Ser Asn Phe Phe Ser Gly Pro Ile Val
    835                 840                 845

Val His Cys Ser Ala Gly Val Gly Arg Thr Gly Thr Tyr Ile Gly Ile
850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
            885                 890                 895

Glu Ala Gln Tyr Ile Leu Ile His Gln Ala Leu Val Glu Tyr Asn Gln
        900                 905                 910

Phe Gly Glu Thr Glu Val Asn Leu Ser Glu Leu His Pro Tyr Leu His
    915                 920                 925

Asn Met Lys Lys Arg Asp Pro Pro Ser Glu Pro Ser Pro Leu Glu Ala
930                 935                 940

Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
            965                 970                 975

Pro Tyr Asp Tyr Asn Arg Val Pro Leu Lys His Glu Leu Glu Met Ser
        980                 985                 990

Lys Glu Ser Glu His Asp Ser Asp Glu Ser Ser Asp Asp Ser Asp
            995                 1000                1005

Ser Glu Glu Pro Ser Lys Tyr Ile Asn Ala Ser Phe Ile Met Ser
        1010                1015                1020

Tyr Trp Lys Pro Glu Val Met Ile Ala Ala Gln Gly Pro Leu Lys
        1025                1030                1035

Glu Thr Ile Gly Asp Phe Trp Gln Met Ile Phe Gln Arg Lys Val
        1040                1045                1050

Lys Val Ile Val Met Leu Thr Glu Leu Lys His Gly Asp Gln Glu
        1055                1060                1065

Ile Cys Ala Gln Tyr Trp Gly Glu Gly Lys Gln Thr Tyr Gly Asp
        1070                1075                1080

Ile Glu Val Asp Leu Lys Asp Thr Asp Lys Ser Ser Thr Tyr Thr
        1085                1090                1095

Leu Arg Val Phe Glu Leu Arg His Ser Lys Arg Lys Asp Ser Arg
        1100                1105                1110

Thr Val Tyr Gln Tyr Gln Tyr Thr Asn Trp Ser Val Glu Gln Leu
        1115                1120                1125

Pro Ala Glu Pro Lys Glu Leu Ile Ser Met Ile Gln Val Val Lys
        1130                1135                1140

Gln Lys Leu Pro Gln Lys Asn Ser Ser Glu Gly Asn Lys His His
        1145                1150                1155

Lys Ser Thr Pro Leu Leu Ile His Cys Arg Asp Gly Ser Gln Gln
        1160                1165                1170

Thr Gly Ile Phe Cys Ala Leu Leu Asn Leu Leu Glu Ser Ala Glu
        1175                1180                1185
```

-continued

```
Thr Glu Glu Val Val Asp Ile Phe Gln Val Val Lys Ala Leu Arg
    1190                1195                1200

Lys Ala Arg Pro Gly Met Val Ser Thr Phe Glu Gln Tyr Gln Phe
    1205                1210                1215

Leu Tyr Asp Val Ile Ala Ser Thr Tyr Pro Ala Gln Asn Gly Gln
    1220                1225                1230

Val Lys Lys Asn Asn His Gln Glu Asp Lys Ile Glu Phe Asp Asn
    1235                1240                1245

Glu Val Asp Lys Val Lys Gln Asp Ala Asn Cys Val Asn Pro Leu
    1250                1255                1260

Gly Ala Pro Glu Lys Leu Pro Glu Ala Lys Glu Gln Ala Glu Gly
    1265                1270                1275

Ser Glu Pro Thr Ser Gly Thr Glu Gly Pro Glu His Ser Val Asn
    1280                1285                1290

Gly Pro Ala Ser Pro Ala Leu Asn Gln Gly Ser
    1295                1300

<210> SEQ ID NO 6
<211> LENGTH: 254
<212> TYPE: PRT
<213> ORGANISM: human

<400> SEQUENCE: 6

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
                20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
        50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240
```

```
Gly Val Arg Lys Ser Asn Ala Ala Glu Arg Gly Pro Leu
            245                 250

<210> SEQ ID NO 7
<211> LENGTH: 503
<212> TYPE: PRT
<213> ORGANISM: human

<400> SEQUENCE: 7

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350
```

```
Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 8
<211> LENGTH: 232
<212> TYPE: PRT
<213> ORGANISM: human

<400> SEQUENCE: 8

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205
```

Thr Asp Ser Arg Cys Lys Ala Arg Gln Leu Glu Leu Asn Glu Arg Thr
            210                 215                 220

Cys Arg Cys Asp Lys Pro Arg Arg
225                 230

<210> SEQ ID NO 9
<211> LENGTH: 1089
<212> TYPE: PRT
<213> ORGANISM: human

<400> SEQUENCE: 9

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

```
Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
        450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
        530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
        690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750
```

```
Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
        770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
            805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
            835                 840                 845

Tyr Val Ser Lys Gly Ser Thr Phe Leu Pro Val Lys Trp Met Ala Pro
            850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
            885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
            930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
            995                 1000                1005

Glu Gln Arg Leu Ser Ala Asp Ser Gly Tyr Ile Ile Pro Leu Pro
        1010                1015                1020

Asp Ile Asp Pro Val Pro Glu Glu Glu Asp Leu Gly Lys Arg Asn
        1025                1030                1035

Arg His Ser Ser Gln Thr Ser Glu Glu Ser Ala Ile Glu Thr Gly
        1040                1045                1050

Ser Ser Ser Ser Thr Phe Ile Lys Arg Glu Asp Glu Thr Ile Glu
        1055                1060                1065

Asp Ile Asp Met Met Asp Asp Ile Gly Ile Asp Ser Ser Asp Leu
        1070                1075                1080

Val Glu Asp Ser Phe Leu
        1085

<210> SEQ ID NO 10
<211> LENGTH: 498
<212> TYPE: PRT
<213> ORGANISM: human

<400> SEQUENCE: 10

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30
```

-continued

```
Tyr Asn Arg Ile Gln His Gly Gln Cys Ala Tyr Thr Phe Ile Leu Pro
         35                  40                  45

Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
            435                 440                 445
```

```
Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 11
<211> LENGTH: 728
<212> TYPE: PRT
<213> ORGANISM: human

<400> SEQUENCE: 11

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320
```

```
Trp Asn Gly Ile Pro Cys Gln Arg Trp Asp Ser Gln Tyr Pro His Glu
            325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
            405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
            725
```

```
<210> SEQ ID NO 12
<211> LENGTH: 241
<212> TYPE: PRT
<213> ORGANISM: human

<400> SEQUENCE: 12

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 13
<211> LENGTH: 178
<212> TYPE: PRT
<213> ORGANISM: human

<400> SEQUENCE: 13

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95
```

```
Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```